United States Patent [19]
Metz et al.

[11] Patent Number: 5,679,881
[45] Date of Patent: Oct. 21, 1997

[54] NUCLEIC ACID SEQUENCES ENCODING A PLANT CYTOPLASMIC PROTEIN INVOLVED IN FATTY ACYL-COA METABOLISM

[75] Inventors: James George Metz, Davis; Kathryn Dennis Lardizabal, Woodland; Michael Lassner, Davis, all of Calif.

[73] Assignee: Calgene, Inc., Davis, Calif.

[21] Appl. No.: 265,047

[22] Filed: Jun. 23, 1994

Related U.S. Application Data

[63] Continuation-in-part of Ser. No. 796,256, Nov. 20, 1991, abandoned, Ser. No. 933,411, Aug. 21, 1992, abandoned, Ser. No. 66,299, May 20, 1993, Pat. No. 5,445,947, and Ser. No. 160,602, PCT/US92/09863 filed Nov. 13, 1992, abandoned.

[51] Int. Cl.$^6$ .................. C12N 15/29; C12N 15/82; A01H 4/00; A01H 5/00
[52] U.S. Cl. .................. 800/205; 800/250; 800/255; 435/69.1; 435/172.3; 435/419; 435/320.1; 536/23.6; 536/24.1; 536/24.5
[58] Field of Search .................. 435/69.1, 70.1, 435/71.2, 172.1, 172.3, 134, 240.4, 252.3; 536/23.2, 23.6; 800/200, 205, 250, 255, DIG. 17

[56] References Cited

U.S. PATENT DOCUMENTS

| | | | |
|---|---|---|---|
| 5,445,947 | 8/1995 | Metz et al. | 435/69.1 |
| 5,475,099 | 12/1995 | Knauf et al. | 536/23.6 |
| 5,510,255 | 4/1996 | Knauf et al. | 435/172.3 |

FOREIGN PATENT DOCUMENTS

WO 93 10241  5/1993  WIPO.

OTHER PUBLICATIONS

Garver et. al. "A High Performance Liquid Chromatography-Based Radiometric Assay for Acl-COA: Alcohol Transacylase for Jojoba" *Analytical Biochemistry*, (1992) 207: No. 2 Dec., 1992

Stumpf, et. al. "Pathways of Fatty Acid Biosynthesis Plants with Particular Reference to Developing Rapeseed" *High and Low Erucic Rapeseed Oils*, Academic Press, Canada 1993 132–141.

Bessoule, et. al. "Partial Purification of the Acyl-COA Elongase of *Allium porrum* Leaves" *Archives of Biochemistry and Biophysics* (1989) 268 No. 2 475–484.

Pushnik, et. al. "Characterization of the Biosynthetic Pathway for Formation of Liquid Wax in Jojoba" *The Southwest Consortium Fourth Annual Meeting*, Feb. 9, 1989, Riverside, CA.

Wildner, et. al. "Wax Ester Biosynthesis in *Euglena gracilis*" *The Southwest Consortium Fifth Annual Meeting*, Apr. 22–24, 1990, Las Cruces, N.M.

Pollard, et. al. "Studies on Biosynthesis of Waxes by Developing Jojoba Seed II. The Demonstration of Wax Biosynthesis by Cell-Free Homogenates" *Lipids* (1979) 14 No. 7 651–662.

Wu, et. al. "Studies on Biosynthesis of Waxes by Developing Jojoba Seed III. The Demonstration of Wax Esters from Acyl-COA and Long Chain Alcohols" *Lipids* (1981) 16 No. 12 897–902.

Ohlroge, et. al. "The Genetics of Plant Lipids" *International Journal of Biochemistry and Biophysics Lipids and Lipid Metabolism* (1991) 1082 1–27.

von Wettstein-Knowles, P.M., "Waxes, Cutin and Suberin" *Lipid Metabolism in Plants* 1993 CRC Press 127–166.

van de Loo, et. al., "Unusual Fatty Acids" *Lipid Metabolism in Plants* 1993 CRC Press 91–126.

Harwood, J.L. "Fatty Acid Metabolism" *Annual Review of Plant Physiology and Plant Molecular Biology*, 1988 39 101–138.

Creach, et. al. "Solubilization of Acyl-CoA Elongase from Developing Rapeseed (*Brassica napus* L.)" *JAOCS* Nov. 1993 70: No. 11 1129–1133.

Lessire, et. al. "Involvement of a β-ketoacyl-CoA Intermediate in acyl-CoA Elongation by an acyl-CoA Elongase Purified from Leek Epidermal Cells" *Biochima et. Biophysica Acta* 1989 1006 35–40 WO 93 10241 (Calgene) May 1993.

Akada et al. "Glycine max Chalcone Synthase (CHS6) Gene, Complete CDS." *Database Embl Sequence Release 33 Accession No. L03352.5* Oct. 1992.

Batschauer, A. "Mustard Chalcone Synthase Gene (E.C. 2.3.1.74)" *Database Embl Sequence Release 22; Accession No. X16437.1* Dec. 1989.

Murphy, et al. "Elongases synthesizing very long chain monounssaturated fatty acids in developing oilseeds and their solubilization" *Z. Naturforschung*, vol. 44C, No. 7/8, 629–634 Jul. 1989.

Newman, T. "392 Arabidopsis Thialana cDNA clone 38D4T7" *Database Embl Sequence Release 36. Accession No. T04345.30* Aug., 1993.

Quigley "A thaliana transcribed sequence; clone GBG3e129b" Database Embl Sequence Release 36; Accession No. Z26005.8 Sep., 1993.

(List continued on next page.)

*Primary Examiner*—Douglas W. Robinson
*Assistant Examiner*—Thomas Haas
*Attorney, Agent, or Firm*—Carl J. Schwedler; Donna E. Scherer

[57] ABSTRACT

By this invention, a plant cytoplasmic synthase protein is provided which is selected from the group consisting of a β-ketoacyl-CoA synthase and a wax synthase, and is also free from intact cells of said plant and capable of catalyzing the production of very long chain fatty acid molecules. Also contemplated are constructs comprising the nucleic acid sequence and a heterologous DNA sequence not naturally associated with the plant cytoplasmic protein encoding sequences, and which provide for at least transcription of a plant cytoplasmic protein encoding sequence in a host cell. In this fashion very long chain fatty acid molecules may be produced in a host cell. Included are methods of modifying the composition of very long chain fatty acid molecules in a plant cell.

9 Claims, 21 Drawing Sheets

OTHER PUBLICATIONS

Kunst et al. "Fatty acid elongation in developing seeds of *Arabidopsis thaliana*", *Plant Physiol. Biochem.* vol. 30, 425–434, 1992.

Taylor et al. "Biosynthesis of Acyl Lipids Containing Very–Long Chain Fatty Acids in Microspore-Derived and Zygotic Embryos of Brassica napus L. cv reston 1" *Plant Physiology*, vol. 99, 1609–1618, 1992.

Whitfield et al. "Sub–Cellular Localization of Fatty Acids Elongase in Developing Seeds of *Lunaria annua* and *Brassica napus*" *Phytochemistry*, vol. 32, No. 2, 255–258, 1933.

Fehling et al. "Solubilization and partial purification of constituents of acyl–CoA elongase from *Lunaria annua*-"*Biochimica Biophysica Acta* vol. 1126 88–94, 1992.

```
AAATCCTCCA CTCATACACT CCACTTCTCT CTCTCTCTCT CTCTCTCTGA AACAATTGA    60

GTAGCAAACT TAAAAGAAA ATG GAG GAA ATG GGA AGC ATT TTA GAG TTT CTT   112
                     Met Glu Glu Met Gly Ser Ile Leu Glu Phe Leu
                      1                   5                  10

GAT AAC AAA GCC ATT TTG GTC ACT GGT GCT ACT GGC TCC TTA GCA AAA   160
Asp Asn Lys Ala Ile Leu Val Thr Gly Ala Thr Gly Ser Leu Ala Lys
             15                  20                  25

ATT TTT GTG GAG AAG GTA CTG AGG AGT CAA CCG AAT GTG AAG AAA CTC   208
Ile Phe Val Glu Lys Val Leu Arg Ser Gln Pro Asn Val Lys Lys Leu
         30                  35                  40

TAT CTT CTT TTG AGA GCA ACC GAT GAC GAG ACA GCT GCT CTA CGC TTG   256
Tyr Leu Leu Leu Arg Ala Thr Asp Asp Glu Thr Ala Ala Leu Arg Leu
     45                  50                  55

CAA AAT GAG GTT TTT GGA AAA GAG TTG TTC AAA GTT CTG AAA CAA AAT   304
Gln Asn Glu Val Phe Gly Lys Glu Leu Phe Lys Val Leu Lys Gln Asn
 60                  65                  70                  75
```

FIG. 1A

| TTA | GGT | GCA | AAT | TTC | TAT | TCC | TTT | GTA | TCA | GAA | AAA | GTG | ACT | GTA | GTA | 352 |
| Leu | Gly | Ala | Asn | Phe | Tyr | Ser | Phe | Val | Ser | Glu | Lys | Val | Thr | Val | Val | |
| | | | 80 | | | | | 85 | | | | | | 90 | | |

| CCC | GGT | GAT | ATT | ACT | GGT | GAA | GAC | TTG | TGT | CTC | AAA | GAC | GTC | AAT | TTG | 400 |
| Pro | Gly | Asp | Ile | Thr | Gly | Glu | Asp | Leu | Cys | Leu | Lys | Asp | Val | Asn | Leu | |
| | | | 95 | | | | | 100 | | | | | | 105 | | |

| AAG | GAA | GAA | ATG | TGG | AGG | GAA | ATC | GAT | GTT | GTC | AAT | CTA | GCT | GCT | 448 |
| Lys | Glu | Glu | Met | Trp | Arg | Glu | Ile | Asp | Val | Val | Asn | Leu | Ala | Ala | |
| | 110 | | | | | 115 | | | | | 120 | | | | |

| ACA | ATC | AAC | TTC | ATT | GAA | AGG | TAC | GAC | GTG | TCT | CTG | CTT | ATC | AAC | ACA | 496 |
| Thr | Ile | Asn | Phe | Ile | Glu | Arg | Tyr | Asp | Val | Ser | Leu | Leu | Ile | Asn | Thr | |
| | | 125 | | | | | 130 | | | | | 135 | | | | |

| TAT | GGA | GCC | AAG | TAT | GTT | TTG | GAC | TTC | GCG | AAG | AAG | TGC | AAC | AAA | TTA | 544 |
| Tyr | Gly | Ala | Lys | Tyr | Val | Leu | Asp | Phe | Ala | Lys | Lys | Cys | Asn | Lys | Leu | |
| | 140 | | | | | 145 | | | | | 150 | | | | 155 | |

| AAG | ATA | TTT | GTT | CAT | GTA | TCT | ACT | GCT | TAT | GTA | TCT | GGA | GAG | AAA | AAT | 592 |
| Lys | Ile | Phe | Val | His | Val | Ser | Thr | Ala | Tyr | Val | Ser | Gly | Glu | Lys | Asn | |
| | | | 160 | | | | | 165 | | | | | | 170 | | |

FIG. 1B

```
GGG TTA ATA CTG GAG AAG CCT TAT TAT ATG GGC GAG TCA CTT AAT GGA    640
Gly Leu Ile Leu Glu Lys Pro Tyr Tyr Met Gly Glu Ser Leu Asn Gly
        175                 180                 185

AGA TTA GGT CTG GAC ATT AAT GTA GAG AAG AAA CTT GTG GAG GCA AAA    688
Arg Leu Gly Leu Asp Ile Asn Val Glu Lys Lys Leu Val Glu Ala Lys
        190                 195                 200

ATC AAT GAA CTT CAA GCA GCG GGG GCA ACG GAA AAG TCC ATT AAA TCG    736
Ile Asn Glu Leu Gln Ala Ala Gly Ala Thr Glu Lys Ser Ile Lys Ser
        205                 210                 215

ACA ATG AAG GAC ATG GGC ATC GAG AGG GCA AGA CAC TGG GGA TGG CCA    784
Thr Met Lys Asp Met Gly Ile Glu Arg Ala Arg His Trp Gly Trp Pro
        220                 225                 230             235

AAT GTG TAT GTA TTC ACC AAG GCA TTA GGG GAG ATG CTT TTG ATG CAA    832
Asn Val Tyr Val Phe Thr Lys Ala Leu Gly Glu Met Leu Leu Met Gln
        240                 245                 250

TAC AAA GGG GAC ATT CCG CTT ACT ATT ATT CGT CCC ACC ATC ATC ACC    880
Tyr Lys Gly Asp Ile Pro Leu Thr Ile Ile Arg Pro Thr Ile Ile Thr
        255                 260                 265
```

FIG. 1C

```
AGC ACT TTT AAA GAG CCC TTT CCT GGT TGG GTT GAA GGT GTC AGG ACC    928
Ser Thr Phe Lys Glu Pro Phe Pro Gly Trp Val Glu Gly Val Arg Thr
        270                 275                 280

ATC GAT AAT GTA CCT GTA TAT TAT GGT AAA GGG AGA TTG AGG TGT ATG    976
Ile Asp Asn Val Pro Val Tyr Tyr Gly Lys Gly Arg Leu Arg Cys Met
        285                 290                 295

CTT TGC GGA CCC AGC ACA ATA ATT GAC CTG ATA CCG GCA GAT ATG GTC   1024
Leu Cys Gly Pro Ser Thr Ile Ile Asp Leu Ile Pro Ala Asp Met Val
        300                 305                 310         315

GTG AAT GCA ACG ATA GTA GCC ATG GTG CAC GCA AAC CAA AGA TAC       1072
Val Asn Ala Thr Ile Val Ala Met Val Ala His Ala Asn Gln Arg Tyr
                320                 325                 330

GTA GAG CCG GTG ACA TAC CAT GTG GGA TCT TCA GCG GCG AAT CCA ATG   1120
Val Glu Pro Val Thr Tyr His Val Gly Ser Ser Ala Ala Asn Pro Met
        335                 340                 345

AAA CTG AGT GCA TTA CCA GAG ATG GCA CAC CGT TAC TTC ACC AAG AAT   1168
Lys Leu Ser Ala Leu Pro Glu Met Ala His Arg Tyr Phe Thr Lys Asn
        350                 355                 360
```

FIG. 1D

```
CCA TGG ATC AAC CCG GAT CGC AAC CCA GTA CAT GTG GGT CGG GCT ATG   1216
Pro Trp Ile Asn Pro Asp Arg Asn Pro Val His Val Gly Arg Ala Met
365                 370                 375

GTC TTC TCC TTC TCC ACC TTC CAC CTT TAT CTC ACC CTT AAT TTC       1264
Val Phe Ser Phe Ser Thr Phe His Leu Tyr Leu Thr Leu Asn Phe
380                 385                 390                 395

CTC CTT CCT TTG AAG GTA CTG GAG ATA GCA AAT ACA ATA TTC TGC CAA   1312
Leu Leu Pro Leu Lys Val Leu Glu Ile Ala Asn Thr Ile Phe Cys Gln
    400                 405                 410

TGG TTC AAG GGT AAG TAC ATG GAT CTT AAA AGG AAG ACG AGG TTG TTG   1360
Trp Phe Lys Gly Lys Tyr Met Asp Leu Lys Arg Lys Thr Arg Leu Leu
    415                 420                 425

TTG CGT TTA GTA GAC ATT TAT AAA CCC TAC CTC TTC TTC CAA GGC ATC   1408
Leu Arg Leu Val Asp Ile Tyr Lys Pro Tyr Leu Phe Phe Gln Gly Ile
    430                 435                 440

TTT GAT GAC ATG AAC ACT GAG AAG TTG CGG ATT GCT GCA AAA GAA AGC   1456
Phe Asp Asp Met Asn Thr Glu Lys Leu Arg Ile Ala Ala Lys Glu Ser
445                 450                 455
```

FIG. 1E

```
ATA GTT GAA GCT GAT ATG TTT TAC TTT GAT CCC AGG GCA ATT AAC TGG   1504
Ile Val Glu Ala Asp Met Phe Tyr Phe Asp Pro Arg Ala Ile Asn Trp
460                     465                     470           475

GAA GAT TAC TTC TTG AAA ACT CAT TTC CCA GGN GTC GTA GAG CAC GTT   1552
Glu Asp Tyr Phe Leu Lys Thr His Phe Pro Gly Val Val Glu His Val
                480                     485                 490

CTT AAC TAAAAGTTAC GGTACGAAAA TGAGAAGATT GGAATGCATG CACCGAAAGN    1608
Leu Asn

NCAACATAAA AGACGTGGTT AAAGTCATGG TCAAAAAAGA AATAAAATGC AGTTAGGTTT 1668

GTGTTGCAGT TTTGATTCCT TGTATTGTTA CTTGTACTTT TGATCTTTTT CTTTTTTAAT 1728

GAAATTTCTC TCTTTGTTTT GTGAAAAAAA AAAAAAAAAA GAGCTCCTGC AGAAGCTT   1786
```

FIG. 1F

GGAACTCCAT CCCTTCCTCC CTCACTCCTC TCTCTACA ATG AAG GCC AAA ACA ATC    56
                                        Met Lys Ala Lys Thr Ile
                                         1               5

ACA AAC CCG GAG ATC CAA GTC TCC ACG ACC ATG ACC ACG ACC ACG          104
Thr Asn Pro Glu Ile Gln Val Ser Thr Thr Met Thr Thr Thr Thr
         10                  15                  20

ACT ATG ACC GCC ACT CTC CCC AAC TTC AAG TCC TCC ATC AAC TTA CAC      152
Thr Met Thr Ala Thr Leu Pro Asn Phe Lys Ser Ser Ile Asn Leu His
         25                  30                  35

CAC GTC AAG CTC GGC TAC CAC TAC TTA ATC TCC AAT GCC CTC TTC CTC      200
His Val Lys Leu Gly Tyr His Tyr Leu Ile Ser Asn Ala Leu Phe Leu
         40                  45                  50

GTA TTC ATC CCC CTT TTG GGC CTC GCT TCG GCC CAT CTC TCC TCC TTC      248
Val Phe Ile Pro Leu Leu Gly Leu Ala Ser Ala His Leu Ser Ser Phe
         55                  60                  65              70

FIG. 2A

| | | | | | | | | | | | | | | | | |
|---|---|---|---|---|---|---|---|---|---|---|---|---|---|---|---|---|
| TCG | GCC | CAT | GAC | TTG | TCC | CTG | CTC | CTT | GAC | CTC | CTT | CGC | CGC | AAC | CTC | 296 |
| Ser | Ala | His | Asp | Leu | Ser | Leu | Leu | Leu | Asp | Leu | Leu | Arg | Arg | Asn | Leu | |
| | | | | 75 | | | | | 80 | | | | | 85 | | |

| | | | | | | | | | | | | | | | | |
|---|---|---|---|---|---|---|---|---|---|---|---|---|---|---|---|---|
| CTC | CCT | GTT | GTC | GTT | TGT | TCT | TTC | CTC | TTC | GTT | TTA | TTA | GCA | ACC | CTA | 344 |
| Leu | Pro | Val | Val | Val | Cys | Ser | Phe | Leu | Phe | Val | Leu | Leu | Ala | Thr | Leu | |
| | | 90 | | | | | 95 | | | | | 100 | | | | |

| | | | | | | | | | | | | | | | | |
|---|---|---|---|---|---|---|---|---|---|---|---|---|---|---|---|---|
| CAT | TTC | TTG | ACC | CGG | CCC | AGG | AAT | GTC | TAC | TTG | GTG | GAC | TTT | GGA | TGC | 392 |
| His | Phe | Leu | Thr | Arg | Pro | Arg | Asn | Val | Tyr | Leu | Val | Asp | Phe | Gly | Cys | |
| | 105 | | | | | 110 | | | | | 115 | | | | | |

| | | | | | | | | | | | | | | | | |
|---|---|---|---|---|---|---|---|---|---|---|---|---|---|---|---|---|
| TAT | AAG | CCT | CAA | CCG | AAC | CTG | ATG | ACA | TCC | CAC | GAG | ATG | TTC | ATG | GAC | 440 |
| Tyr | Lys | Pro | Gln | Pro | Asn | Leu | Met | Thr | Ser | His | Glu | Met | Phe | Met | Asp | |
| 120 | | | | | 125 | | | | | 130 | | | | | | |

| | | | | | | | | | | | | | | | | |
|---|---|---|---|---|---|---|---|---|---|---|---|---|---|---|---|---|
| CGG | ACC | TCC | CGG | GCC | GGG | TCG | TTT | TCT | AAG | GAG | AAT | ATT | GAG | TTT | CAG | 488 |
| Arg | Thr | Ser | Arg | Ala | Gly | Ser | Phe | Ser | Lys | Glu | Asn | Ile | Glu | Phe | Gln | |
| 135 | | | | 140 | | | | | 145 | | | | | 150 | | |

| | | | | | | | | | | | | | | | | |
|---|---|---|---|---|---|---|---|---|---|---|---|---|---|---|---|---|
| AGG | AAG | ATC | TTG | GAG | AGG | GCC | GGT | ATG | GGT | CGG | GAA | ACC | TAT | GTC | CCC | 536 |
| Arg | Lys | Ile | Leu | Glu | Arg | Ala | Gly | Met | Gly | Arg | Glu | Thr | Tyr | Val | Pro | |
| | | 155 | | | | | 160 | | | | | | | 165 | | |

FIG. 2B

| | | | | | | | | | | | | | | | | |
|---|---|---|---|---|---|---|---|---|---|---|---|---|---|---|---|---|
| GAA | TCC | GTC | ACT | AAG | GTG | CCC | GCC | GAG | CCG | AGC | ATA | GCA | GCA | GCC | AGG | 584 |
| Glu | Ser | Val | Thr | Lys | Val | Pro | Ala | Glu | Pro | Ser | Ile | Ala | Ala | Ala | Arg | |
| | | 170 | | | | | 175 | | | | | 180 | | | | |
| GCC | GAG | GCG | GAG | GAG | GTG | ATG | TAC | GGG | GCG | ATC | GAC | GAG | GTG | TTG | GAG | 632 |
| Ala | Glu | Ala | Glu | Glu | Val | Met | Tyr | Gly | Ala | Ile | Asp | Glu | Val | Leu | Glu | |
| | 185 | | | | | 190 | | | | | 195 | | | | | |
| AAG | ACG | GGG | GTG | AAG | CCG | AAG | CAG | ATA | GGA | ATA | CTG | GTG | ANC | TGC | | 680 |
| Lys | Thr | Gly | Val | Lys | Pro | Lys | Gln | Ile | Gly | Ile | Leu | Val | Val | Xxx | Cys | |
| 200 | | | | | 205 | | | | | 210 | | | | | | |
| AGC | TTG | TTT | AAC | CCA | ACG | CCG | TCG | CTG | TCA | TCC | ATG | ATA | GTT | AAC | CAT | 728 |
| Ser | Leu | Phe | Asn | Pro | Thr | Pro | Ser | Leu | Ser | Ser | Met | Ile | Val | Asn | His | |
| 215 | | | | | 220 | | | | | 225 | | | | | 230 | |
| TAC | AAG | CTN | AGG | GGT | AAT | ATA | CTT | AGC | TAT | AAT | CTT | GCC | ATG | GGT | | 776 |
| Tyr | Lys | Leu | Arg | Gly | Asn | Ile | Leu | Ser | Tyr | Asn | Leu | Gly | Gly | Met | Gly | |
| | | | 235 | | | | | 240 | | | | | 245 | | | |
| TGC | AGT | GCT | GGG | CTC | ATT | TCC | ATT | GAT | CTT | GCC | AAG | GAC | CTC | CTA | CAG | 824 |
| Cys | Ser | Ala | Gly | Leu | Ile | Ser | Ile | Asp | Leu | Ala | Lys | Asp | Leu | Leu | Gln | |
| 250 | | | | | 255 | | | | | 260 | | | | | | |

FIG. 2C

```
GTT TAC CGT AAA AAC ACA TAT GTG TTA GTA GTG AGC ACG GAA AAC ATG    872
Val Tyr Arg Lys Asn Thr Tyr Val Leu Val Val Ser Thr Glu Asn Met
    265                 270                 275

ACC CTT AAT TGG TAC TGG GGC AAT GAC CGC TCC ATG CTT ATC ACC AAC    920
Thr Leu Asn Trp Tyr Trp Gly Asn Asp Arg Ser Met Leu Ile Thr Asn
    280                 285                 290

TGC CTA TTT CGC ATG GGT GGC GCT GCC ATC ATC CTC TCA AAC CGC TGG    968
Cys Leu Phe Arg Met Gly Gly Ala Ala Ile Ile Leu Ser Asn Arg Trp
    295                 300                 305                 310

CGT GAT CGC CGA TCC AAG TAC CAA CTC CTT CAT ACA GTA CGC ACC       1016
Arg Asp Arg Arg Ser Lys Tyr Gln Leu Leu His Thr Val Arg Thr
    315                 320                 325

CAC AAG GGC GCT GAC GAC AAG TCC TAT AGA TGC GTC TTA CAA CAA GAA   1064
His Lys Gly Ala Asp Asp Lys Ser Tyr Arg Cys Val Leu Gln Gln Glu
    330                 335                 340

GAT GAA AAT AAC AAG GTA GGT GTT GCC TTA TCC AAG GAT CTG ATG GCA   1112
Asp Glu Asn Asn Lys Val Gly Val Ala Leu Ser Lys Asp Leu Met Ala
    345                 350                 355

GTT GCC GGT GAA GCC CTA AAG GCC AAC ATC ACG ACC CTT GGT CCC CTC   1160
Val Ala Gly Glu Ala Leu Lys Ala Asn Ile Thr Thr Leu Gly Pro Leu
    360                 365                 370
```

FIG. 2D

| | | | | | | | | | | | | | | | | |
|---|---|---|---|---|---|---|---|---|---|---|---|---|---|---|---|---|
| GTG | CTC | CCC | ATG | TCA | GAA | CAA | CTC | CTC | TTC | TTT | GCC | ACC | TTA | GTG | GCA | 1208 |
| Val | Leu | Pro | Met | Ser | Glu | Gln | Leu | Leu | Phe | Phe | Ala | Thr | Leu | Val | Ala | |
| 375 | | | | | 380 | | | | | 385 | | | | | 390 | |
| CGT | AAG | GTC | TTC | AAG | ATG | ACG | AAC | GTG | AAG | CCA | TAC | ATC | CCA | GAT | TTC | 1256 |
| Arg | Lys | Val | Phe | Lys | Met | Thr | Asn | Val | Lys | Pro | Tyr | Ile | Pro | Asp | Phe | |
| | | | | 395 | | | | | 400 | | | | | 405 | | |
| AAG | GCA | GCG | AAC | GAC | TTC | TGC | ATC | CAT | GCA | GGA | GGC | AAA | GCA | GTG | | 1304 |
| Lys | Ala | Ala | Asn | Asp | Phe | Cys | Ile | His | Ala | Gly | Gly | Lys | Ala | Val | | |
| | | 410 | | | | | 415 | | | | | 420 | | | | |
| TTG | GAT | GAG | CTC | GAG | AAG | AAC | TTG | GAG | TTG | ACG | CCA | TGG | CAC | CTT | GAA | 1352 |
| Leu | Asp | Glu | Leu | Glu | Lys | Asn | Leu | Glu | Leu | Thr | Pro | Trp | His | Leu | Glu | |
| | | 425 | | | | | 430 | | | | | 435 | | | | |
| CCC | TCG | AGG | ATG | ACA | CTG | TAT | AGG | TTT | GGG | AAC | ACA | TCG | AGT | AGC | TCA | 1400 |
| Pro | Ser | Arg | Met | Thr | Leu | Tyr | Arg | Phe | Gly | Asn | Thr | Ser | Ser | Ser | | |
| | | 440 | | | | | 445 | | | | | 450 | | | | |
| TTA | TGG | TAC | GAG | TTG | GCA | TAC | GCT | GAA | GCA | AAA | GGG | AGG | ATC | CGT | AAG | 1448 |
| Leu | Trp | Tyr | Glu | Leu | Ala | Tyr | Ala | Glu | Ala | Lys | Gly | Arg | Ile | Arg | Lys | |
| 455 | | | | | 460 | | | | | 465 | | | | | 470 | |

FIG. 2E

```
GGT GAT CGA ACT TGG ATG ATT GGA TTT GGT TCA GGT TTC AAG TGT AAC     1496
Gly Asp Arg Thr Trp Met Ile Gly Phe Gly Ser Gly Phe Lys Cys Asn
            475                 480                 485

AGT GTT GTG TGG AGG GCT TTG AGG AGT GTC AAT CCG GCT AGA GAG AAG     1544
Ser Val Val Trp Arg Ala Leu Arg Ser Val Asn Pro Ala Arg Glu Lys
            490                 495                 500

AAT CCT TGG ATG GAT GAA ATT GAG AAG TTC CCT GTC CAT GTG CCT AAA     1592
Asn Pro Trp Met Asp Glu Ile Glu Lys Phe Pro Val His Val Pro Lys
            505                 510                 515

ATC GCA CCT ATC GCT TCG TAGAACTGCT AGGATGTGAT TAGTAATGAA            1640
Ile Ala Pro Ile Ala Ser
            520

AAATGTGTAT TATGTTAGTG ATGTAGAAAA AGAAACTTTA GTTGATGGGT GAGAACATGT   1700

CTCATTGAGA ATAACGTGTG CATCGTTGTG TTG                                1733
```

FIG. 2F

```
GTCGACACA ATG AAG GCC AAA ACA ATC ACA AAC CCG GAG ATC CAA GTC TCC    51
         Met Lys Ala Lys Thr Ile Thr Asn Pro Glu Ile Gln Val Ser
          1                   5                  10

ACG ACC ATG ACC ACG ACC GCC ACT CTC CCC AAC TTC AAG                  99
Thr Thr Met Thr Thr Thr Ala Thr Leu Pro Asn Phe Lys
         15                  20                  25              30

TCC TCC ATC AAC TTA CAC CAC GTC AAG CTC GGC TAC CAC TAC TTA ATC     147
Ser Ser Ile Asn Leu His His Val Lys Leu Gly Tyr His Tyr Leu Ile
             35                  40                  45

TCC AAT GCC CTC TTC CTC GTA TTC ATC CCC CTT TTG GGC CTC GCT TCG     195
Ser Asn Ala Leu Phe Leu Val Phe Ile Pro Leu Leu Gly Leu Ala Ser
             50                  55                  60

GCC CAC CTC TCC TTC TCG GCC CAT GAC TTG TCC CTG CTC TTC GAC         243
Ala His Leu Ser Ser Phe Ser Ala His Asp Leu Ser Leu Phe Asp
         65                  70                  75

CTC CTT CGC CGC AAC CTC CTC CCC GTT GTC GTT TGT TCT TTC CTC TTC     291
Leu Leu Arg Arg Asn Leu Leu Pro Val Val Val Cys Ser Phe Leu Phe
         80                  85                  90
```

FIG. 3A

```
GTT TTA TTA GCA ACC CTA CAT TTC TTG ACC CGG CCT AGG AAT GTC TAC    339
Val Leu Leu Ala Thr Leu His Phe Leu Thr Arg Pro Arg Asn Val Tyr
 95                 100                 105                 110

TTG GTG GAC TTT GCC TGC TAT AAG CCT CAC CCG AAC CTG ATA ACA TCC    387
Leu Val Asp Phe Ala Cys Tyr Lys Pro His Pro Asn Leu Ile Thr Ser
                115                 120                 125

CAC GAG ATG TTC ATG GAC CGG ACC TCC CGG GCC GGG TCG TTT TCT AAG    435
His Glu Met Phe Met Asp Arg Thr Ser Arg Ala Gly Ser Phe Ser Lys
        130                 135                 140

GAG AAT ATT GAG TTT CAG AGG AAG ATC TTG GAG AGG GCC GGT ATG GGC    483
Glu Asn Ile Glu Phe Gln Arg Lys Ile Leu Glu Arg Ala Gly Met Gly
    145                 150                 155

CGG GAA ACC TAC GTC CCC GAA TCC GTC ACT AAG GTG CCG CCC GAG CCG    531
Arg Glu Thr Tyr Val Pro Glu Ser Val Thr Lys Val Pro Pro Glu Pro
160                 165                 170

AGC ATA GCA GCC AGG GCC GAG GCG GAG GAG GTG ATG TAC GGG GCG        579
Ser Ile Ala Ala Arg Ala Glu Ala Glu Glu Val Met Tyr Gly Ala
175                 180                 185                 190
```

FIG. 3B

```
ATC GAC GAG GTG TTG GAG AAG ACG GGG GTG AAG CCG AAG CAG ATA GGA    627
Ile Asp Glu Val Leu Glu Lys Thr Gly Val Lys Pro Lys Gln Ile Gly
                    195                 200                 205

ATA CTG GTG GTG AAC TGC AGC TTG TTT AAC CCA ACG CCG TCG CTG TCA    675
Ile Leu Val Val Asn Cys Ser Leu Phe Asn Pro Thr Pro Ser Leu Ser
                    210                 215                 220

TCC ATG ATA GTT AAC CAT TAC AAG CTT AGG GGT AAT ATA CTT AGC TAT    723
Ser Met Ile Val Asn His Tyr Lys Leu Arg Gly Asn Ile Leu Ser Tyr
                    225                 230                 235

AAT CTT GGT GGC ATG GGT AGT GCT GGG CTC ATT TCC ATT GAT CTT         771
Asn Leu Gly Gly Met Gly Ser Ala Gly Leu Ile Ser Ile Asp Leu
                    240                 245                 250

GCC AAG GAC CTC CTA CAG GTT TAC CGT AAC ACA TAT GTG TTA GTA GTG    819
Ala Lys Asp Leu Leu Gln Val Tyr Arg Asn Thr Tyr Val Leu Val Val
                    255                 260                 265                 270

AGC ACA GAA AAC ATG ACC CTT AAT TGG TAC TGG GGC AAT GAC CGC TCC    867
Ser Thr Glu Asn Met Thr Leu Asn Trp Tyr Trp Gly Asn Asp Arg Ser
                    275                 280                 285
```

FIG. 3C

```
ATG CTT ATC ACC AAC TGC CTA TTT CGC ATG GGT GGC GCT ATC ATC         915
Met Leu Ile Thr Asn Cys Leu Phe Arg Met Gly Gly Ala Ile Ile
            290                 295                 300

CTC TCA AAC CGC TGG CGT GAT CGT CGC CGA TCC AAG TAC CAA CTC CTT     963
Leu Ser Asn Arg Trp Arg Asp Arg Arg Arg Ser Lys Tyr Gln Leu Leu
            305                 310                 315

CAC ACA GTA CGC ACC CAC AAG GGC GCT GAC GAC AAG TCC TAT AGA TGC    1011
His Thr Val Arg Thr His Lys Gly Ala Asp Asp Lys Ser Tyr Arg Cys
        320                 325                 330

GTC TTA CAA CAA GAT GAA CAA AAT AAC AAG GTA GGT GTT GCC TTA TCC    1059
Val Leu Gln Gln Asp Glu Asn Asn Lys Val Gly Val Ala Leu Ser
        335                 340                 345         350

AAG GAT CTG ATG GCA GTT GCC GGT GAA GCC CTA AAG AAG GCC AAC ATC ACG 1107
Lys Asp Leu Met Ala Val Ala Gly Glu Ala Leu Lys Lys Ala Asn Ile Thr
            355                 360                 365

ACC CTT GGT CCC CTC GTG CTC CCC ATG TCA GAA CAA CTC CTC TTC TTT    1155
Thr Leu Gly Pro Leu Val Leu Pro Met Ser Glu Gln Leu Leu Phe Phe
        370                 375                 380
```

FIG. 3D

```
GCC ACC TTA GTG GCA CGT AAG GTC TTC AAG ATG ACG AAC GTG AAG CCA    1203
Ala Thr Leu Val Ala Arg Lys Val Phe Lys Met Thr Asn Val Lys Pro
            385                 390                 395

TAC ATC CCA GAT TTC AAG TTG GCA GCG AAG CAC TTC TGC ATC CAT GCA    1251
Tyr Ile Pro Asp Phe Lys Leu Ala Ala Lys His Phe Cys Ile His Ala
            400                 405                 410

GGA GGC AAA GCA GTG TTG GAT GAG CTC GAG ACG AAC TTG GAG TTG ACG    1299
Gly Gly Lys Ala Val Leu Asp Glu Leu Glu Thr Asn Leu Glu Leu Thr
            415                 420                 425         430

CCA TGG CAC CTT GAA CCC TCG AGG ATG ACA CTG TAT AGG TTT GGG AAC    1347
Pro Trp His Leu Glu Pro Ser Arg Met Thr Leu Tyr Arg Phe Gly Asn
            435                 440                 445

ACA TCG AGT AGC TCA TTA TGG TAC GAG TTG GCA TAC GCT GAA GCA AAA    1395
Thr Ser Ser Ser Ser Leu Trp Tyr Glu Leu Ala Tyr Ala Glu Ala Lys
            450                 455                 460

GGG AGG ATC CGT AAG GGT GAT CGA ACT TGG ATG ATT GGA TTT GGT TCA    1443
Gly Arg Ile Arg Lys Gly Asp Arg Thr Trp Met Ile Gly Phe Gly Ser
            465                 470                 475
```

FIG. 3E

```
GGT TTC AAG TGT AAC AGT GTT GTG TGG AGG GCT TTG AGG AGT GTC AAT    1491
Gly Phe Lys Cys Asn Ser Val Val Trp Arg Ala Leu Arg Ser Val Asn
            480                 485                 490

CCG GCT AGA GAG AAG AAT CCT TGG ATG GAT GAA ATT GAG AAT TTC CCT    1539
Pro Ala Arg Glu Lys Asn Pro Trp Met Asp Glu Ile Glu Asn Phe Pro
495                 500                 505                 510

GTC CAT GTG CCT AAA ATC GCA CCT ATC GCT TCG TAGAACTGCT AGGATGTGAT  1592
Val His Val Pro Lys Ile Ala Pro Ile Ala Ser
                515                 520

TAGTAATGAA AAATGTGTAT TATGTTAGTG ATGTAGAAAA AGAAACTTTA GTTGATGGGT  1652

GAGAACATGT CTCATTGAGA ATAACGTGTG CATCGTTGTG TTGAATTTGA ATTTGAGTAT  1712

TGGTGAAATT CTGTTAGAAT TGACGCATGA GTCATATATA TACAAATTTA AGTAAGATTT  1772

TACGCTTTCT T                                                       1783
```

FIG. 3F

```
GGCGCGCCGG TACCTCTAGA CCTGGCGATT CAACGTGGTC GGATCATGAC GCTTCCAGAA    60

AACATCGAGC AAGCTCTCAA AGCTGACCTC TTTCGGATCG TACTGAACCC GAACAATCTC   120

GTTATGTCCC GTCGTCTCCG AACAGACATC CTCGTAGCTC GGATTATCGA CGAATCCATG   180

GCTATACCCA ACCTCCGTCT TCGTCACGCC TGGAACCCTC TGGTACGCCA ATTCCGCTCC   240

CCAGAAGCAA CCGGCGCCGA ATTGCGCGAA TTGCTGACCT GGAGACGGAA CATCGTCGTC   300

GGGTCCTTGC GCGATTGCGG CGGAAGCCGG GTCGGGTTGG GGACGAGACC CGAATCCGAG   360

CCTGGTGAAG AGTTGTTCA TCGGAGATTT ATAGACGGAG ATGGATCGAG CGGTTTTGGG   420

GAAAGGGGAA GTGGGTTTGG CTCTTTTGGA TAGAGAGAGT GCAGCTTTGG AGAGAGACTG   480

GAGAGGTTTA GAGAGAGACG CGGCGGATAT TACCGGAGGA GAGGCGACGA GAGATAGCAT   540

TATCGAAGGG GAGGGAGAAA GAGTGACGTG GAGAAATAAG AAACCGTTAA GAGTCGGATA   600
```

FIG. 4A

```
TTTATCATAT TAAAAGCCCA ATGGGCCTGA ACCCATTTAA ACAAGACAGA TAAATGGCC    660

GTGTGTTAAG TTAACAGAGT GTTAACGTTC GGTTTCAAAT GCCAACGCCA TAGGAACAAA  720

ACAAACGTGT CCTCAAGTAA ACCCCTGCCG TTTACACCTC AATGGCTGCA TGGTGAAGCC  780

ATTAACACGT GGCGTAGGAT GCATGACGAC GCCATTGACA CTATTCATAG AATACATACA  840

TTCATATATC TCTAATCAAT TCAACTACTC ATTGTCATAG CTATTCGGAA AATACATACA  900

CATCCTTTTC TCTTCGATCT CTCTCAATTC ACAAGAAGCA AAGTCGACGG ATCCCTGCAG  960

TAAATTACGC CATGACTATT TTCATAGTCC AATAAGGCTG ATGTCGGGAG TCCAGTTTAT 1020

GAGCAATAAG GTGTTTAGAA TTTGATCAAT GTTTATAATA AAAGGGGGAA GATGATATCA 1080

CAGTCTTTTG TTCTTTTTGG CTTTTGTTAA ATTTGTGTGT TTCTATTTGT AAACCTCCTG 1140

TATATGTTGT ACTTCTTTCC CTTTTTAAGT GGTATCGTCT ATATGGTAAA ACGTTATGTT 1200
```

FIG. 4B

| | |
|---|---|
| TGGTCTTTCC TTTTCTCTGT TTAGGATAAA AAGACTGCAT GTTTTATCTT TAGTTATATT | 1260 |
| ATGTTGAGTA AATGAACTTT CATAGATCTG GTTCCGTAGA GTAGACTAGC AGCCGAGCTG | 1320 |
| AGCTGAACTG AACAGCTGGC AATGTGAACA CTGGATGCAA GATCAGATGT GAAGATCTCT | 1380 |
| AATATGGTGG TGGGATTGAA CATATCGTGT CTATATTTTT GTTGGCATTA AGCTCTTAAC | 1440 |
| ATAGATATAA CTGATGCAGT CATTGGTTCA TACACATATA TAGTAAGGAA TTACAATGGC | 1500 |
| AACCCAAACT TCAAAAACAG TAGGCCACCT GAATTGCCTT ATCGAATAAG AGTTTGTTTC | 1560 |
| CCCCCACTTC ATGGGATGTA ATACATGGGA TTTGGGAGTT TGAATGAACG TTGAGACATG | 1620 |
| GCAGAACCTC TAGAGGTACC GGCCGCGC | 1647 |

FIG. 4C

SEQUENCE LISTING ( 1 ) GENERAL INFORMATION:

( i i i ) NUMBER OF SEQUENCES: 16

( 2 ) INFORMATION FOR SEQ ID NO:1:

-continued ( i ) SEQUENCE CHARACTERISTICS:
  ( A ) LENGTH: 1786 base pairs
  ( B ) TYPE: nucleic acid
  ( C ) STRANDEDNESS: double
  ( D ) TOPOLOGY: linear ( i i ) MOLECULE TYPE: cDNA to mRNA ( x i ) SEQUENCE DESCRIPTION: SEQ ID NO:1:

| | | | | | | | | | | | |
|---|---|---|---|---|---|---|---|---|---|---|---|
| AAATCCTCCA | CTCATACACT | CCACTTCTCT | CTCTCTCTCT | CTCTCTCTGA | AACAATTTGA | | | | | | 60 |

| GTAGCAAACT | TAAAAGAAA | ATG | GAG | GAA | ATG | GGA | AGC | ATT | TTA | GAG | TTT | CTT | 112 |
|---|---|---|---|---|---|---|---|---|---|---|---|---|---|
| | | Met | Glu | Glu | Met | Gly | Ser | Ile | Leu | Glu | Phe | Leu | |
| | | 1 | | | 5 | | | | | 10 | | | |

| GAT | AAC | AAA | GCC | ATT | TTG | GTC | ACT | GGT | GCT | ACT | GGC | TCC | TTA | GCA | AAA | 160 |
|---|---|---|---|---|---|---|---|---|---|---|---|---|---|---|---|---|
| Asp | Asn | Lys | Ala | Ile | Leu | Val | Thr | Gly | Ala | Thr | Gly | Ser | Leu | Ala | Lys | |
| | | | 15 | | | | 20 | | | | | 25 | | | | |

| ATT | TTT | GTG | GAG | AAG | GTA | CTG | AGG | AGT | CAA | CCG | AAT | GTG | AAG | AAA | CTC | 208 |
|---|---|---|---|---|---|---|---|---|---|---|---|---|---|---|---|---|
| Ile | Phe | Val | Glu | Lys | Val | Leu | Arg | Ser | Gln | Pro | Asn | Val | Lys | Lys | Leu | |
| | | 30 | | | | | 35 | | | | | 40 | | | | |

| TAT | CTT | CTT | TTG | AGA | GCA | ACC | GAT | GAC | GAG | ACA | GCT | GCT | CTA | CGC | TTG | 256 |
|---|---|---|---|---|---|---|---|---|---|---|---|---|---|---|---|---|
| Tyr | Leu | Leu | Leu | Arg | Ala | Thr | Asp | Asp | Glu | Thr | Ala | Ala | Leu | Arg | Leu | |
| | | 45 | | | | 50 | | | | | 55 | | | | | |

| CAA | AAT | GAG | GTT | TTT | GGA | AAA | GAG | TTG | TTC | AAA | GTT | CTG | AAA | CAA | AAT | 304 |
|---|---|---|---|---|---|---|---|---|---|---|---|---|---|---|---|---|
| Gln | Asn | Glu | Val | Phe | Gly | Lys | Glu | Leu | Phe | Lys | Val | Leu | Lys | Gln | Asn | |
| 60 | | | | | 65 | | | | | 70 | | | | | 75 | |

| TTA | GGT | GCA | AAT | TTC | TAT | TCC | TTT | GTA | TCA | GAA | AAA | GTG | ACT | GTA | GTA | 352 |
|---|---|---|---|---|---|---|---|---|---|---|---|---|---|---|---|---|
| Leu | Gly | Ala | Asn | Phe | Tyr | Ser | Phe | Val | Ser | Glu | Lys | Val | Thr | Val | Val | |
| | | | | 80 | | | | | 85 | | | | | 90 | | |

| CCC | GGT | GAT | ATT | ACT | GGT | GAA | GAC | TTG | TGT | CTC | AAA | GAC | GTC | AAT | TTG | 400 |
|---|---|---|---|---|---|---|---|---|---|---|---|---|---|---|---|---|
| Pro | Gly | Asp | Ile | Thr | Gly | Glu | Asp | Leu | Cys | Leu | Lys | Asp | Val | Asn | Leu | |
| | | | 95 | | | | | 100 | | | | | 105 | | | |

| AAG | GAA | GAA | ATG | TGG | AGG | GAA | ATC | GAT | GTT | GTT | GTC | AAT | CTA | GCT | GCT | 448 |
|---|---|---|---|---|---|---|---|---|---|---|---|---|---|---|---|---|
| Lys | Glu | Glu | Met | Trp | Arg | Glu | Ile | Asp | Val | Val | Val | Asn | Leu | Ala | Ala | |
| | | 110 | | | | | 115 | | | | | 120 | | | | |

| ACA | ATC | AAC | TTC | ATT | GAA | AGG | TAC | GAC | GTG | TCT | CTG | CTT | ATC | AAC | ACA | 496 |
|---|---|---|---|---|---|---|---|---|---|---|---|---|---|---|---|---|
| Thr | Ile | Asn | Phe | Ile | Glu | Arg | Tyr | Asp | Val | Ser | Leu | Leu | Ile | Asn | Thr | |
| | 125 | | | | | 130 | | | | | 135 | | | | | |

| TAT | GGA | GCC | AAG | TAT | GTT | TTG | GAC | TTC | GCG | AAG | AAG | TGC | AAC | AAA | TTA | 544 |
|---|---|---|---|---|---|---|---|---|---|---|---|---|---|---|---|---|
| Tyr | Gly | Ala | Lys | Tyr | Val | Leu | Asp | Phe | Ala | Lys | Lys | Cys | Asn | Lys | Leu | |
| 140 | | | | 145 | | | | | 150 | | | | | 155 | | |

| AAG | ATA | TTT | GTT | CAT | GTA | TCT | ACT | GCT | TAT | GTA | TCT | GGA | GAG | AAA | AAT | 592 |
|---|---|---|---|---|---|---|---|---|---|---|---|---|---|---|---|---|
| Lys | Ile | Phe | Val | His | Val | Ser | Thr | Ala | Tyr | Val | Ser | Gly | Glu | Lys | Asn | |
| | | | | 160 | | | | 165 | | | | | 170 | | | |

| GGG | TTA | ATA | CTG | GAG | AAG | CCT | TAT | TAT | ATG | GGC | GAG | TCA | CTT | AAT | GGA | 640 |
|---|---|---|---|---|---|---|---|---|---|---|---|---|---|---|---|---|
| Gly | Leu | Ile | Leu | Glu | Lys | Pro | Tyr | Tyr | Met | Gly | Glu | Ser | Leu | Asn | Gly | |
| | | | 175 | | | | | 180 | | | | | 185 | | | |

| AGA | TTA | GGT | CTG | GAC | ATT | AAT | GTA | GAG | AAG | AAA | CTT | GTG | GAG | GCA | AAA | 688 |
|---|---|---|---|---|---|---|---|---|---|---|---|---|---|---|---|---|
| Arg | Leu | Gly | Leu | Asp | Ile | Asn | Val | Glu | Lys | Lys | Leu | Val | Glu | Ala | Lys | |
| | | 190 | | | | | 195 | | | | | 200 | | | | |

| ATC | AAT | GAA | CTT | CAA | GCA | GCG | GGG | GCA | ACG | GAA | AAG | TCC | ATT | AAA | TCG | 736 |
|---|---|---|---|---|---|---|---|---|---|---|---|---|---|---|---|---|
| Ile | Asn | Glu | Leu | Gln | Ala | Ala | Gly | Ala | Thr | Glu | Lys | Ser | Ile | Lys | Ser | |
| 205 | | | | | 210 | | | | | 215 | | | | | | |

| ACA | ATG | AAG | GAC | ATG | GGC | ATC | GAG | AGG | GCA | AGA | CAC | TGG | GGA | TGG | CCA | 784 |
|---|---|---|---|---|---|---|---|---|---|---|---|---|---|---|---|---|
| Thr | Met | Lys | Asp | Met | Gly | Ile | Glu | Arg | Ala | Arg | His | Trp | Gly | Trp | Pro | |
| 220 | | | | 225 | | | | | 230 | | | | | | 235 | |

| AAT | GTG | TAT | GTA | TTC | ACC | AAG | GCA | TTA | GGG | GAG | ATG | CTT | TTG | ATG | CAA | 832 |
|---|---|---|---|---|---|---|---|---|---|---|---|---|---|---|---|---|
| Asn | Val | Tyr | Val | Phe | Thr | Lys | Ala | Leu | Gly | Glu | Met | Leu | Leu | Met | Gln | |
| | | | | 240 | | | | 245 | | | | | 250 | | | |

| TAC | AAA | GGG | GAC | ATT | CCG | CTT | ACT | ATT | ATT | CGT | CCC | ACC | ATC | ATC | ACC | 880 |
|---|---|---|---|---|---|---|---|---|---|---|---|---|---|---|---|---|
| Tyr | Lys | Gly | Asp | Ile | Pro | Leu | Thr | Ile | Ile | Arg | Pro | Thr | Ile | Ile | Thr | |
| | | | 255 | | | | | 260 | | | | | 265 | | | |

```
AGC ACT TTT AAA GAG CCC TTT CCT GGT TGG GTT GAA GGT GTC AGG ACC      928
Ser Thr Phe Lys Glu Pro Phe Pro Gly Trp Val Glu Gly Val Arg Thr
        270             275                 280

ATC GAT AAT GTA CCT GTA TAT TAT GGT AAA GGG AGA TTG AGG TGT ATG      976
Ile Asp Asn Val Pro Val Tyr Tyr Gly Lys Gly Arg Leu Arg Cys Met
        285             290                 295

CTT TGC GGA CCC AGC ACA ATA ATT GAC CTG ATA CCG GCA GAT ATG GTC     1024
Leu Cys Gly Pro Ser Thr Ile Ile Asp Leu Ile Pro Ala Asp Met Val
300             305                 310                 315

GTG AAT GCA ACG ATA GTA GCC ATG GTG GCG CAC GCA AAC CAA AGA TAC     1072
Val Asn Ala Thr Ile Val Ala Met Val Ala His Ala Asn Gln Arg Tyr
                320                 325                 330

GTA GAG CCG GTG ACA TAC CAT GTG GGA TCT TCA GCG GCG AAT CCA ATG     1120
Val Glu Pro Val Thr Tyr His Val Gly Ser Ser Ala Ala Asn Pro Met
            335                 340                 345

AAA CTG AGT GCA TTA CCA GAG ATG GCA CAC CGT TAC TTC ACC AAG AAT     1168
Lys Leu Ser Ala Leu Pro Glu Met Ala His Arg Tyr Phe Thr Lys Asn
        350                 355                 360

CCA TGG ATC AAC CCG GAT CGC AAC CCA GTA CAT GTG GGT CGG GCT ATG     1216
Pro Trp Ile Asn Pro Asp Arg Asn Pro Val His Val Gly Arg Ala Met
        365                 370                 375

GTC TTC TCC TCC TTC TCC ACC TTC CAC CTT TAT CTC ACC CTT AAT TTC     1264
Val Phe Ser Ser Phe Ser Thr Phe His Leu Tyr Leu Thr Leu Asn Phe
380                 385                 390                 395

CTC CTT CCT TTG AAG GTA CTG GAG ATA GCA AAT ACA ATA TTC TGC CAA     1312
Leu Leu Pro Leu Lys Val Leu Glu Ile Ala Asn Thr Ile Phe Cys Gln
                400                 405                 410

TGG TTC AAG GGT AAG TAC ATG GAT CTT AAA AGG AAG ACG AGG TTG TTG     1360
Trp Phe Lys Gly Lys Tyr Met Asp Leu Lys Arg Lys Thr Arg Leu Leu
            415                 420                 425

TTG CGT TTA GTA GAC ATT TAT AAA CCC TAC CTC TTC TTC CAA GGC ATC     1408
Leu Arg Leu Val Asp Ile Tyr Lys Pro Tyr Leu Phe Phe Gln Gly Ile
        430                 435                 440

TTT GAT GAC ATG AAC ACT GAG AAG TTG CGG ATT GCT GCA AAA GAA AGC     1456
Phe Asp Asp Met Asn Thr Glu Lys Leu Arg Ile Ala Ala Lys Glu Ser
445                 450                 455

ATA GTT GAA GCT GAT ATG TTT TAC TTT GAT CCC AGG GCA ATT AAC TGG     1504
Ile Val Glu Ala Asp Met Phe Tyr Phe Asp Pro Arg Ala Ile Asn Trp
460                 465                 470                 475

GAA GAT TAC TTC TTG AAA ACT CAT TTC CCA GGN GTC GTA GAG CAC GTT     1552
Glu Asp Tyr Phe Leu Lys Thr His Phe Pro Gly Val Val Glu His Val
                480                 485                 490

CTT AAC TAAAAGTTAC GGTACGAAAA TGAGAAGATT GGAATGCATG CACCGAAAGN     1608
Leu Asn

NCAACATAAA AGACGTGGTT AAAGTCATGG TCAAAAAGA AATAAAATGC AGTTAGGTTT   1668

GTGTTGCAGT TTTGATTCCT TGTATTGTTA CTTGTACTTT TGATCTTTTT CTTTTTTAAT  1728

GAAATTTCTC TCTTTGTTTT GTGAAAAAAA AAAAAAAAA GAGCTCCTGC AGAAGCTT     1786

( 2 ) INFORMATION FOR SEQ ID NO: 2 :

( i ) SEQUENCE CHARACTERISTICS:
            ( A ) LENGTH: 1733 base pairs
            ( B ) TYPE: nucleic acid
            ( C ) STRANDEDNESS: double
            ( D ) TOPOLOGY: linear ( i i ) MOLECULE TYPE: cDNA to mRNA ( x i ) SEQUENCE DESCRIPTION: SEQ ID NO:2 :

GGAACTCCAT CCCTTCCTCC CTCACTCCTC TCTCTACA ATG AAG GCC AAA ACA ATC    56
                                          Met Lys Ala Lys Thr Ile
```

```
                                             1                      5
ACA  AAC  CCG  GAG  ATC  CAA  GTC  TCC  ACG  ACC  ATG  ACC  ACC  ACG  ACC  ACG    104
Thr  Asn  Pro  Glu  Ile  Gln  Val  Ser  Thr  Thr  Met  Thr  Thr  Thr  Thr  Thr
               10                       15                  20

ACT  ATG  ACC  GCC  ACT  CTC  CCC  AAC  TTC  AAG  TCC  TCC  ATC  AAC  TTA  CAC    152
Thr  Met  Thr  Ala  Thr  Leu  Pro  Asn  Phe  Lys  Ser  Ser  Ile  Asn  Leu  His
          25                       30                       35

CAC  GTC  AAG  CTC  GGC  TAC  CAC  TAC  TTA  ATC  TCC  AAT  GCC  CTC  TTC  CTC    200
His  Val  Lys  Leu  Gly  Tyr  His  Tyr  Leu  Ile  Ser  Asn  Ala  Leu  Phe  Leu
     40                            45                  50

GTA  TTC  ATC  CCC  CTT  TTG  GGC  CTC  GCT  TCG  GCC  CAT  CTC  TCC  TCC  TTC    248
Val  Phe  Ile  Pro  Leu  Leu  Gly  Leu  Ala  Ser  Ala  His  Leu  Ser  Ser  Phe
55                       60                       65                       70

TCG  GCC  CAT  GAC  TTG  TCC  CTG  CTC  TTC  GAC  CTC  CTT  CGC  CGC  AAC  CTC    296
Ser  Ala  His  Asp  Leu  Ser  Leu  Leu  Phe  Asp  Leu  Leu  Arg  Arg  Asn  Leu
               75                       80                       85

CTC  CCT  GTT  GTC  GTT  TGT  TCT  TTC  CTC  TTC  GTT  TTA  TTA  GCA  ACC  CTA    344
Leu  Pro  Val  Val  Val  Cys  Ser  Phe  Leu  Phe  Val  Leu  Leu  Ala  Thr  Leu
          90                       95                       100

CAT  TTC  TTG  ACC  CGG  CCC  AGG  AAT  GTC  TAC  TTG  GTG  GAC  TTT  GGA  TGC    392
His  Phe  Leu  Thr  Arg  Pro  Arg  Asn  Val  Tyr  Leu  Val  Asp  Phe  Gly  Cys
               105                      110                 115

TAT  AAG  CCT  CAA  CCG  AAC  CTG  ATG  ACA  TCC  CAC  GAG  ATG  TTC  ATG  GAC    440
Tyr  Lys  Pro  Gln  Pro  Asn  Leu  Met  Thr  Ser  His  Glu  Met  Phe  Met  Asp
     120                           125                      130

CGG  ACC  TCC  CGG  GCC  GGG  TCG  TTT  TCT  AAG  GAG  AAT  ATT  GAG  TTT  CAG    488
Arg  Thr  Ser  Arg  Ala  Gly  Ser  Phe  Ser  Lys  Glu  Asn  Ile  Glu  Phe  Gln
135                      140                      145                      150

AGG  AAG  ATC  TTG  GAG  AGG  GCC  GGT  ATG  GGT  CGG  GAA  ACC  TAT  GTC  CCC    536
Arg  Lys  Ile  Leu  Glu  Arg  Ala  Gly  Met  Gly  Arg  Glu  Thr  Tyr  Val  Pro
               155                      160                      165

GAA  TCC  GTC  ACT  AAG  GTG  CCC  GCC  GAG  CCG  AGC  ATA  GCA  GCA  GCC  AGG    584
Glu  Ser  Val  Thr  Lys  Val  Pro  Ala  Glu  Pro  Ser  Ile  Ala  Ala  Ala  Arg
               170                      175                      180

GCC  GAG  GCG  GAG  GAG  GTG  ATG  TAC  GGG  GCG  ATC  GAC  GAG  GTG  TTG  GAG    632
Ala  Glu  Ala  Glu  Glu  Val  Met  Tyr  Gly  Ala  Ile  Asp  Glu  Val  Leu  Glu
          185                      190                      195

AAG  ACG  GGG  GTG  AAG  CCG  AAG  CAG  ATA  GGA  ATA  CTG  GTG  GTG  ANC  TGC    680
Lys  Thr  Gly  Val  Lys  Pro  Lys  Gln  Ile  Gly  Ile  Leu  Val  Val  Xxx  Cys
     200                      205                      210

AGC  TTG  TTT  AAC  CCA  ACG  CCG  TCG  CTG  TCA  TCC  ATG  ATA  GTT  AAC  CAT    728
Ser  Leu  Phe  Asn  Pro  Thr  Pro  Ser  Leu  Ser  Ser  Met  Ile  Val  Asn  His
215                      220                      225                      230

TAC  AAG  CTN  AGG  GGT  AAT  ATA  CTT  AGC  TAT  AAT  CTT  GGT  GGC  ATG  GGT    776
Tyr  Lys  Leu  Arg  Gly  Asn  Ile  Leu  Ser  Tyr  Asn  Leu  Gly  Gly  Met  Gly
               235                      240                      245

TGC  AGT  GCT  GGG  CTC  ATT  TCC  ATT  GAT  CTT  GCC  AAG  GAC  CTC  CTA  CAG    824
Cys  Ser  Ala  Gly  Leu  Ile  Ser  Ile  Asp  Leu  Ala  Lys  Asp  Leu  Leu  Gln
               250                      255                      260

GTT  TAC  CGT  AAA  AAC  ACA  TAT  GTG  TTA  GTA  GTG  AGC  ACG  GAA  AAC  ATG    872
Val  Tyr  Arg  Lys  Asn  Thr  Tyr  Val  Leu  Val  Val  Ser  Thr  Glu  Asn  Met
          265                      270                      275

ACC  CTT  AAT  TGG  TAC  TGG  GGC  AAT  GAC  CGC  TCC  ATG  CTT  ATC  ACC  AAC    920
Thr  Leu  Asn  Trp  Tyr  Trp  Gly  Asn  Asp  Arg  Ser  Met  Leu  Ile  Thr  Asn
280                      285                      290

TGC  CTA  TTT  CGC  ATG  GGT  GGC  GCT  GCC  ATC  ATC  CTC  TCA  AAC  CGC  TGG    968
Cys  Leu  Phe  Arg  Met  Gly  Gly  Ala  Ala  Ile  Ile  Leu  Ser  Asn  Arg  Trp
295                      300                      305                      310

CGT  GAT  CGT  CGC  CGA  TCC  AAG  TAC  CAA  CTC  CTT  CAT  ACA  GTA  CGC  ACC   1016
Arg  Asp  Arg  Arg  Arg  Ser  Lys  Tyr  Gln  Leu  Leu  His  Thr  Val  Arg  Thr
```

-continued

|  |  |  | 315 |  |  |  |  | 320 |  |  |  |  | 325 |  |  |  |
|---|---|---|---|---|---|---|---|---|---|---|---|---|---|---|---|---|
| CAC | AAG | GGC | GCT | GAC | GAC | AAG | TCC | TAT | AGA | TGC | GTC | TTA | CAA | CAA | GAA | 1064 |
| His | Lys | Gly | Ala | Asp | Asp | Lys | Ser | Tyr | Arg | Cys | Val | Leu | Gln | Gln | Glu |  |
|  |  |  | 330 |  |  |  |  | 335 |  |  |  |  | 340 |  |  |  |
| GAT | GAA | AAT | AAC | AAG | GTA | GGT | GTT | GCC | TTA | TCC | AAG | GAT | CTG | ATG | GCA | 1112 |
| Asp | Glu | Asn | Asn | Lys | Val | Gly | Val | Ala | Leu | Ser | Lys | Asp | Leu | Met | Ala |  |
|  |  | 345 |  |  |  |  | 350 |  |  |  |  | 355 |  |  |  |  |
| GTT | GCC | GGT | GAA | GCC | CTA | AAG | GCC | AAC | ATC | ACG | ACC | CTT | GGT | CCC | CTC | 1160 |
| Val | Ala | Gly | Glu | Ala | Leu | Lys | Ala | Asn | Ile | Thr | Thr | Leu | Gly | Pro | Leu |  |
| 360 |  |  |  |  | 365 |  |  |  |  | 370 |  |  |  |  |  |  |
| GTG | CTC | CCC | ATG | TCA | GAA | CAA | CTC | CTC | TTC | TTT | GCC | ACC | TTA | GTG | GCA | 1208 |
| Val | Leu | Pro | Met | Ser | Glu | Gln | Leu | Leu | Phe | Phe | Ala | Thr | Leu | Val | Ala |  |
| 375 |  |  |  |  | 380 |  |  |  |  | 385 |  |  |  |  | 390 |  |
| CGT | AAG | GTC | TTC | AAG | ATG | ACG | AAC | GTG | AAG | CCA | TAC | ATC | CCA | GAT | TTC | 1256 |
| Arg | Lys | Val | Phe | Lys | Met | Thr | Asn | Val | Lys | Pro | Tyr | Ile | Pro | Asp | Phe |  |
|  |  |  |  | 395 |  |  |  |  | 400 |  |  |  |  | 405 |  |  |
| AAG | TTG | GCA | GCG | AAC | GAC | TTC | TGC | ATC | CAT | GCA | GGA | GGC | AAA | GCA | GTG | 1304 |
| Lys | Leu | Ala | Ala | Asn | Asp | Phe | Cys | Ile | His | Ala | Gly | Gly | Lys | Ala | Val |  |
|  |  |  | 410 |  |  |  |  | 415 |  |  |  |  | 420 |  |  |  |
| TTG | GAT | GAG | CTC | GAG | AAG | AAC | TTG | GAG | TTG | ACG | CCA | TGG | CAC | CTT | GAA | 1352 |
| Leu | Asp | Glu | Leu | Glu | Lys | Asn | Leu | Glu | Leu | Thr | Pro | Trp | His | Leu | Glu |  |
|  |  | 425 |  |  |  |  | 430 |  |  |  |  | 435 |  |  |  |  |
| CCC | TCG | AGG | ATG | ACA | CTG | TAT | AGG | TTT | GGG | AAC | ACA | TCG | AGT | AGC | TCA | 1400 |
| Pro | Ser | Arg | Met | Thr | Leu | Tyr | Arg | Phe | Gly | Asn | Thr | Ser | Ser | Ser | Ser |  |
|  | 440 |  |  |  |  | 445 |  |  |  |  | 450 |  |  |  |  |  |
| TTA | TGG | TAC | GAG | TTG | GCA | TAC | GCT | GAA | GCA | AAA | GGG | AGG | ATC | CGT | AAG | 1448 |
| Leu | Trp | Tyr | Glu | Leu | Ala | Tyr | Ala | Glu | Ala | Lys | Gly | Arg | Ile | Arg | Lys |  |
| 455 |  |  |  |  | 460 |  |  |  |  | 465 |  |  |  |  | 470 |  |
| GGT | GAT | CGA | ACT | TGG | ATG | ATT | GGA | TTT | GGT | TCA | GGT | TTC | AAG | TGT | AAC | 1496 |
| Gly | Asp | Arg | Thr | Trp | Met | Ile | Gly | Phe | Gly | Ser | Gly | Phe | Lys | Cys | Asn |  |
|  |  |  |  | 475 |  |  |  |  | 480 |  |  |  |  | 485 |  |  |
| AGT | GTT | GTG | TGG | AGG | GCT | TTG | AGG | AGT | GTC | AAT | CCG | GCT | AGA | GAG | AAG | 1544 |
| Ser | Val | Val | Trp | Arg | Ala | Leu | Arg | Ser | Val | Asn | Pro | Ala | Arg | Glu | Lys |  |
|  |  |  | 490 |  |  |  |  | 495 |  |  |  |  | 500 |  |  |  |
| AAT | CCT | TGG | ATG | GAT | GAA | ATT | GAG | AAG | TTC | CCT | GTC | CAT | GTG | CCT | AAA | 1592 |
| Asn | Pro | Trp | Met | Asp | Glu | Ile | Glu | Lys | Phe | Pro | Val | His | Val | Pro | Lys |  |
|  |  | 505 |  |  |  |  | 510 |  |  |  |  | 515 |  |  |  |  |
| ATC | GCA | CCT | ATC | GCT | TCG | TAGAACTGCT | AGGATGTGAT | TAGTAATGAA |  |  |  |  |  |  |  | 1640 |
| Ile | Ala | Pro | Ile | Ala | Ser |  |  |  |  |  |  |  |  |  |  |  |
|  |  | 520 |  |  |  |  |  |  |  |  |  |  |  |  |  |  |

AAATGTGTAT TATGTTAGTG ATGTAGAAAA AGAAACTTTA GTTGATGGGT GAGAACATGT 1700

CTCATTGAGA ATAACGTGTG CATCGTTGTG TTG 1733

( 2 ) INFORMATION FOR SEQ ID NO:3 :

( i ) SEQUENCE CHARACTERISTICS:
        ( A ) LENGTH: 1783 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:3 :

| GTCGACACA | ATG | AAG | GCC | AAA | ACA | ATC | ACA | AAC | CCG | GAG | ATC | CAA | GTC | TCC | 51 |
|---|---|---|---|---|---|---|---|---|---|---|---|---|---|---|---|
|  | Met | Lys | Ala | Lys | Thr | Ile | Thr | Asn | Pro | Glu | Ile | Gln | Val | Ser |  |
|  | 1 |  |  |  | 5 |  |  |  |  | 10 |  |  |  |  |  |
| ACG | ACC | ATG | ACC | ACC | ACG | ACC | ACG | ACC | GCC | ACT | CTC | CCC | AAC | TTC | AAG | 99 |
| Thr | Thr | Met | Thr | Thr | Thr | Thr | Thr | Thr | Ala | Thr | Leu | Pro | Asn | Phe | Lys |  |
| 15 |  |  |  | 20 |  |  |  |  | 25 |  |  |  |  | 30 |  |  |
| TCC | TCC | ATC | AAC | TTA | CAC | CAC | GTC | AAG | CTC | GGC | TAC | CAC | TAC | TTA | ATC | 147 |

-continued

| | | | | | | | | | | | | | | | | |
|---|---|---|---|---|---|---|---|---|---|---|---|---|---|---|---|---|
| Ser | Ser | Ile | Asn | Leu<br>35 | His | His | Val | Lys | Leu<br>40 | Gly | Tyr | His | Tyr | Leu<br>45 | Ile | |
| TCC | AAT | GCC | CTC | TTC | CTC | GTA | TTC | ATC | CCC | CTT | TTG | GGC | CTC | GCT | TCG | 195 |
| Ser | Asn | Ala | Leu<br>50 | Phe | Leu | Val | Phe | Ile<br>55 | Pro | Leu | Leu | Gly | Leu<br>60 | Ala | Ser | |
| GCC | CAC | CTC | TCC | TCC | TTC | TCG | GCC | CAT | GAC | TTG | TCC | CTG | CTC | TTC | GAC | 243 |
| Ala | His | Leu<br>65 | Ser | Ser | Phe | Ser | Ala | His<br>70 | Asp | Leu | Ser | Leu<br>75 | Leu | Phe | Asp | |
| CTC | CTT | CGC | CGC | AAC | CTC | CTC | CCC | GTT | GTC | GTT | TGT | TCT | TTC | CTC | TTC | 291 |
| Leu | Leu<br>80 | Arg | Arg | Asn | Leu | Leu<br>85 | Pro | Val | Val | Val | Cys<br>90 | Ser | Phe | Leu | Phe | |
| GTT | TTA | TTA | GCA | ACC | CTA | CAT | TTC | TTG | ACC | CGG | CCT | AGG | AAT | GTC | TAC | 339 |
| Val<br>95 | Leu | Leu | Ala | Thr | Leu<br>100 | His | Phe | Leu | Thr | Arg<br>105 | Pro | Arg | Asn | Val | Tyr<br>110 | |
| TTG | GTG | GAC | TTT | GCC | TGC | TAT | AAG | CCT | CAC | CCG | AAC | CTG | ATA | ACA | TCC | 387 |
| Leu | Val | Asp | Phe | Ala<br>115 | Cys | Tyr | Lys | Pro | His<br>120 | Pro | Asn | Leu | Ile | Thr<br>125 | Ser | |
| CAC | GAG | ATG | TTC | ATG | GAC | CGG | ACC | TCC | CGG | GCC | GGG | TCG | TTT | TCT | AAG | 435 |
| His | Glu | Met | Phe<br>130 | Met | Asp | Arg | Thr | Ser<br>135 | Arg | Ala | Gly | Ser | Phe<br>140 | Ser | Lys | |
| GAG | AAT | ATT | GAG | TTT | CAG | AGG | AAG | ATC | TTG | GAG | AGG | GCC | GGT | ATG | GGC | 483 |
| Glu | Asn | Ile<br>145 | Glu | Phe | Gln | Arg | Lys<br>150 | Ile | Leu | Glu | Arg | Ala<br>155 | Gly | Met | Gly | |
| CGG | GAA | ACC | TAC | GTC | CCC | GAA | TCC | GTC | ACT | AAG | GTG | CCG | CCC | GAG | CCG | 531 |
| Arg | Glu<br>160 | Thr | Tyr | Val | Pro | Glu<br>165 | Ser | Val | Thr | Lys | Val<br>170 | Pro | Pro | Glu | Pro | |
| AGC | ATA | GCA | GCA | GCC | AGG | GCC | GAG | GCG | GAG | GAG | GTG | ATG | TAC | GGG | GCG | 579 |
| Ser<br>175 | Ile | Ala | Ala | Ala | Arg<br>180 | Ala | Glu | Ala | Glu | Glu<br>185 | Val | Met | Tyr | Gly | Ala<br>190 | |
| ATC | GAC | GAG | GTG | TTG | GAG | AAG | ACG | GGG | GTG | AAG | CCG | AAG | CAG | ATA | GGA | 627 |
| Ile | Asp | Glu | Val | Leu<br>195 | Glu | Lys | Thr | Gly | Val<br>200 | Lys | Pro | Lys | Gln | Ile<br>205 | Gly | |
| ATA | CTG | GTG | GTG | AAC | TGC | AGC | TTG | TTT | AAC | CCA | ACG | CCG | TCG | CTG | TCA | 675 |
| Ile | Leu | Val | Val<br>210 | Asn | Cys | Ser | Leu | Phe<br>215 | Asn | Pro | Thr | Pro | Ser<br>220 | Leu | Ser | |
| TCC | ATG | ATA | GTT | AAC | CAT | TAC | AAG | CTT | AGG | GGT | AAT | ATA | CTT | AGC | TAT | 723 |
| Ser | Met | Ile<br>225 | Val | Asn | His | Tyr | Lys<br>230 | Leu | Arg | Gly | Asn | Ile<br>235 | Leu | Ser | Tyr | |
| AAT | CTT | GGT | GGC | ATG | GGT | TGC | AGT | GCT | GGG | CTC | ATT | TCC | ATT | GAT | CTT | 771 |
| Asn | Leu<br>240 | Gly | Gly | Met | Gly | Cys<br>245 | Ser | Ala | Gly | Leu | Ile<br>250 | Ser | Ile | Asp | Leu | |
| GCC | AAG | GAC | CTC | CTA | CAG | GTT | TAC | CGT | AAC | ACA | TAT | GTG | TTA | GTA | GTG | 819 |
| Ala | Lys<br>255 | Asp | Leu | Leu | Gln | Val<br>260 | Tyr | Arg | Asn | Thr | Tyr<br>265 | Val | Leu | Val | Val<br>270 | |
| AGC | ACA | GAA | AAC | ATG | ACC | CTT | AAT | TGG | TAC | TGG | GGC | AAT | GAC | CGC | TCC | 867 |
| Ser | Thr | Glu | Asn | Met<br>275 | Thr | Leu | Asn | Trp | Tyr<br>280 | Trp | Gly | Asn | Asp | Arg<br>285 | Ser | |
| ATG | CTT | ATC | ACC | AAC | TGC | CTA | TTT | CGC | ATG | GGT | GGC | GCT | GCC | ATC | ATC | 915 |
| Met | Leu | Ile | Thr | Asn<br>290 | Cys | Leu | Phe | Arg | Met<br>295 | Gly | Gly | Ala | Ala | Ile<br>300 | Ile | |
| CTC | TCA | AAC | CGC | TGG | CGT | GAT | CGT | CGC | CGA | TCC | AAG | TAC | CAA | CTC | CTT | 963 |
| Leu | Ser | Asn<br>305 | Arg | Trp | Arg | Asp | Arg<br>310 | Arg | Arg | Ser | Lys | Tyr<br>315 | Gln | Leu | Leu | |
| CAC | ACA | GTA | CGC | ACC | CAC | AAG | GGC | GCT | GAC | GAC | AAG | TCC | TAT | AGA | TGC | 1011 |
| His | Thr | Val<br>320 | Arg | Thr | His | Lys<br>325 | Gly | Ala | Asp | Asp | Lys<br>330 | Ser | Tyr | Arg | Cys | |
| GTC | TTA | CAA | CAA | GAA | GAT | GAA | AAT | AAC | AAG | GTA | GGT | GTT | GCC | TTA | TCC | 1059 |
| Val | Leu<br>335 | Gln | Gln | Glu | Asp | Glu<br>340 | Asn | Asn | Lys | Val<br>345 | Gly | Val | Ala | Leu | Ser<br>350 | |
| AAG | GAT | CTG | ATG | GCA | GTT | GCC | GGT | GAA | GCC | CTA | AAG | GCC | AAC | ATC | ACG | 1107 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Lys | Asp | Leu | Met | Ala | Val | Ala | Gly | Glu | Ala | Leu | Lys | Ala | Asn | Ile | Thr |      |
|     |     |     |     | 355 |     |     |     | 360 |     |     |     |     |     | 365 |     |      |
| ACC | CTT | GGT | CCC | CTC | GTG | CTC | CCC | ATG | TCA | GAA | CAA | CTC | CTC | TTC | TTT | 1155 |
| Thr | Leu | Gly | Pro | Leu | Val | Leu | Pro | Met | Ser | Glu | Gln | Leu | Leu | Phe | Phe |      |
|     |     |     | 370 |     |     |     |     | 375 |     |     |     |     | 380 |     |     |      |
| GCC | ACC | TTA | GTG | GCA | CGT | AAG | GTC | TTC | AAG | ATG | ACG | AAC | GTG | AAG | CCA | 1203 |
| Ala | Thr | Leu | Val | Ala | Arg | Lys | Val | Phe | Lys | Met | Thr | Asn | Val | Lys | Pro |      |
|     |     | 385 |     |     |     |     | 390 |     |     |     |     | 395 |     |     |     |      |
| TAC | ATC | CCA | GAT | TTC | AAG | TTG | GCA | GCG | AAG | CAC | TTC | TGC | ATC | CAT | GCA | 1251 |
| Tyr | Ile | Pro | Asp | Phe | Lys | Leu | Ala | Ala | Lys | His | Phe | Cys | Ile | His | Ala |      |
|     | 400 |     |     |     |     | 405 |     |     |     |     | 410 |     |     |     |     |      |
| GGA | GGC | AAA | GCA | GTG | TTG | GAT | GAG | CTC | GAG | ACG | AAC | TTG | GAG | TTG | ACG | 1299 |
| Gly | Gly | Lys | Ala | Val | Leu | Asp | Glu | Leu | Glu | Thr | Asn | Leu | Glu | Leu | Thr |      |
| 415 |     |     |     | 420 |     |     |     |     | 425 |     |     |     |     | 430 |     |      |
| CCA | TGG | CAC | CTT | GAA | CCC | TCG | AGG | ATG | ACA | CTG | TAT | AGG | TTT | GGG | AAC | 1347 |
| Pro | Trp | His | Leu | Glu | Pro | Ser | Arg | Met | Thr | Leu | Tyr | Arg | Phe | Gly | Asn |      |
|     |     |     |     | 435 |     |     |     |     | 440 |     |     |     |     | 445 |     |      |
| ACA | TCG | AGT | AGC | TCA | TTA | TGG | TAC | GAG | TTG | GCA | TAC | GCT | GAA | GCA | AAA | 1395 |
| Thr | Ser | Ser | Ser | Ser | Leu | Trp | Tyr | Glu | Leu | Ala | Tyr | Ala | Glu | Ala | Lys |      |
|     |     |     | 450 |     |     |     |     | 455 |     |     |     |     | 460 |     |     |      |
| GGG | AGG | ATC | CGT | AAG | GGT | GAT | CGA | ACT | TGG | ATG | ATT | GGA | TTT | GGT | TCA | 1443 |
| Gly | Arg | Ile | Arg | Lys | Gly | Asp | Arg | Thr | Trp | Met | Ile | Gly | Phe | Gly | Ser |      |
|     |     | 465 |     |     |     |     | 470 |     |     |     |     | 475 |     |     |     |      |
| GGT | TTC | AAG | TGT | AAC | AGT | GTT | GTG | TGG | AGG | GCT | TTG | AGG | AGT | GTC | AAT | 1491 |
| Gly | Phe | Lys | Cys | Asn | Ser | Val | Val | Trp | Arg | Ala | Leu | Arg | Ser | Val | Asn |      |
|     |     | 480 |     |     |     | 485 |     |     |     |     | 490 |     |     |     |     |      |
| CCG | GCT | AGA | GAG | AAG | AAT | CCT | TGG | ATG | GAT | GAA | ATT | GAG | AAT | TTC | CCT | 1539 |
| Pro | Ala | Arg | Glu | Lys | Asn | Pro | Trp | Met | Asp | Glu | Ile | Glu | Asn | Phe | Pro |      |
| 495 |     |     |     |     | 500 |     |     |     |     | 505 |     |     |     |     | 510 |      |
| GTC | CAT | GTG | CCT | AAA | ATC | GCA | CCT | ATC | GCT | TCG | TAGAACTGCT | | AGGATGTGAT | | | 1592 |
| Val | His | Val | Pro | Lys | Ile | Ala | Pro | Ile | Ala | Ser |     |     |     |     |     |      |
|     |     |     |     | 515 |     |     |     |     | 520 |     |     |     |     |     |     |      |

```
TAGTAATGAA AAATGTGTAT TATGTTAGTG ATGTAGAAAA AGAAACTTTA GTTGATGGGT     1652

GAGAACATGT CTCATTGAGA ATAACGTGTG CATCGTTGTG TTGAATTTGA ATTGAGTAT      1712

TGGTGAAATT CTGTTAGAAT TGACGCATGA GTCATATATA TACAAATTTA AGTAAGATTT     1772

TACGCTTTCT T                                                          1783
```

(2) INFORMATION FOR SEQ ID NO: 4:

(i) SEQUENCE CHARACTERISTICS:
        (A) LENGTH: 1647 base pairs
        (B) TYPE: nucleic acid
        (C) STRANDEDNESS: double
        (D) TOPOLOGY: linear (ii) MOLECULE TYPE: other nucleic acid
        (A) DESCRIPTION: PCR to genomic DNA (xi) SEQUENCE DESCRIPTION: SEQ ID NO:4 :

```
GGCGCGCCGG TACCTCTAGA CCTGGCGATT CAACGTGGTC GGATCATGAC GCTTCCAGAA     60

AACATCGAGC AAGCTCTCAA AGCTGACCTC TTTCGGATCG TACTGAACCC GAACAATCTC    120

GTTATGTCCC GTCGTCTCCG AACAGACATC CTCGTAGCTC GGATTATCGA CGAATCCATG    180

GCTATACCCA ACCTCCGTCT TCGTCACGCC TGGAACCCTC TGGTACGCCA ATTCCGCTCC    240

CCAGAAGCAA CCGGCGCCGA ATTGCGCGAA TTGCTGACCT GGAGACGGAA CATCGTCGTC    300

GGGTCCTTGC GCGATTGCGG CGGAAGCCGG GTCGGGTTGG GGACGAGACC GAATCCGAG     360

CCTGGTGAAG AGGTTGTTCA TCGGAGATTT ATAGACGGAG ATGGATCGAG CGGTTTTGGG    420

GAAAGGGGAA GTGGGTTTGG CTCTTTTGGA TAGAGAGAGT GCAGCTTTGG AGAGAGACTG    480
```

-continued

```
GAGAGGTTTA GAGAGAGACG CGGCGGATAT TACCGGAGGA GAGGCGACGA GAGATAGCAT      540
TATCGAAGGG GAGGGAGAAA GAGTGACGTG GAGAAATAAG AAACCGTTAA GAGTCGGATA      600
TTTATCATAT TAAAAGCCCA ATGGGCCTGA ACCCATTTAA ACAAGACAGA TAAATGGGCC      660
GTGTGTTAAG TTAACAGAGT GTTAACGTTC GGTTTCAAAT GCCAACGCCA TAGGAACAAA      720
ACAAACGTGT CCTCAAGTAA ACCCCTGCCG TTTACACCTC AATGGCTGCA TGGTGAAGCC      780
ATTAACACGT GGCGTAGGAT GCATGACGAC GCCATTGACA CCTGACTCTC TTCCCTTCTC      840
TTCATATATC TCTAATCAAT TCAACTACTC ATTGTCATAG CTATTCGGAA AATACATACA      900
CATCCTTTTC TCTTCGATCT CTCTCAATTC ACAAGAAGCA AGTCGACGG ATCCCTGCAG       960
TAAATTACGC CATGACTATT TCATAGTCC AATAAGGCTG ATGTCGGGAG TCCAGTTTAT      1020
GAGCAATAAG GTGTTTAGAA TTTGATCAAT GTTATAATA AAAGGGGGAA GATGATATCA      1080
CAGTCTTTTG TTCTTTTGG CTTTTGTTAA ATTTGTGTGT TTCTATTTGT AAACCTCCTG      1140
TATATGTTGT ACTTCTTTCC CTTTTTAAGT GGTATCGTCT ATATGGTAAA ACGTTATGTT      1200
TGGTCTTTCC TTTTCTCTGT TTAGGATAAA AAGACTGCAT GTTTTATCTT TAGTTATATT     1260
ATGTTGAGTA AATGAACTTT CATAGATCTG GTTCCGTAGA GTAGACTAGC AGCCGAGCTG     1320
AGCTGAACTG AACAGCTGGC AATGTGAACA CTGGATGCAA GATCAGATGT GAAGATCTCT     1380
AATATGGTGG TGGGATTGAA CATATCGTGT CTATATTTTT GTTGGCATTA AGCTCTTAAC     1440
ATAGATATAA CTGATGCAGT CATTGGTTCA TACACATATA TAGTAAGGAA TTACAATGGC     1500
AACCCAAACT TCAAAAACAG TAGGCCACCT GAATTGCCTT ATCGAATAAG AGTTTGTTTC     1560
CCCCCACTTC ATGGGATGTA ATACATGGGA TTTGGGAGTT TGAATGAACG TTGAGACATG     1620
GCAGAACCTC TAGAGGTACC GGCGCGC                                         1647
```

( 2 ) INFORMATION FOR SEQ ID NO: 5:

( i ) SEQUENCE CHARACTERISTICS:
( A ) LENGTH: 11 residues
( B ) TYPE: amino acids
( D ) TOPOLOGY: linear ( i i ) MOLECULE TYPE: peptide ( x i ) SEQUENCE DESCRIPTION: SEQ ID NO:5 :

Glu Thr Tyr Val Pro Glu Ser Val Thr Lys Lys
                5                   10

( 2 ) INFORMATION FOR SEQ ID NO: 6:

( i ) SEQUENCE CHARACTERISTICS:
( A ) LENGTH: 10 residues
( B ) TYPE: amino acids
( D ) TOPOLOGY: linear ( i i ) MOLECULE TYPE: peptide ( x i ) SEQUENCE DESCRIPTION: SEQ ID NO:6 :

Val Pro Xaa Glu Pro Ser Ile Ala Ala Xaa
                5                   10

( 2 ) INFORMATION FOR SEQ ID NO: 7:

( i ) SEQUENCE CHARACTERISTICS:
( A ) LENGTH: 10 residues
( B ) TYPE: amino acids
( D ) TOPOLOGY: linear ( i i ) MOLECULE TYPE: peptide ( x i ) SEQUENCE DESCRIPTION: SEQ ID NO:7 :

Glu Thr Tyr Val Pro Glu Glu Val Thr Lys
                5                      10

( 2 ) INFORMATION FOR SEQ ID NO: 8:

( i ) SEQUENCE CHARACTERISTICS:
        ( A ) LENGTH: 11 residues
        ( B ) TYPE: amino acids
        ( D ) TOPOLOGY: linear ( i i ) MOLECULE TYPE: peptide ( x i ) SEQUENCE DESCRIPTION: SEQ ID NO:8 :

Asp Leu Met Ala Val Ala Gly Glu Ala Leu Lys
                5                      10

( 2 ) INFORMATION FOR SEQ ID NO: 9:

( i ) SEQUENCE CHARACTERISTICS:
        ( A ) LENGTH: 11 residues
        ( B ) TYPE: amino acids
        ( D ) TOPOLOGY: linear ( i i ) MOLECULE TYPE: peptide ( x i ) SEQUENCE DESCRIPTION: SEQ ID NO:9 :

Met Thr Asn Val Lys Pro Tyr Ile Pro Asp Phe
                5                      10

( 2 ) INFORMATION FOR SEQ ID NO: 10:

( i ) SEQUENCE CHARACTERISTICS:
        ( A ) LENGTH: 11 residues
        ( B ) TYPE: amino acids
        ( D ) TOPOLOGY: linear ( i i ) MOLECULE TYPE: peptide ( x i ) SEQUENCE DESCRIPTION: SEQ ID NO:10 :

Phe Leu Pro Xaa Xaa Val Ala Ile Thr Gly Glu
                5                      10

( 2 ) INFORMATION FOR SEQ ID NO: 11:

( i ) SEQUENCE CHARACTERISTICS:
        ( A ) LENGTH: 17 residues
        ( B ) TYPE: amino acid
        ( D ) TOPOLOGY: linear ( i i ) MOLECULE TYPE: peptide ( x i ) SEQUENCE DESCRIPTION: SEQ ID NO: 11 :

Phe Gly Asn Thr Ser Ser Xaa Xaa Leu Tyr Xaa Glu Leu Ala Tyr Ala
                5                      10                     15
Lys ( 2 ) INFORMATION FOR SEQ ID NO: 12:

( i ) SEQUENCE CHARACTERISTICS:
        ( A ) LENGTH: 17 residues
        ( B ) TYPE: amino acids
        ( D ) TOPOLOGY: linear ( i i ) MOLECULE TYPE: peptide ( x i ) SEQUENCE DESCRIPTION: SEQ ID NO:12 :

-continued

```
Ala Glu Ala Glu Glu Val Met Tyr Gly Ala Ile Asp Glu Val Leu Glu
                 5                   10                  15

Lys
```

( 2 ) INFORMATION FOR SEQ ID NO: 13:

( i ) SEQUENCE CHARACTERISTICS:
        ( A ) LENGTH: 23 residues
        ( B ) TYPE: amino acid
        ( D ) TOPOLOGY: linear ( i i ) MOLECULE TYPE: peptide ( x i ) SEQUENCE DESCRIPTION: SEQ ID NO:13 :

```
Xaa Asp Ile Ala Ile Ile Gly Ser Gly Ser Ala Gly Leu Ala Gln Ala
                 5                   10                  15

Xaa Ile Leu Lys Asp Ala Gly
             20
```

( 2 ) INFORMATION FOR SEQ ID NO: 14:

( i ) SEQUENCE CHARACTERISTICS:
        ( A ) LENGTH:13 residues
        ( B ) TYPE: amino acids
        ( D ) TOPOLOGY: linear ( i i ) MOLECULE TYPE: peptide ( x i ) SEQUENCE DESCRIPTION: SEQ ID NO:14 :

```
Gln Gln Phe Thr Val Trp Xaa Asn Ala Ser Glu Pro Ser
                 5                   10
```

( 2 ) INFORMATION FOR SEQ ID NO: 15:

( i ) SEQUENCE CHARACTERISTICS:
        ( A ) LENGTH:17 base pairs
        ( B ) TYPE: nucleic acid
        ( C ) STRANDEDNESS: single
        ( D ) TOPOLOGY: linear ( i i ) MOLECULE TYPE: other
        ( A ) DESCRIPTION: synthetic oligonucleotide ( x i ) SEQUENCE DESCRIPTION: SEQ ID NO:15 :

AAYATHACNA CNYTNGG                    17

( 2 ) INFORMATION FOR SEQ ID NO: 16:

( i ) SEQUENCE CHARACTERISTICS:
        ( A ) LENGTH: 17 base pairs
        ( B ) TYPE: nucleic acid
        ( C ) STRANDEDNESS:single
        ( D ) TOPOLOGY: linear ( i i ) MOLECULE TYPE: other
        ( A ) DESCRIPTION: synthetic oligonucleotide ( x i ) SEQUENCE DESCRIPTION: SEQ ID NO:16 :

SWRTTRCAYT TRAANCC                    17

NUCLEIC ACID SEQUENCES ENCODING A PLANT CYTOPLASMIC PROTEIN INVOLVED IN FATTY ACYL-COA METABOLISM

This application is a continuation-in-part of U.S. Ser. No. 07/796,256, filed Nov. 20, 1991 (abandoned), a continuation-in-part of U.S. Ser. No. 07/933,411, filed Aug. 21, 1992 (abandoned), a continuation-in-part of PCT/US92/09863, filed Nov. 13, 1992, a continuation-in-part U.S. Ser. No. 08/066,299, filed May 20, 1993 (U.S. Pat. No. 5,445,947) and a continuation-in-part of U.S. Ser. No. 08/160,602, filed Nov. 30, 1993 (abandoned).

TECHNICAL FIELD

The present invention is directed to enzymes, methods to purify, and obtain such enzymes, amino acid and nucleic acid sequences related thereto, and methods of use for such compositions in genetic engineering applications.

INTRODUCTION

1. Background

Through the development of plant genetic engineering techniques, it is possible to transform and regenerate a variety of plant species to provide plants which have novel and desirable characteristics. One area of interest for such plant genetic engineering techniques is the production of valuable products in plant tissues. Such applications require the use of various DNA constructs and nucleic acid sequences for use in transformation events to generate plants which produce the desired product. For example, plant functional promoters are required for appropriate expression of gene sequences, such expression being either in the whole plant or in selected plant tissues. In addition, selective marker sequences are often used to identify the transformed plant material. Such plant promoters and selectable markers provide valuable tools which are useful in obtaining the novel plants.

One desirable goal, which involves such genetic engineering techniques, is the ability to provide crop plants having a convenient source of wax esters. Wax esters are required in a variety of industrial applications, including pharmaceuticals, cosmetics, detergents, plastics, and lubricants. Such products, especially long chain wax esters, have previously been available from the sperm whale, an endangered species, or more recently, from the desert shrub, jojoba. Neither of these sources provides a convenient supply of wax esters.

Jojoba is also a plant which synthesizes very long chain fatty acids (VLCFA) in its seed oil. VLCFA are fatty acids having chain lengths longer than 18 carbons. VLCFA are found in the cuticular "waxes" of many plant species as well as in the seed oil of several plant species. Wild type Brassica plants contain VLCFA in their seed oil. Canola is rapeseed that has been bred to eliminate VLCFA from its seed oil. Enzymes involved in the elongation of fatty acids to VLCFA ("elongase" enzymes) have been difficult to characterize at a biochemical level because they are membrane associated (Harwood, JL, "Fatty acid metabolism", *Annual rev. of Plant Physiol. and Plant Mol. Biol.* (1988) 39:101-38); (von Wettstein-Knowles, PM, "Waxes, cutin, and suberin" in ed. Moore, TS, *Lipid Metabolism in Plants* (1993), CRC Press, Ann Arbor, pp. 127-166). Although several groups have claimed to partially purify some of these elongase enzymes, to date no one has claimed complete purification of one of these enzymes or cloning of the corresponding genes. von Wettstein-Knowles, PM, (1993) supra; van de Loo, FJ, Fox, BG, and Somerville C. "Unusual fatty acids" in ed. Moore, TS, *Lipid Metabolism in Plants*, (1993) CRC Press Ann Arbor, pp. 91-126.

A possible mechanism for fatty acid elongation by the cytoplasmic elongase enzyme system is through a series similar to that found for chloroplast fatty acid synthesis, i.e. via a 4 step reaction (Stumpf and Pollard (1983) supra; van de Loo et al (1993) supra). The first step would be a condensation reaction between malonyl CoA and oleyl CoA by β-ketoacyl-CoA synthase. Then β-ketoacyl-CoA reductase, β-hydroxyacyl-CoA dehydratase, and enoyl-CoA reductase ensymes would act sequentially to generate an acyl-CoA molecule elongated by two carbon atoms.

In order to obtain a reliable source of very long chain fatty acid molecules, such as wax esters or VLCFA, transformation of crop plants, which are easily manipulated in terms of growth, harvest and extraction of products, is desirable. In order to obtain such transformed plants, however, the genes responsible for the biosynthesis of the desired VLCFA or wax ester products must first be obtained.

Wax ester production results from the action of at least two enzymatic activities of fatty acyl CoA metabolism; fatty acyl reductase and fatty acyl:fatty alcohol acyltransferase, or wax synthase. Preliminary studies with such enzymes and extensive analysis and purification of a fatty acyl reductase, indicate that these proteins are associated with membranes, however the enzyme responsible for the fatty acyl:fatty alcohol ligation reaction in wax biosynthesis has not been well characterized. Thus, further study and ultimately, purification of this enzyme is needed so that the gene sequences which encode the enzymatic activity may be obtained.

It is desirable, therefore, to devise a purification protocol whereby the wax synthase protein may be obtained and the amino acid sequence determined and/or antibodies specific for the wax synthase obtained. In this manner, library screening, polymerase chain reaction (PCR) or immunological techniques may be used to identify clones expressing a wax synthase protein. Clones obtained in this manner can be analyzed so that the nucleic acid sequences corresponding to wax synthase activity are identified. The wax synthase nucleic acid sequences may then be utilized in conjunction with fatty acyl reductase proteins, either native to the transgenic host cells or supplied by recombinant techniques, for production of wax esters in host cells.

It would also be desirable to have a gene to an enzyme involved in the formation of very long chain fatty acids. Such a gene could be used to increase the chain length of fatty acids in oilseeds by overexpression of the gene in transgenic plants of virtually any species. The gene could also be used as a probe in low stringency hybridization to isolate homologous clones from other species as a means to clone the gene from other taxa, such as Brassica, Arabidopsis, Crambe, Nasturtium, and Limnanthes, that produce VLCFA. These derived genes could then be used in antisense experiments to reduce the level of VLCFA in the species from which they were isolated, or overexpressed to increase the quantity of VLCFA in transgenic plants of virtually any species. Additionally, the DNA from the homologous Brassica gene encoding this enzyme could be used as a plant breeding tool to develop molecular markers to aid in breeding high erucic acid rapeseed (HEAR) and canola and other oilseed crops. Such techniques would include using the gene itself as a molecular probe or using the DNA sequence to design PCR primers to use PCR based screening techniques in plant breeding programs. Finally, overexpression of the gene in plant epidermal cells could increase cuticle accumulation thereby increasing drought and stress tolerance of transgenic plants over control plants.

2. Relevant Literature

Cell-free homogenates from developing jojoba embryos were reported to have acyl-CoA fatty alcohol acyl transferase activity. The activity was associated with a floating wax pad which formed upon differential centrifugation (Pollard et al. (1979) supra; Wu et al. (1981) supra).

Solubilization of a multienzyme complex from *Euglena gracilis* having fatty acyl-SCoA transacylase activity is reported by Wildner and Hallick (Abstract from *The Southwest Consortium Fifth Annual Meeting*, Apr. 22–24, 1990, Las Cruces, N. Mex.).

Ten-fold purification of jojoba acyl-CoA: alcohol transacylase protein is reported by Pushnik et al. (Abstract from *The Southwest Consortium Fourth Annual Meeting*, Feb. 7, 1989, Riverside, Calif.).

An assay for jojoba acyl-CoA:alcohol transacylase activity was reported by Garver et al. (*Analytical Biochemistry* (1992) 207:335–340).

Extracts of developing seeds from HEAR and canola plants were found to differ in their ability to elongate oleyl CoA into VLCFA, with HEAR extracts capable of catalyzing elongation, while canola extracts were not. Stumpf, PK and Pollard MR, "Pathways of fatty acid biosynthesis in higher plants with particular reference to developing rapeseed", in *High and Low Erucic Acid Rapeseed Oils* (1983) Academic Press Canada, pp. 131–141.

BRIEF DESCRIPTION OF THE DRAWINGS

FIG. 1. The nucleic acid sequence and translated amino acid sequence of a jojoba fatty acyl reductase (SEQ ID NO:1), as determined from the cDNA sequence, is provided in FIG. 1.

FIG. 2. Preliminary nucleic acid sequence and translated amino acid sequence of a jojoba plant cytoplasmic protein involved in fatty acyl-CoA metabolism cDNA clone (SEQ ID NO:2), are provided.

FIG. 3. Nucleic acid and translated amino acid sequences of second class of the jojoba clones, as represented by the sequence of pCGN7614 (SEQ ID NO:3), is provided.

FIG. 4. Nucleic acid sequence of an oleosin expression cassette (SEQ ID NO:4) is provided.

SUMMARY OF THE INVENTION

By this invention, a DNA sequence encoding a plant cytoplasmic protein involved in fatty acyl-CoA metabolism is provided. Such a sequence is desirable for use in methods aimed at altering the composition of very long chain wax fatty acid related products, such as wax esters and very long chain fatty acids in host cells In one aspect, the protein of this invention may demonstrate fatty acyl-CoA: fatty alcohol O-acyltransferase activity, such activity being referred to herein as "wax synthase".

In a second aspect, this protein may be required for elongation reactions involved in the formation of very long chain fatty acids. Thus, for example, the protein provides for elongation of C18 fatty acyl CoA molecules to form C20 fatty acids, and also for elongation of C20 fatty acids to form even longer chain fatty acids. It is likely that the elongase activity is the result of β-ketoacyl-CoA synthase activity of this protein, although the possibility exists that the protein provided herein has a regulatory function required for the expression of a β-ketoacyl-CoA synthase or provides one of the other activities known to be involved in acyl-CoA elongation, such as β-ketoacyl-CoA reductase, β-hydroxyacyl-CoA dehydratase, or enoyl-CoA reductase activities. In any event, the fatty acyl CoA elongation aspect of this protein is referred to herein as "elongase" activity.

The DNA sequence of this invention is exemplified by sequences obtained from a jojoba embryo cDNA library. Several related jojoba sequences have been discovered and are provided in FIGS. 2 and 3 herein.

In a different aspect of this invention, nucleic acid sequences associated with other proteins related to the exemplified plant cytoplasmic protein involved in fatty acyl-CoA metabolism are considered. Methods are described whereby such sequences may be identified and obtained from the amino acid sequences and nucleic acid sequences of this invention. Uses of the structural gene sequences for isolation of sequences encoding similar cytoplasmic proteins involved in fatty acyl-CoA metabolism from other plant species, as well as in recombinant constructs for transcription and/or expression in host cells of the protein encoded by such sequences are described. Uses of other nucleic acid sequences associated with the protein encoding sequences are also considered, such as the use of 5' and 3' noncoding regions.

In yet a different aspect of this invention, cells containing recombinant constructs coding for sense and antisense sequences for plant cytoplasmic protein involved in fatty acyl-CoA metabolism are considered. In particular, cells which contain the preferred long chain acyl-CoA substrates of the jojoba protein, such as those cells in embryos of Brassica plants, are considered.

In addition, a method of producing a plant cytoplasmic protein involved in fatty acyl-CoA metabolism in a host cell is provided. Accordingly, a plant cytoplasmic protein involved in fatty acyl-CoA metabolism that is recovered as the result of such expression in a host cell is also considered in this invention.

Further, it may be recognized that the sequences of this invention may find application in the production of wax esters in such host cells which contain fatty acyl and fatty alcohol substrates of the wax synthase. Such host cells may exist in nature or be obtained by transformation with nucleic acid constructs which encode a fatty acyl reductase. Fatty acyl reductase, or "reductase", is active in catalyzing the reduction of a fatty acyl group to the corresponding alcohol. Co-pending U.S. patent applications Ser. Nos. 07/659,975 (filed Feb. 22, 1991, 07/767,251 (filed Sep. 27, 1991) and 07/920,430 (filed Jul. 31, 1992), which are hereby incorporated by reference, are directed to such reductase proteins. This information is also provided in published PCT patent application WO 92/14816. In addition, other sources of wax synthase proteins are described herein which are also desirable sources of reductase proteins. In this regard, plant cells which contain the preferred alcohol substrates of the jojoba wax synthase activity described herein may be prepared by transformation with recombinant nucleic acid constructs which encode a fatty acyl reductase nucleic acid sequence.

A further method considered herein involves the production of very long chain fatty acids, or modification of the amounts of such fatty acids, in host cells. Increased production of very long chain fatty acids may be obtained by expression of DNA sequences described herein. On the other hand, antisense constructs containing such sequences may be used to reduce the content of the very long chain fatty acids in a target host organism. In particular, such sense and antisense methods are directed to the modification of fatty acid profiles in plant seed oils and may result in novel plant seed oils having desirable fatty acid compositions.

DETAILED DESCRIPTION OF THE INVENTION

The nucleic acid sequences of this invention encode a plant cytoplasmic protein involved in fatty acyl-CoA metabolism. Such as a protein includes any sequence of amino acids, such as protein, polypeptide or peptide fragment, which provides the "elongase" activity responsible for production of very long chain fatty acids and for the "wax synthase" activity which provides for esterification of a fatty alcohol by a fatty acyl group to produce a wax ester.

The plant cytoplasmic protein involved in fatty acyl-CoA metabolism of this invention may demonstrate activity towards a variety of acyl substrates, such as fatty acyl-CoA fatty alcohol and fatty acyl-ACP molecules. In addition, both the acyl and alcohol substrates acted upon by the wax synthase may have varying carbon chain lengths and degrees of saturation, although the plant cytoplasmic protein involved in fatty acyl-CoA metabolism may demonstrate preferential activity towards certain molecules.

Many different organisms contain products derived from very long chain fatty acyl-CoA molecules and are desirable sources of a plant cytoplasmic protein involved in fatty acyl-CoA metabolism of this invention. For example, plants produce epidermal, or cuticular wax (Kolattukudy (1980) in *The Biochemistry of Plants* (Stumpf, P. K. and Conn, E. E., eds.) Vol. 4, p. 571–645), and the desert shrub, jojoba, produces a seed storage wax (Ohlrogge et al. (Lipids (1978) 13:203–210). Such waxes are the result of a wax synthase catalyzed combination of a long chain or very long chain acyl-CoA molecule with a fatty alcohol molecule. Wax synthesis has also been observed in various species of bacteria, such as Acinetobacter (Fixter et al. (1986) *J. Gen. Microbiol.* 132:3147–3157) and Micrococcus (Lloyd (1987) *Microbios* 52:29–37), and by the unicellular organism, Euglena (Khan and Kolattukudy (1975) *Arch. Biochem. Biophys.* 170:400–408). In addition, wax production and wax synthase activity have been reported in microsomal preparations from bovine meibomian glands (Kolattukudy et al. (1986) *J. Lipid Res.* 27:404–411), avian uropygial glands, and various insect and marine organisms. Consequently, many different wax esters which will have various properties may be produced by wax synthase activity of plant cytoplasmic protein involved in fatty acyl-CoA metabolism of this invention, and the type of wax ester produced may depend upon the available substrate or the substrate specificity of the particular protein of interest.

Thus, nucleic acid sequences associated with the plant cytoplasmic protein involved in fatty acyl-CoA metabolism may be cloned into host cells for the production of the enzyme and further studies of the activity. For example, one may clone the nucleic acid encoding sequence into vectors for expression in *E. coli* cells to provide a ready source of the protein. The protein so produced may also be used to raise antibodies for use in identification and purification of related proteins from various sources, especially from plants. In addition, further study of the protein may lead to site-specific mutagenesis reactions to further characterize and improve its catalytic properties or to alter its fatty alcohol or fatty acyl substrate specificity. A plant cytoplasmic protein involved in fatty acyl-CoA metabolism having such altered substrate specificity may find application in conjunction with other FAS enzymes.

Prior to the instant invention, amino acid sequences of wax synthase proteins were not known. Thus, in order to obtain the nucleic acid sequences associated with wax synthase, it was necessary to first purify the protein from an available source and determine at least partial amino acid sequence so that appropriate probes useful for isolation of wax synthase nucleic acid sequences could be prepared.

The desert shrub, *Simmondsia chinensis* (jojoba) is the source of the encoding sequences exemplified herein. However, related proteins may be identified from other source organisms and the corresponding encoding sequences obtained.

For example, *Euglena gracilis* produces waxes through the enzymatic actions of a fatty acyl-CoA reductase and a fatty acyl-CoA alcohol transacylase, or wax synthase. Typically, waxes having carbon chain lengths ranging from 24–32 are detected in this organism. The Euglena wax synthase enzyme may be solubilized using a CHAPS/NaCl solution, and a partially purified wax synthase preparation is obtained by Blue A chromatography. In this manner, a 41 kD peptide band associated with wax synthase activity is identified.

Acinetobacter species are also known to produce wax ester compositions, although the mechanism is not well defined. As described herein a fatty acyl-CoA alcohol transacylase, or wax synthase activity is detected in Acinetobacter species. The wax synthase activity is solubilized in CHAPS/NaCl, enriched by Blue A column chromatography and may be further purified using such techniques as size exclusion chromatography. By these methods, an approximately 45 kD peptide band associated with wax synthase activity is obtained in a partially purified preparation.

In addition, a plant cytoplasmic protein involved in fatty acyl-CoA metabolism which is required for production of very long chain fatty acids may also be found in various sources, especially plan sources. In plants, fatty acids up to 18 carbons in chain length are synthesized in the chloroplasts by fatty acid synthase (FAS), a system of several enzymes that elongate fatty acid thioesters of acyl carrier protein (ACP) in 2 carbon increments. After reaching the chain length of 18, the thioester linkage is cleaved by a thioesterase, and the fatty acid is transported to the cytoplasm where it is utilized as a coenzyme A (CoA) thioester as acyl-CoA. Further elongation, when it occurs, is catalyzed by an endoplasmic reticulum membrane associated set of elongation enzymes. Very long chain fatty acids (those fatty acids longer than 18 carbons) are found in the cuticular "waxes" of many plant species, and are found in the seed oil of several plant species. The enzymes involved in elongation of fatty acids to VLCFA are membrane associated (Harwood 1988, von Wettstein-Knowles 1993).

Plants which contain desirable "elongase" activities include Arabidopsis, Crambe, Nasturtium and Limnanthes. Thus, the proteins responsible for such elongase activity may be purified and the corresponding encoding sequences identified. Alternatively, such sequences may be obtained by hybridization to the jojoba encoding sequences provided herein.

Although the hydrophobic nature of the proteins of this invention may present challenges to purification, recovery of substantially purified protein can be accomplished using a variety of methods. See, for example, published PCT application WO 93/10241 where purification of jojoba wax synthase protein is described.

Thus, the nucleic acid sequences which encode a plant cytoplasmic protein involved in fatty acyl-CoA metabolism of this invention may be used to provide for transcription of the sequences and/or expression of the protein in host cells, either prokaryotic or eukaryotic.

Ultimately, stable plant expression in a plant which produces substrates recognized by this enzyme is desired. If a plant targeted for transformation with wax synthase sequences does not naturally contain the fatty alcohol and/or fatty acyl ester substrates of this enzyme, a plant extract may be prepared and assayed for activity by adding substrates to the extract. Constructs and methods for transformation of plant hosts are discussed in more detail below.

As discussed in more detail in the following examples, expression of the nucleic acid sequences provided herein in an initial experiment resulted in increased wax synthase activity. This result, however, was not observed in further E. coli expression experiments. In plants, expression of the exemplified sequences (construct pCGN7626, described in Example 8) resulted in production of very long chain fatty acids in a canola type Brassica, and modification of the very long chain fatty acid profile in transformed Arabidopsis plants (Example 11).

The nucleic acids of this invention may be genomic or cDNA and may be isolated from cDNA or genomic libraries or directly from isolated plant DNA. Methods of obtaining gene sequences once a protein is purified and/or amino acid sequence of the protein is obtained are known to those skilled in the art.

For example, antibodies may be raised to the isolated protein and used to screen expression libraries, thus identifying clones which are producing the plant cytoplasmic protein involved in fatty acyl-CoA metabolism synthase protein or an antigenic fragment thereof. Alternatively, oligonucleotides may be synthesized from the amino acid sequences and used in isolation of nucleic acid sequences. The oligonucleotides may be useful in PCR to generate a nucleic acid fragment, which may then be used to screen cDNA or genomic libraries. In a different approach, the oligonucleotides may be used directly to analyze Northern or Southern blots in order to identify useful probes and hybridization conditions under which these oligonucleotides may be used to screen cDNA or genomic libraries.

Nucleic acid sequences of this invention include those corresponding to the jojoba plant cytoplasmic protein involved in fatty acyl-CoA metabolism, as well as sequences obtainable from the jojoba protein or nucleic acid sequences. By "corresponding" is meant nucleic acid sequences, either DNA or RNA, including those which encode the jojoba plant cytoplasmic protein involved in fatty acyl-CoA metabolism protein or a portion thereof, regulatory sequences found 5' or 3' to said encoding sequences which direct the transcription or transcription and translation (expression) of the protein in jojoba embryos, intron sequences not present in the cDNA, as well as sequences encoding any leader or signal peptide of a precursor protein that may be required for insertion into the endoplasmic reticulum membrane, but is not found in the mature plant cytoplasmic protein involved in fatty acyl-CoA metabolism.

By sequences "obtainable" from the jojoba sequence or protein, is intended any nucleic acid sequences associated with a desired plant cytoplasmic protein involved in fatty acyl-CoA metabolism protein that may be synthesized from the jojoba amino acid sequence, or alternatively identified in a different organism, and isolated using as probes the provided jojoba nucleic acid sequences or antibodies prepared against the jojoba plant cytoplasmic protein involved in fatty acyl-CoA metabolism. In this manner, it can be seen that sequences of these other plant cytoplasmic protein involved in fatty acyl-CoA metabolism may similarly be used to isolate nucleic acid sequences associated with such proteins from additional sources.

For isolation of nucleic acid sequences, cDNA or genomic libraries may be prepared using plasmid or viral vectors and techniques well known to those skilled in the art. Useful nucleic acid hybridization and immunological methods that may be used to screen for the desired sequences are also well known to those in the art and are provided, for example in Maniatis, et al. (*Molecular Cloning: A Laboratory Manual*, Second Edition (1989) Cold Spring Harbor Laboratory, Cold Spring Harbor, N.Y.).

Typically, a sequence obtainable from the use of nucleic acid probes will show 60–70% sequence identity between the target sequence and the given sequence encoding a wax synthase enzyme of interest. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80 sequence homology) from the sequences used as probe. Oligonucleotide probes can be considerably shorter than the entire nucleic acid sequence encoding a wax synthase enzyme, but should be at least about 10, preferably at least about 15, and more preferably at least about 20 nucleotides. A higher degree of sequence identity is desired when shorter regions are used as opposed to longer regions. It may thus be desirable to identify enzyme active sites where amino acid sequence identity is high to design oligonucleotide probes for detecting homologous genes.

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, either Northern or Southern blots (to screen desired sources for homology), or the filters containing cDNA or genomic clones to be screened. Hybridization and washing conditions may be varied to optimize the hybridization of the probe to the sequences of interest. Lower temperatures and higher salt concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe as discussed in Beltz, et al. (*Methods in Enzymology* (1983) 100:266–285).

A useful probe and appropriate hybridization and washing conditions having been identified as described above, cDNA or genomic libraries are screened using the labeled sequences and optimized conditions. The libraries are first plated onto a solid agar medium, and the DNA lifted to an appropriate membrane, usually nitrocellulose or nylon filters. These filters are then hybridized with the labeled probe and washed as discussed above to identify clones containing the related sequences.

For immunological screening, antibodies to the jojoba protein can be prepared by injecting rabbits or mice (or other appropriate small mammals) with the purified protein. Methods of preparing antibodies are well known to those in the art, and companies which specialize in antibody production are also available. Either monoclonal or polyclonal antibodies can be produced, although typically polyclonal antibodies are more useful for gene isolation.

To screen desired plant species, Western analysis is conducted to determine that a related protein is present in a crude extract of the desired plant species, that cross-reacts with the antibodies to the jojoba plant cytoplasmic protein involved in fatty acyl-CoA metabolism. This is accomplished by immobilization of the plant extract proteins on a membrane, usually nitrocellulose, following electrophoresis, and incubation with the antibody. Many different systems for detection of the antibody/protein complex on the nitrocellulose filters are available, including radiolabeling of the antibody and second antibody/enzyme conjugate systems. Some of the available systems have been described by Oberfelder (Focus (1989) BRL/Life Technologies, Inc. 11:1–5). If initial experiments fail to detect a related protein, other detection systems and blocking agents may be utilized. When cross-reactivity is observed, genes encoding the related proteins can be isolated by screening expression libraries representing the desired plant species. Expression libraries can be constructed in a variety of commercially available vectors, including lambda gt11, as described in Maniatis, et al. (supra).

The clones identified as described above using DNA hybridization or immunological screening techniques are then purified and the DNA isolated and analyzed using known techniques. In this manner, it is verified that the clones encode a related protein. Other plant cytoplasmic protein involved in fatty acyl-CoA metabolism may be obtained through the use of the "new" sequences in the same manner as the jojoba sequence was used.

It will be recognized by one of ordinary skill in the art that nucleic acid sequences of this invention may be modified using standard techniques of site specific mutation or PCR, or modification of the sequence may be accomplished in producing a synthetic nucleic acid sequence. Such modified sequences are also considered in this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of this invention may be a DNA or RNA sequence, derived from genomic DNA, cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the protein) may be synthesized using codons preferred by a selected host. Host-preferred codons may be determined, for example, from the codons used most frequently in the proteins expressed in a desired host species.

The nucleic acid sequences associated with plant cytoplasmic protein involved in fatty acyl-CoA metabolism will find many uses. For example, recombinant constructs can be prepared which can be used as probes or will provide for expression of the protein in host cells. Depending upon the intended use, the constructs may contain the sequence which encodes the entire protein, or a portion thereof. For example, critical regions of the protein, such as an active site may be identified. Further constructs containing only a portion of the sequence which encodes the amino acids necessary for a desired activity may thus be prepared. In addition, antisense constructs for inhibition of expression may be used in which and a portion of the cDNA sequence is transcribed.

Useful systems for expression of the sequences of this invention include prokaryotic cells, such as E. coli, yeast cells, and plant cells, both vascular and nonvascular plant cells being desired hosts. In this manner, the plant cytoplasmic protein involved in fatty acyl-CoA metabolism may be produced to allow further studies, such as site-specific mutagenesis of encoding sequences to analyze the effects of specific mutations on reactive properties of the protein.

The DNA sequence encoding a plant cytoplasmic protein involved in fatty acyl-CoA metabolism of this invention may be combined with foreign DNA sequences in a variety of ways. By "foreign" DNA sequences is meant any DNA sequence which is not naturally found joined to the plant cytoplasmic protein involved in fatty acyl-CoA metabolism sequence, including DNA sequences from the same organism which are not naturally found joined to the plant cytoplasmic protein involved in fatty acyl-CoA metabolism sequences. Both sense and antisense constructs utilizing encoding sequences are considered, wherein sense sequence may be used for expression of a plant cytoplasmic protein involved in fatty acyl-CoA metabolism in a host cell, and antisense sequences may be used to decrease the endogenous levels of a protein naturally produced by a target organism. In addition, the gene sequences of this invention may be employed in a foreign host in conjunction with all or part of the sequences normally associated with the plant cytoplasmic protein involved in fatty acyl-CoA metabolism such as regulatory or membrane targeting sequences.

In its component parts, a DNA sequence encoding a plant cytoplasmic protein involved in fatty acyl-CoA metabolism is combined in a recombinant construct having, in the 5' to 3' direction of transcription, a transcription initiation control region capable of promoting transcription and translation in a host cell, the protein encoding sequence and a transcription termination region. Depending upon the host, the regulatory regions will vary, and may include regions from viral, plasmid or chromosomal Genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as E. coli, B. subtilis, Sacchromyces cerevisiae, including genes such as beta-galactosidase, T7 polymerase, tryptophan E and the like.

For the most part, the recombinant constructs will involve regulatory regions functional in plants which provide for transcription of the plant cytoplasmic protein involved in fatty acyl-CoA metabolism gene either in the sense or antisense orientation, to produce a functional protein or a complementary RNA respectively. For protein expression, the open reading frame, coding for the plant protein or a functional fragment thereof will be joined at its 5' end to a transcription initiation regulatory region such as the wild-type sequence naturally found 5' upstream to the exemplified jojoba. Numerous other promoter regions from native plant genes are available which provide for a wide variety of constitutive or regulatable, e.g., inducible, expression of structural gene sequences.

In addition to sequences from native plant genes, other sequences can provide for constitutive gene expression in plants, such as regulatory regions associated with Agrobacterium genes, including regions associated with nopaline synthase (Nos), mannopine synthase (Mas), or octopine synthase (Ocs) genes. Also useful are regions which control expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, and the like.

In embodiments wherein the expression of the plant cytoplasmic protein involved in fatty acyl-CoA metabolism is desired in a plant host, the use of all or part of the complete plant gene may be desired, namely the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source or enhanced promoters, such as double 35S CaMV promoters, the sequences may be joined together using standard techniques. Additionally, 5' untranslated regions from highly expressed plant genes may be useful to provide for increased expression of the proteins described herein.

The DNA constructs which provide for expression in plants may be employed with a wide variety of plant life, particularly, plants which produce the fatty acyl-CoA substrates of the plant cytoplasmic protein involved in fatty acyl-CoA metabolism, such as Brassica. Other plants of interest produce desirable fatty acyl substrates, such as medium or long chain fatty acyl molecules, and include but are not limited to rapeseed (Canola varieties), sunflower, safflower, cotton, Cuphea, soybean, peanut, coconut and oil palms, and corn.

As to the fatty alcohol substrate for the ester production, other than jojoba, seed plants are not known to produce large quantities of fatty alcohols, although small amounts of this substrate may be available to the wax synthase enzyme. Therefore, in conjunction with the constructs of this invention, it is desirable to provide the target host cell with the capability to produce fatty alcohols from the fatty acyl molecules present in the host cells. For example, a plant fatty acyl reductase and methods to provide for expression of the reductase enzymes in plant cells are described in co-pending application U.S. Ser. No. 07/767,251. The nucleic acid sequence and translated amino acid sequence of the jojoba reductase is provided in FIG. 1. Thus, by providing both the wax synthase and reductase activities to the host plant cell, wax esters may be produced from the fatty alcohol and fatty acyl substrates.

In addition to the jojoba reductase, reductase enzymes from other organisms may be useful in conjunction with the wax synthases of this invention. Other potential sources of reductase enzymes include Euglena, Acinetobacter, Micrococus, certain insects and marine organisms, and specialized mammalian or avian tissues which are known to contain wax esters, such as bovine meibomian glands or avian uropygial glands. Other potential sources of reductase proteins may be identified by their ability to produce fatty alcohols or, if wax synthase is also present, wax esters.

The sequences encoding wax synthase activity and reductase sequences may be provided during the same transformation event, or alternatively, two different transgenic plant lines, one having wax synthase constructs and the other having reductase constructs may be produced by transformation with the various constructs. These plant lines may then be crossed using known plant breeding techniques to provide wax synthase and reductase containing plants for production of wax ester products.

For applications leading to wax ester production, 5' upstream non-coding regions obtained from genes regulated during seed maturation are desired, especially those preferentially expressed in plant embryo tissue, such as regions derived from ACP, oleosin (Lee and Huang (1991) *Plant Physiol.* 96:1395–1397) and napin regulatory regions. Transcription initiation regions which provide for preferential expression in seed tissue, i.e., which are undetectable in other plant parts, are considered desirable for wax ester production in order to minimize any disruptive or adverse effects of the gene product in other plant parts. Further, the seeds of such plants may be harvested and the lipid reserves of these seeds recovered to provide a ready source of wax esters. Thus, a novel seed product may be produced in oilseed plants which, absent transformation with wax synthase constructs as described herein, are not known to produce wax esters as a component of their seed lipid reserves.

Similarly, seed promoters are desirable where VLCFA production or inhibition of VLCFA are desired. In this manner, levels of VLCFA may be modulated in various plant species. Such "seed-specific promoters" may be obtained and used in accordance with the teachings of U.S. Ser. No. 07/147,781, filed Jan. 25, 1988 (now U.S. Ser. No. 07/742,834, filed Aug. 8, 1981), and U.S. Ser. No. 07/494,722 filed on Mar. 16, 1990 having a title "Novel Sequences Preferentially Expressed In Early Seed Development and Methods Related Thereto", all of which co-pending applications are incorporated herein by reference. In addition, where plant genes, such as the jojoba protein is expressed, it may be desirable to use the entire plant gene, including 5' and 3' regulatory regions and any introns that are present in the encoding sequence, for expression of the jojoba genes in a transformed plant species, such as Arabidopsis or Brassica.

Regulatory transcription termination regions may be provided in recombinant constructs of this invention as well. Transcription termination regions may be provided by the DNA sequence encoding the plant cytoplasmic protein involved in fatty acyl-CoA metabolism or a convenient transcription termination region derived from a different gene source, especially the transcription termination region which is naturally associated with the transcription initiation region. The transcript termination region will contain at least about 0.5 kb, preferably about 1–3 kb of sequence 3' to the structural gene from which the termination region is derived.

Additional plant gene regions may be used to optimize expression in plant tissues. For example, 5' untranslated regions of highly expressed genes, such as that of the small subunit (SSU) of RuBP-carboxylase, inserted 5' to DNA encoding sequences may provide for enhanced translation efficiency. Portions of the SSU leader protein encoding region (such as that encoding the first 6 amino acids) may also be used in such constructs. In addition, for applications where targeting to plant plastid organelles is desirable, transit peptide encoding sequences from SSU or other nuclear-encoded chloroplast proteins may be used in conjunction with wax synthase and reductase sequences.

Depending on the method for introducing the DNA expression constructs into the host cell, other DNA sequences may be required. Importantly, this invention is applicable to dicotyledon and monocotyledon species alike and will be readily applicable to new and/or improved transformation and regeneration techniques.

In developing the recombinant construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the recombinant construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Similarly, genes encoding enzymes providing for production of a compound identifiable by color change, such as GUS, or luminescence, such as luciferase are useful. Depending upon the number of different host species the expression construct or components thereof are introduced, one or more markers may be employed, where different conditions for selection are used for the different hosts.

In addition to the sequences providing for transcription of sequences encoding the plant cytoplasmic protein involved in fatty acyl-CoA metabolism of this invention, the DNA constructs of this invention may also provide for expression of an additional gene or genes, whose protein product may act in conjunction with the protein described herein to produce a valuable end product. For example, as discussed above, DNA constructs which provide for expression of wax synthase activity and a fatty acyl reductase so that wax esters may produced in transformed hosts, are considered in this invention. Furthermore, production of different wax esters having varying carbon chain lengths and degrees of saturation is desired and may be provided by transforming host plants having fatty alcohol or fatty acyl substrates of varying chain lengths. Such method may be provided, for example, by methods described in the published international patent application number PCT WO 91/16421, which describes various thioesterase genes and methods of using such genes to produce fatty acyl substrates having varying chain lengths in transformed plant hosts.

Furthermore, to optimize the production of wax esters in oilseed plant hosts, one may wish to decrease the production of the triacylglyceride oils that are normally produced in the seeds of such plants. One method to accomplish this is to antisense a gene critical to this process, but not necessary for the production of wax esters. Such gene targets include diacylglycerol acyltransferase, and other enzymes which catalyze the synthesis of triacylglycerol. Additionally, it may be desirable to provide the oilseed plants with enzymes which may be used to degrade wax esters as a nutrient source, such as may be isolated from jojoba or various other wax producing organisms. In this manner, maximal production of wax esters in seed plant hosts may be achieved.

Wax esters produced in the methods described herein may be harvested using techniques for wax extraction from jojoba or by various production methods used to obtain oil products from various oilseed crops. The waxes thus obtained will find application in many industries, including pharmaceuticals, cosmetics, detergents, plastics, and lubricants. Applications will vary depending on the chain length and degree of saturation of the wax ester components. For example, long chain waxes having a double band in each of the carbon chains are liquid at room temperature, whereas waxes having saturated carbon chain components, may be solid at room temperature, especially if the saturated carbon chains are longer carbon chains.

In applications related to elongase activity, the jojoba gene can be used to increase the chain length of fatty acids in oilseeds by overexpression of the gene in transgenic plants of virtually any species; the gene can also be used as a probe in low stringency hybridization to isolate homologous clones from other species that produce VLCFA. These derived genes can then be used in antisense experiments to reduce the level of VLCFA in the species from which they were isolated, or in other plant species where sufficient gene homology is present. Alternatively, these genes could be overexpressed to increase the quantity of VLCFA in transgenic plants.

Additionally, the DNA from the homologous Brassica gene encoding this enzyme could be used as a plant breeding tool to develop molecular markers to aid in breeding HEAR and canola and other oilseed crops. Such techniques would include using the gene itself as a molecular probe or using the DNA sequence to design PCR primers to use PCR based screening techniques in plant breeding programs.

Furthermore, overexpression of the gene in plant epidermal cells could increase cuticle accumulation thereby increasing drought and stress tolerance of transgenic plants over control plants.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. Other sequences useful in providing for transfer of nucleic acid sequences to host plant cells may be derived from plant pathogenic viruses or plant transposable elements. In addition, techniques of microinjection, DNA particle bombardment, electroporation have been developed which allow for the transformation of various monocot and dicot plant species.

When Agrobacterium is utilized for plant transformation, it may be desirable to have the desired nucleic acid sequences bordered on one or both ends by T-DNA, in particular the left and right border regions, and more particularly, at least the right border region. These border regions may also be useful when other methods of transformation are employed.

Where Agrobacterium or Rhizogenes sequences are utilized for plant transformation, a vector may be used which may be introduced into an Agrobacteriumhost for homologous recombination with the T-DNA on the Ti- or Ri-plasmid present in the host. The Ti- or Ri- containing the T-DNA for recombination may be armed (capable of causing gall formation), or disarmed (incapable of causing gall formation), the latter being permissible so long as a functional complement of the vir genes, which encode transacting factors necessary for transfer of DNA to plant host cells, is present in the transformed Agrobacterium host. Using an armed Agrobacterium strain can result in a mixture of normal plant cells, some of which contain the desired nucleic acid sequences, and plant cells capable of gall formation due to the presence of tumor formation genes. Cells containing the desired nucleic acid sequences, but lacking tumor genes can be selected from the mixture such that normal transgenic plants may be obtained.

In a preferred method where Agrobacterium is used as the vehicle for transforming host plant cells, the expression or transcription construct borderedby the T-DNA border region (s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci.*, U.S.A. (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in Agrobacterium. See, for example, McBride and Summerfelt (*Plant Mol. Biol.* (1990) 14:269–276), wherein the pRiHRI (*Jouanin, et al., Mol. Gen. Genet.* (1985) 201:370–374) origin of replication is utilized and provides for added stability of the plant expression vectors in host Agrobacterium cells.

Utilizing vectors such as those described above, which can replicate in Agrobacterium is preferred. In this manner, recombination of plasmids is not required and the host Agrobacterium vir regions can supply trans-acting factors required for transfer of the T-DNA bordered sequences to plant host cells. For transformation of Brassica cells, Agrobacterium transformation methods may be used. One such method is described, for example, by Radke et al. (*Theor. Appl. Genet.* (1988) 75:685–694).

The invention now being generally described, it will be more readily understoodby reference to the following examples, which are included for purposes of illustration only and are not intended to limit the invention unless so stated.

EXAMPLES

Example 1—Wax Synthase Assays

Methods to assay for wax synthase activity in microsomal membrane preparations or solubilized protein preparations are described.

A. Radiolabeled Material

The substrate generally used in the wax synthase assays, [1-$^{14}$C]palmitoyl-CoA, is purchased from Amersham (Arlington Heights, Ill.). Other chain length substrates were synthesized in order to perform chain length specification studies. Long chain [1-$^{14}$C] fatty acids (specific activity 51–56 Ci/mole), namely 11-cis-eicosenoic acid, 13-cis-docosenoic acid and 15-cis-tetracosenoic acid are preparedby the reaction of potassium [$^{14}$C]cyanide with the corresponding alcohol mesylate, followed by the base hydrolysis of the alcohol nitrile to the free fatty acid. The free fatty acids are converted to their methyl esters with ethereal diazomethane, and purified bypreparative silver nitrate thin layer chromatography (TLC). The fatty acid methyl esters are hydrolyzed back to the free fatty acids. Radiochemical purity is assessed by three TLC methods: normal phase silica TLC, silver nitrate TLC, and C18 reversed phase TLC. Radiochemical purity as measured by these methods was 92–98%. Long chain [1-$^{14}$C] acyl-CoAs are prepared from the corresponding [1-$^{14}$C] free fatty acids by the method of Young and Lynen (*J. Bio. Chem.* (1969) 244:377), to a specific activity of 10 Ci/mole. [1-$^{14}$C] hexadecanal is prepared by the dichromate oxidation of [1-$^{14}$C]hexadecan-1-ol, according to a micro-scale modification of the method of Pletcher and Tare (Tet. Lett. (1978) 1601–1602). The product is purified by preparative silica TLC, and stored as a hexane solution at –70° C. until use.

B. Assay for Wax Synthase Activity in a Microsomal Membrane Preparation

Wax synthase activity in a microsomal membrane preparation is measured by incubation of 40 µM [1-$^{14}$C]acyl-CoA (usually palmitoyl-CoA, sp. act. 5.1–5.6 mCi/mmol) and 200 µM oleyl alcohol with the sample to be assayed in a total volume of 0.25 ml. The incubation mixture also contains 20% w/v glycerol, 1 mM DTT, 0.5M NaCl and is buffered with 25 mM HEPES (4-[2-hydroxyethyl]-1-piperazineethane-sulfonic acid). HEPES, here and as referred to hereafter is added from a 1M stock solution adjusted to pH 7.5.

A substrate mixture is prepared in a glass vial, with oleyl alcohol being added immediately before use, and is added to samples. Incubation is carried out at 30° C. for one hour. The assay is terminated by placing the assay tube on ice and immediately adding 0.25 ml isopropanol:acetic acid (4:1 v/v). Unlabeled wax esters (0.1 mg) and oleyl alcohol (0.1 mg) are added as carriers. The [$^{14}$C] lipids are extracted by the scaled-down protocol of Hara and Radin (*Anal. Biochem.* (1978) 90:420). Four ml of hexanne/isopropanol (3:2, v/v) is added to the terminated assay. The sample is vortexed, 2 ml of aqueous sodium sulphate solution (6.6% w/v) is added, and the sample is again vortexed.

C. Assay for Solubilized Wax Synthase Activity

For assaying solubilized wax synthase activity, reconstitution of the protein is required. Reconstitution is achievedby the addition of phospholipids (Sigam P-3644, ~40% L-phosphatidyl choline) to the 0.75% CHAPS-solubilized sample at a concentration of 2.5 mg/ml, followed by dilution of the detergent to 0.3%, below the CMC. Reconstitution of activity is presumed to be based on the incorporation of wax synthase into the phospholipid vesicles. It is recognized that the amount of wax synthase activity detected after their reconstitution can be influenced by many factors (e.g., the phospholipid to protein ratio and the physical state of the wax synthase protein (e.g. aggregate or dispersed).

D. Analysis of Assay Products

For analyzing the products of either the microsomal membrane preparation wax synthase assay or the solubilized wax synthase assay, two protocols have been developed. One protocol, described below as "extensive assay" is more time-consuming, but yields more highly quantitative results. The other protocol, described below as "quick assay" also provides a measure of wax synthase activity, but is faster, more convenient and less quantitative.

1. Extensive Analysis:

Following addition of the sodium sulphate and vortexing the sample, the upper organic phase is removed and the lower aqueous phase is washed with 4 ml hexane/isopropanol (7:2 v/v). The organic phases are pooled and evaporated to dryness under nitrogen. The lipid residue is resuspended in a small volume of hexane, and an aliquot is assayed for radioactivity by liquid scintillation counting. The remainder of the sample can be used for TLC analysis of the labeled classes and thereby give a measure of total wax produced.

For lipid class analysis the sample is applied to a silica TLC plate, and the plate is developed in hexane/diethyl ether/acetic acid (80:20:1 v/v/v). The distribution of radioactivity between the lipid classes, largely wax esters, free fatty acids, fatty alcohols, and polar lipids at the origin, is measured using an AMBIS radioanalytic imaging system (AMBIS Systems Inc., San Diego, Calif.). If necessary the individual lipid classes can be recovered from the TLC plate for further analysis. Reversed-phase TLC systems using C18 plates developed in methanol have also been used for the analysis.

2. Quick Analysis:

Following addition of the sodium sulfate and vortexing the sample, a known percentage of the organic phase is removed and counted via liquid scintillation counting. This calculation is used to estimate the total counts in the organic phase. Another portion of the organic phase is then removed, dryed down under nitrogen, redissolved in hexane and spotted on TLC plates and developed and scanned as described for the detailed assay. In this manner the percentage of the total counts which are incorporated into wax is determined.

Example 2—Radiolabeling Wax Synthase Protein

Radiolabeled [1-$^{14}$C]palmitoyl-CoA (Amersham) is added to a wax synthase preparation, either solubilized or a microsomal membrane fraction, in the ratio of 5 µl of label to 40 µl protein sample. The sample is incubated at room temperature for at least 15 minutes prior to further treatment. For SDS-PAGE analysis the sample is treated directly with SDS sample buffer and loaded onto gels for electrophoresis.

Example 3—Further Studies to Characterize Wax Synthase Activity

A. Seed Development and Wax Synthase Activity Profiles

Embryo development was tracked over two summers on five plants in Davis, Calif. Embryo fresh and dry weights were found to increase at a fairly steady rate from about day 80 to about day 130. Lipid extractions reveal that when the embryo fresh weight reaches about 300 mg (about day 80), the ratio of lipid weight to dry weight reaches the maximum level of 50%.

Wax synthase activity was measured in developing embryos as described in Example 1. As the jojoba seed coats were determined to be the source of an inhibiting factor(s), the seed coats were removed prior to freezing the embryos in liquid nitrogen for storage at −70° C.

Development profiles for wax synthase activities as measured in either a cell free homogenate or a membrane fraction, indicate a large induction in activity which peaks at approximately 110–115 days after anthesis. Embryos for enzymology studies were thus harvested between about 90 to 110 days postanthesis, a period when the wax synthase activity is high, lipid deposition has not reached maximum levels, and the seed coat is easily removed. The highest rate of increase of wax synthase activity is seen between days 80 and 90 postanthesis. Embryos for cDNA library construction were thus harvested between about 80 to 90 days postanthesis when presumably the rate of synthase of wax synthase protein would be maximal. Correspondingly, the level of mRNA encoding wax synthase would be presumed to be maximal at this stage.

B. Substrate Specificity

Acyl-CoA and alcohol substrates having varying carbon chain lengths and degrees of unsaturation were added to a microsomal membrane fraction having wax synthase activity to determine the range of substrates recognizedby the jojoba wax synthase. Wax synthase activity was measured as described in Example 1, with acyl specificity measured using 80 µM of acyl-CoA substrate and 100 µM of radiolabeled oleyl alcohol. Alcohol specificity was measured using 100 µM of alcohol substrate and 40 µM of radiolabeled eicosenoyl-CoA. Results of these experiments are presented in Table 1 below.

TABLE 1

Acyl and Alcohol Substrate Specificity of Jojoba Wax Synthase

| Substrate Structure | Wax synthase Activity (pmoles/min) | |
|---|---|---|
| | Acyl Group | Alcohol Group |
| 12:0 | 12 | 100 |
| 14:0 | 95 | 145 |
| 16:0 | 81 | 107 |
| 18:0 | 51 | 56 |
| 20:0 | 49 | 21 |
| 22:0 | 46 | 17 |
| 18:1 | 22 | 110 |
| 18:2 | 7 | 123 |
| 20:1 | 122 | 72 |
| 22:1 | 39 | 41 |
| 24:1 | 35 | 24 |

The above results demonstrate that the jojoba wax synthase utilizes a broad range of fatty acyl-CoA and fatty alcohol substrates.

In addition, wax synthase activity towards various acyl-thioester substrates was similarly tested using palmitoyl-CoA, palmitoyl-ACP and N-acetyl-S-palmitoyl cysteamine as acyl substrates. The greatest activity was observed with the acyl-CoA substrate. Significant activity (~10% of that with acyl-CoA) was observed with acyl-ACP, but no activity was detectable with the N-acetyl-S-palmitoyl cysteamine substrate.

C. Effectors of Activity

Various sulphydryl agents were screened for their effect on wax synthase activity. Organomercurial compounds were shown to strongly inhibit activity. Iodoacetamide and N-ethylmaleamide were much less effective. Inhibition by parahydroxymercuribenzoate was observed, but this inhibition could be reversed by subsequent addition of DTT. These results demonstrate that inhibition by parahydroxymercuribenzoate involves blocking of an essential sulphydryl group.

D. Size Exclusion Chromatoaraphy

A column (1.5 cm×46 cm) is packed with Sephacryl-200 (Pharmacia), sizing range: 5,000–250,000 daltons) and equilibrated with column buffer (25 mM HEPES, 20% glycerol, 0.75% CHAPS, 1 mM EDTA) containing 0.5M NaCl. Approximately 2 ml of a pooled concentrate from a single 1.5M NaCl elution from a Blue A column (see Ex. 4C) is loaded and the column run at 0.5 ml/min. The eluted fractions are assayed for wax synthase activity according to the reconstitution protocol described in Example 1. Wax synthase activity appears as a broad peak beginning at the void fraction and decreasing throughout the remainder of the run. A portion of the fractions having wax synthase activity are treated with 1-$^{14}$C 16:0-CoA (0.0178 uM) for 15 minutes at room temperature. SDS is added to 2% and the samples are loaded on an SDS-PAGE gel. Following electrophoresis, the gel is blotted to Problott (Applied Biosystems; Foster City, Calif.) and the dried blot membrane analyzed by autoradiography. Alternatively, the blot may be scanned for radioactivity using an automated scanning system (AMBIS; San Diego, Calif.). In this manner, it is observed that the 57 kD radiolabeled band tracks with wax synthase activity in the analyzed fractions.

Protein associated with wax synthase activity is further characterized by chromatography on a second size exclusion matrix. A fraction (100 ul) of a 10X concentrated 1.5M NaCl elution from a Blue A column (following a 1.0M NaCl elution step) which contains wax synthase activity is chromatographed on a Superose 12 HR10/30 column (Pharmacia; Piscataway, N.J.) and analyzed by Fast Protein Liquid Chromatography (FPLC) on a column calibrated with molecular weight standards (MW GF-70 and MWGF-1000; Sigma). Activity assays are performed on the eluted fractions. Most 53% of the recovered wax synthase activity is found in the void fractions, but an easily detectable activity is found to elute at ~55 kd according to the calibration curve. These data indicate the minimum size of an active native wax synthase protein is very similar to the 57 kD size of the labeled band, thus providing evidence that wax synthase activity is providedby a single polypeptide. The fraction of wax synthase activity observed in the void fractions is presumably an aggregated form of the enzyme.

E. Palmitovl-CoA Agarose Chromatography

A column (1.0×3 cm) is packed with 16:0-CoA agarose (Sigma P-5297) and equilibrated with column buffer (See, Example 1, D.) containing 0.2M NaCl. Approximately 4 ml of a pooled concentrate from the 1.5M NaCl wash of the Blue A column is thawed and the salt concentration reduced by passage of the concentrate over a PD-10 (Pharmacia) desalting column equilibrated in 0.2M NaCl column buffer. The reduced salt sample (5 ml) is loaded onto the 16:0 CoA agarose column at a flow rate of 0.15 ml/min. The column is washed with 0.5M NaCl column buffer and then with 1.5M NaCl column buffer. Although some wax synthase activity flows through the column or is removed by the 0.5M NaCl wash, the majority of the recovered activity (21% of the loaded activity) is recovered in the 1.5M NaCl eluted peak.

Portions of the fractions which demonstrate wax synthase activity are radiolabeled with [$^{14}$C]palmitoyl-CoA as described in Example 2 and analyzed by SDS polyacrylamide gel electrophoresis (Laemmli, *Nature* (1970) 227:680–685). Again the approximate 57 kD radio labelled protein band is observed to track with wax synthase activity.

Example 4—Purification of Jojoba Wax Synthase

Methods are described which may be used for isolation of a jojoba membrane preparation having wax synthase activity, solubilization of wax synthase activity and further purification of the wax synthase protein.

A. Microsomal Membrane Preparation

Jojoba embryos are harvested at approximately 90–110 days after flowering, as estimated by measuring water content of the embryos (45–70%). The outer shells and seed coats are removed and the cotyledons quickly frozen in liquid nitrogen and stored at −70° C. for future use. For initial protein preparation, frozen embryos are powdered by pounding in a steel mortar and pestle at liquid nitrogen temperature. In a typical experiment, 70 g of embryos are processed.

The powder is added, at a ratio of 280 ml of solution per 70 g of embryos, to the following high salt solution: 3M NaCl, 0.3M sucrose, 100 mM HEPES, 2 mM DTT, and the protease inhibitors, 1 mM EDTA, 0.7 µg/ml leupeptin, 0.5 µg/ml pepstatin and 17 µg/ml PMSF. A cell free homogenate (CFH) is formedby dispersing the powdered embryos in the buffer with a tissue homogenizer (Kinematica, Switzerland; model PT10/35) for approximately 30 sec. and then filtering through three layers of Miracloth (CalBioChem, LaJolla, Calif.). The filtrate is centrifuged at 100,000×g for one hour.

The resulting sample consists of a pellet, supernatant and a floating fat pad. The fat pad is removed and the supernatant fraction is collected and dialyzed overnight (with three changes of the buffering solution) versus a solution containing 1M NaCl, 100 mM HEPES, 2 mM DTT and 0.5M EDTA. The dialyzate is centrifuged at 200,000×g for 1½ hour to yield a pellet, DP2. The pellet is suspended in 25 mM HEPES and 10% glycerol, at $\frac{1}{20}$ of the original CFH volume, to yield the microsomal membrane preparation.

Activity is assayed as described in Example 1. Recovery of wax synthase activity is estimated at 34% of the original activity in the cell free homogenate. Wax synthase activity in this preparation is stable when stored at −70° C.

B. Solubilization of Wax Synthase Protein

CHAPS (3-[(3-cholamidopropyl)-dimethyl-ammonio]-1-propanesulfonate) and NaCl are added to the microsomal membrane preparation to yield final concentrations of 2% and 0.5M, respectively. The samples are incubated on ice for approximately one hour and then diluted with 25 mM HEPES, 20% glycerol, 0.5M NaCl to lower the CHAPS concentration to 0.75%. The sample is then centrifuged at 200,000×g for one hour and the supernatant recovered and assayed for wax synthase activity as described in Example 1.C. Typically, 11% of the wax synthase activity from the microsomal membrane preparation is recovered in the supernatant fraction. The solubilized wax synthase activity is stable when stored at −70° C.

C. Blue A Column Chromatoaraphy

A column (2.5×8 cm) with a bed volume of approximately 30 ml is prepared which contains Blue A (Cibacron Blue F3GA; Amicon Division, W. R. Grace & Co.), and the column is equilibrated with the column buffer (25 mM HEPES, 20% glycerol, 0.75% CHAPS, 1 mM EDTA) containing 0.4M NaCl. The solubilized wax synthase preparation is diluted to 0.4M NaCl by addition of column buffer (25 mM HEPES, 20% glycerol, 0.75% CHAPS, 1 mM EDTA) and loaded to the Blue A column.

The column is washed with column buffer containing 0.5M NaCl until no protein can be detected (as measured by absorbance at 280 nm) in the buffer flowing through the column. Greater than 94% of the wax synthase activity binds to the column, while greater than 83% of other protein passes through. Typically, approximately 20% of the loaded wax synthase activity is recoveredby elution. A portion of the recovered activity (17%) elutes with a 1.0M NaCl column buffer wash, while approximately 75% of the recovered activity elutes as a broad peak in a 150 ml wash with 1.5M NaCl column buffer. Five ml fractions of the 1.5M wash are collected and assayed for wax synthase activity as described in Example 1. Fractions containing wax synthase activity are pooled and concentrated ten fold using an Amicon stirred cell unit and a YM30 membrane. The concentrated wax synthase preparation may be stored at −70° C.

D. Size Exclusion Column Chromatoaraphy

In fractions collected from chromatography on Blue A the acyl-transferase enzyme activity responsible for formation of wax esters from fatty alcohol and acyl-CoA co-elutes with the measurable activity of β-ketoacyl-CoA synthase. The β-ketoacyl-CoA synthase activity can be separated from this wax synthase activity through size exclusion chromatography using S 100 sepharose. The preferred column buffer for size exclusion chromatography comprises 1.0% CHAPS, as at 0.75% CHAPS the enzyme tends to aggregate, i.e., stick to itself and other proteins. Using a column buffer adjusted to 1.0% CHAPS allows clean separation of the activity of wax synthase on S 100, wax synthase being retained, from the β-ketoacyl-CoA synthase protein, the latter being voided. The majority of wax synthase activity elutes from the S 100 sizing column as a peak with a molecular mass ~ of 57 kDa. At 0.75% CHAPS only a small portion of total assayable wax synthase activity is found at 57 kDa, with the remainder distributed over void and retained fractioins.

Wax synthase also has an estimated molecular mass of ~57 kDa based on SDS gels of radiolabelled protein, i.e., wax synthase protein which has been labeled by the procedure described above by incubation with 14C-palmitoyl-CoA. The labelled band tracks with wax synthase activity in fractions collected from a size exclusion column, while β-ketoacyl-CoA synthase activity is completely voidedby the S 100 column.

As a predominant 57 kDa protein from the Blue A column fraction, the β-ketoacyl-CoA synthase can be amino acid sequenced from bands removed from SDS PAGE. Wax synthase activity can be isolatedby SDS PAGE and clonedby a similar procedure from fractions retained on S 100.

E. SDS PAGE Analysis

Samples from the S 100 or active BlueA column fractions are diluted in SDS PAGE sample buffer (1×buffer=2% SDS, 30 mM DTT, 0.001% bromphenol blue) and analyzed by electrophoresis on 12% tris/glycine precast gels from NOVEX (San Diego, Calif.). Gels are run at 150V, constant voltage for approximately 1.5 hours. Protein is detectedby silver staining (Blum et al., *Electrophoresis* (1987) 8:93-99). Careful examination of the gel reveals only a few polypeptides, including one of approximately 57 kD, whose staining intensity in the various fractions can be correlated with the amount of wax synthase activity detected in those fractions. Furthermore, if radiolabeled [1-$^{14}$C]palmitoyl-CoA is added to the protein preparation prior to SDS PAGE analysis, autoradiography of the gel reveals that the 57 kD labeled band tracks with wax synthase activity in these fractions. Other proteins are also present in the preparation, including the 56 and 54 kD reductase proteins described in co-pending application U.S. Ser. No. 07/767,251.

F. Continuous Phase Elution

Wax synthase protein is isolated for amino acid sequencing using an SDS-PAGE apparatus, Model 491 Prep Cell (Bio-Rad Laboratories, Inc., Richmond, Calif.), according to manufacturer's instructions. A portion (15 ml) of the wax synthase activity from the 1.5M NaCl elution of the Blue A column is concentrated 10 fold in a Centricon 30 (Amicon Division, W. R. Grace & Co.; Beverly, Mass.) and desalted with column buffer on a Pharmacia PD-10 desalting column. The sample is treated with 2% SDS and a small amount of bromphenol blue tracking dye and loaded onto a 5 ml, 4% acrylamide stacking gel over a 20 ml, 12% acrylamide running gel in the Prep Cell apparatus. The sample is electrophoresed at 10 W and protein is continuously collected by the Prep Cell as it elutes from the gel. The eluted protein is then collected in 7.5-10 ml fractions by a fraction collector. One milliliter of each fraction in the area of interest (based on the estimated 57 kD size of the wax synthase protein) is concentrated to 40 μl in a Centricon 30 and treated with 2% SDS. The samples are run on 12% acrylamide mini-gels (Novex) and stained with silver.

Various modifications to the continuous phase elution process in order to optimize for wax synthase recovery may be useful. Such modifications include adjustments of acrylamide percentages in gels volume of the gels, and adjustments to the amount of wax synthase applied to the gels. For example, to isolate greater amounts of the wax synthase protein the Blue A column fractions may be applied to larger volume, 20-55 ml, acrylamide gels at a concentration of approximately 1 mg of protein per 20 ml of gel. The protein fractions eluted from such gels may then be applied 10-15% gradient acrylamide gels for increased band separation.

The protein content of each fraction is evaluated visually and fractions containing wax synthase protein are pooled and concentrated for amino acid sequencing. In order to maximize the amount of wax synthase enzyme collected, fractions which also contain the 56 kD reductase protein band are included in the pooled preparation. As the reductase protein sequence is known (see FIG. 1), further purification of wax synthase protein in the pooled preparation is not necessary prior to application of amino acid sequencing techniques (see Example 5).

G. Blotting Proteins to Membranes

Alternatively, wax synthase protein may be further isolated for amino acid sequencing by transfer to PVDF membranes following SDS-PAGE, either Immobilon-P (Millipore; Bedford, Mass.) or ProBlott (Applied Biosystems; Foster City, Calif.). Although transfer to nitrocellulose may also beinitial initial studies indicate poor transfer to nitrocellulose membranes, most likely due to the hydrophobic nature of this protein. PVDF membranes, such as ProBlott and Immobilon-P find preferential use in different methods, depending on the amino acid sequencing technique to be employed. For example, transfer to ProBlott is useful for N-terminal sequencing methods and for generation of peptides from cyanogen bromide digestion. Immobilon-P is preferred.

1. Blotting to Nitrocellulose:

When protein is electroblotted to nitrocellulose, the blotting time is typically 1-5 hours in a buffer such as 25 mM Tris, 192 mM glycine in 5-20% methanol. Following electroblotting, membranes are stained in 0.1% (w/v) Ponceau S in 1% (v/v) acetic acid for 2 minutes and desrained in 2-3 changes of 0.1% (v/v) acetic acid, 2 minutes for each change. These membranes are then stored wet in heat-sealed plastic bags at −20° C. If time permits, blots are not frozen but used immediately for digestion to create peptides for determination of amino acid sequence as described below.

2. Blotting to PVDF:

When protein is electroblotted to Immobilon P PVDF, the blotting time is generally about 1-2 hours in a buffer such as 25 mM Tris/192 mM glycine in 20% (v/v) methanol. Following electroblotting to PVDF, membranes are stained in 0.1% (w/v) Coomassie Blue in 50% (v/v) methanol/10% (v/v) acetic acid for 5 minutes and destained in 2-3 changes of 50% (v/v) methanol/10% (v/v) acetic acid, 2 minutes for each change. PVDF membranes are then allowed to air dry for 30 minutes and are then stored dry in heat-sealed plastic bags at −20° C. Protein blotted to PVDF membranes such as Pro Blott, may be used directly to determine N-terminal sequence of the intact protein. A protocol for electroblotting proteins to ProBlott is described below in Example 5A.

Example 5—Determination of Amino Acid Sequence

In this example, methods for determination of amino acid sequences of plant proteins associated with wax synthase activity are described.

A. Cyanoaen Bromide Cleavagae of Protein and Separation of Peptides

Cyanogen bromide cleavage is performed on the protein of interest using the methodology described in the Probe-Design Peptide Separation System Technical Manual from Promega, Inc. (Madison, Wis.). The wax synthase protein, if not available in a purified liquid sample, is blotted to a PVDF membrane as described above. Purified wax synthase protein or wax synthase bands from the PVDF blot, are placed in a solution of cyanogen bromide in 70% (v/v) formic acid, and incubated overnight at room temperature. Following this incubation the cyanogen bromide solutions are removed, pooled and dried under a continuous nitrogen stream using a Reacti-Vap Evaporator (Pierce, Rockford, Ill.). Additional elution of cyanogen bromide peptides from PVDF may be conducted to ensure complete removal, using a peptide elution solvent such as 70% (v/v) isopropanol, 0.2% (v/v) trifuoroacetic acid, 0.1 mM lysine, and 0.1 mM thioglycolic acid. The elution solvents are then removed and added to the tube containing the dried cyanogen bromide solution, and dried as described above. The elution procedure may be repeated with fresh elution solvent. 50 µl of HPLC grade water is then added to the dried peptides and the water removed by evaporation in a Speed-Vac (Savant, Inc., Farmingdale, N.Y.).

Peptides generated by cyanogen bromide cleavage are separated using a Tris/Tricine SDS-PAGE system similar to that describedby Schagger and von Jagow (*Anal. Biochem.* (1987) 166:368–379). Gels are run at a constant voltage of 125–150 volts for approximately 1 hour or until the tracking dye has begun to run off the bottom edge of the gel. Gels are soaked in transfer buffer (125 mM Tris, 50 mM glycine, 10% (v/v) methanol) for 15–30 minutes prior to transfer. Gels are blotted to ProBlott sequencing membranes (Applied Biosystems, Foster City, Calif.) for 2 hours at a constant voltage of 50 volts. The membranes are stained with Coomassie blue (0.1% in 50% (v/v) methanol/10% (v/v) acetic acid) and desrained for 3X 2 min. in 50% (v/v) methanol/ 10% (v/v) acetic acid. Membranes are air-dried for 30–45 minutes before storing dry at −20° C.

Peptides blotted on to ProBlott can be directly loaded to the sequencer cartridge of the protein sequencer without the addition of a Polybrene-coated glass fibre filter. Peptides are sequenced using a slightly modified reaction cycle, BLOT-1, supplied by Applied Biosystems. Also, solution S3 (butyl chloride), is replaced by a 50:50 mix of S1 and S2 (n-heptane and ethyl acetate). These two modifications are used whenever samples blotted to ProBlott are sequenced.

B. Protease Digestion and Separation of Peptides

Purified wax synthase protein provided in a liquid solution or wax synthase proteins blotted to nitrocellulose may be subjected to digestion with proteases in order to obtain peptides for sequencing. The method used is that of Aebersold, et al. (*PNAS* (1987) 84:6970).

For protein provided on nitrocellulose, bands of the wax synthase proteins, and also an equal amount of blank nitrocellulose to be used as a control, are cut out of the nitrocellulose membrane and washed several times with HPLC grade water in order to remove the Ponceau S. Following this wash, 1.0 ml of 0.5% polyvinylpyrrolidone (PVP-40, Aldrich, Milwaukee, Wis.) in 0.5% acetic acid is added to the membrane pieces and this mixture is incubated for 30 minutes at 37° C. In order to remove the PVP-40 completely, nitrocellulose pieces are washed with many volumes of HPLC grade water (8×5 ml), checking the absorbance of the washes at 214 nm on a spectrophotometer. Also, PVP-40 is more easily removed if bands are not cut into small pieces until after PVP-40 treatment and washing.

The proteins, in solution or on nitrocellulose pieces, are then suspended in an appropriate digest buffer, for example trypsin digest buffer, 100 mM sodium bicarbonate pH 8.2, or endoproteinase gluC buffer, 25 mM ammonium carbonate/1 mM EDTA, pH 7.8. Acetonitrile is added to the digest mixture to a concentration of 5–10% (v/v). Proteases are diluted in digest buffer and added to the digest mixture, typically at a ratio of 1:10 (w/w) protease to protein. Digests are incubated 18–24 hours. For example, trypsin digests are incubated at 37° C. and endoproteinase gluC digests are incubated at room temperature. Similarly, other proteases may be used to digest the wax synthase proteins, including lysC and aspN. While the individual digest buffer conditions may be different, the protocols for digestion, peptide separation, purification and sequencing are substantially the same as those described for digestion with trypsin and gluC.

Following overnight incubation, digest reactions are stopped by the addition of 10 µl 10% (v/v) trifluoroacetic acid (TFA) or 1 µl 100% TFA. When the protein is provided on nitrocellulose, the nitrocellulose pieces are washed with 1–5 100 µl volumes of digest buffer with 5–10% acetonitrile, and these volumes are concentrated to a volume of less than 100 µl in a Speed-Vac.

The peptides resulting from digestion are separated on a Vydac reverse phase C18 column (2.1 mm×100 mm) installed in an Applied Biosystems (Foster City, Calif.) Model 130 High Performance Liquid Chromatograph (HPLC). Mobile phases used to elute peptides are: Buffer A: 0.1 mM sodium phosphate, pH 2.2; Buffer B: 70% acetonitrile in 0.1 mM sodium phosphate, pH 2.2. A 3-step gradient of 10–55% buffer B over two hours, 55–75% buffer B over 5 minutes, and 75% buffer B isocratic for 15 minutes at a flow rate of 50 µl/minute is used. Peptides are detected at 214 nm, collected by hand, and then stored at −20° C.

Due to the hydrophobic nature of the wax synthase proteins, addition of a detergent in enzyme digestions buffers may be useful. For example, fractions from the continuous phase elution procedure described above which contain the jojoba wax synthase are concentrated in a Centricon 30 in 100 mM NaHCO$_3$/1.0% CHAPS to a final volume of 11082 l. Two µg of trypsin in 5 µl of 100 mM Na HCO$_3$/ 1.0% CHAPS is added to the protein solution and the mixture is incubated overnight at 37° C., and the digestion stopped by addition of trifluoroacetic acid (TFA). The sample is centrifuged lightly and the peptides separated on a Vydac C18 column and eluted as described above. In this procedure, the CHAPS elutes at ~40–53% Buffer B, and obscures the peptide peaks in this region.

Where the primary separation yields a complex peptide pattern, such as where excess protein is used or contaminants (such as the jojoba reductase protein) are present, peptide peaks may be further chromatographed using the same column, but a different gradient system. For the above jojoba wax synthase preparation, hydrophilic peaks were separated using a gradient of 0–40% Buffer B for 60 minutes, 40–75% B for 35 minutes and 75–100% B for 10 minutes. Hydrophobic peaks were separated using 0–40% Buffer B for 40 minutes, 40–80% B for 60 minutes and 80–100% B for 10 minutes. For these separations, Buffer A is 0.1% TFA and Buffer B is 0.1% TFA in acetonitrile.

C. N-terminal Sequencing of Proteins and Peptides

All sequencing is performed by Edman degradation on an Applied Biosystems 477A Pulsed-Liquid Phase Protein Sequencer; phenylthiohydantoin (PTH) amino acids produced by the sequencer are analyzed by an on-line Applied Biosystems 120A PTH Analyzer. Data are collected and stored using an Applied BioSystems model 610A data analysis system for the Apple Macintosh and also on to a Digital Microvax using ACCESS*CHROM software from PE NELSON, Inc. (Cupertino, Calif.). Sequence data is read from a chart recorder, which receives input from the PTH Analyzer, and is confirmed using quantitative data obtained from the model 610A software. All sequence data is read independently by two operators with the aid of the data analysis system.

For peptide samples obtained as peaks off of an HPLC, the sample is loaded on to a Polybrene coated glass fiber filter (Applied Biosystems, Foster City, Calif.) which has been subjected to 3 pre-cycles in the sequencer. For peptides which have been reduced and alkylated, a portion of the PTH-amino acid product material from each sequencer cycle is counted in a liquid scintillation counter. For protein samples which have been electroblotted to Immobilon-P, the band of interest is cut out and then placed above a Polybrene coated glass fiber filter, pre-cycled as above and the reaction cartridge is assembled according to manufacturer's specifications. For protein samples which have been electroblotted to ProBlott, the glass fiber filter is not required.

In order to obtain protein sequences from small amounts of sample (5–30 pmoles), the 477A conversion cycle and the 120A analyzer as described by Tempst and Riviere (*Anal. Biochem.* (1989) 183:290).

Amino acid sequence of jojoba peptides obtained by trypsin digestion as described above are presented in Table 2 below.

TABLE 2

| Amino Acid Sequence of Jojoba 57 kDa protein Tryptic Peptides | |
|---|---|
| SQ1114 | ETYVPESVTKK (SEQ ID NO: 5) |
| SQ1084 | VPXEPSIAAX (SEQ ID NO: 6) |
| SQ1083 | ETYVPEEvtk (SEQ ID NO: 7) |
| SQ1120 | DLMAVAGEAlk (SEQ ID NO: 8) |
| SQ1125 | MTNVKPYIPDF (SEQ ID NO: 9) |
| SQ1129 | FLPXXVAiTGe (SEQ ID NO: 10) |
| SQ1131 | FGNTSSXXLyxelayak (SEQ ID NO: 11) |
| SQ1137 | AEAEEVMYGAIDEVLEK (SEQ ID NO: 12) |

The amino acid sequence is represented using the one letter code. "X" represents a position where the amino acid could not be identified, and amino acids represented by lower case letters represent residues which were identified with a lesser degree of confidence.

Example 6—Purification of Additional Wax Synthases and Reductases

A. Adaptation of jojoba wax synthase solubilization and purification methods to obtain partially purified preparations of wax synthase from other organisms are described.

Acinetobacter

Cells of *Acinetobacter calcoaceticus* strain BD413 (ATCC #33305) are grown on ECLB (*E. coli* luria broth), collected during the logarithmic growth phase and washed in a buffer containing; Hepes, pH 7.5, 0.1M NaCl, 1 mM DTT and protease inhibitors. Washed cells were resuspended in fresh buffer and ruptured bypassage through a French pressure cell (two passes at ~16,000 p.s.i.). Unbroken cells are removed by centrifugation at 5000×g for 10 minutes, and membranes are collected by centrifugation at 100,000×g for 1 hour. The membrane pellet is homogenized in storage buffer (25 mM Hepes, pH 7.5, 10% (w/v) glycerol). Wax synthase activity is detected in these membranes using assay conditions described for the jojoba enzyme in Example 1B, using [1-$^{14}$C] palmitoyl-CoA and 18:1 alcohol as the substrates.

Wax synthase activity is solubilized by incubation of the membranes with 2% CHAPS in the presence of 0.5M NaCl, as described for the jojoba enzyme in Example 4B. Solubilization of the activity is demonstrated by the detection of wax synthase enzyme activity in the supernatant fraction after centrifugation at 200,000 g for 1 hour and by size exclusion chromatography (i.e. the activity elutes from the column in the retained fractions as a symmetrical peak). The activity of the solubilized enzyme is detected by simple dilution of the CHAPS concentration to ~0.3% (i.e. to below its CMC). Incorporation of the enzyme into phospholipid vesicles is not required to detect solubilized activity.

For purification, the solubilized Acinetobacter wax synthase activity is subjected to chromatographic purification procedures similar to those described for the jojoba acyl-CoA reductase. The soluble protein preparation is loaded to a Blue A agarose column under low salt conditions (150 mM NaCl in a column buffer containing 0.75% CHAPS, 10% glycerol, 25 mM Hepes, pH 7.5) and eluted from the column using 1.0M NaCl in the column buffer.

Size exclusion chromatography on Superose 12 (Pharmacia; Piscataway, N.J.) medium is used to obtain an estimate of the size of the native enzyme and to aid in identifying candidate polypeptides. Comparison to molecular mass standards chromatographed under identical conditions yields an estimate of ~46 kD for the native wax synthase activity. Three polypeptides bands, with apparent molecular masses of 45 kD, 58 kD and 64 kD, were identified which tracked with wax synthase activity. N-terminal sequence of the 45 kD polypeptide, the strongest candidate for wax synthase, is determined as XDIAIIGSG-sAGLAQaxilkdag (SEG ID NO:13), where the one letter code for amino acids is used, "X" represents a position where the amino acid could not be identified, and amino acids representedby lower case letters represent residues which were identified with a lesser degree of confidence. In addition, sequence of a tryptic peptide of the Acinetobacter wax synthase protein is determined as QQFTVWXNASEPS (SEG ID NO:14).

Euglena

*Euglena gracilis*, strain Z (ATCC No. 12716) is grown heterotrophically in the dark (Tani et al. (1987) *Agric. Biol. Chem.* 51:225–230) at ~26° C. with moderate shaking. Cells are collected and washed in buffer containing 25 mM Bis-Tris-Propane, pH 7.0, 0.25M NaCl and 1 mM EDTA. Washed cells are resuspended in fresh buffer and ruptured bypassage through a French pressure cell (two passes at ~16,000 p.s.i.). Unbroken cells, cell debris and nuclei are removed by centrifugation at 20,000×g for 20 minutes, and microsomal membranes are collectedby centrifugation at 200,000×g for 1 hour. The membrane pellet is homogenized in storage buffer (25 mM Bis-Tris-Propane, pH 7.0, 0.25M NaCl, 10% (w/v) glycerol and 1 mM EDTA). Wax synthase activity is detected in these membranes using assay conditions as described for the jojoba enzyme. The radiolabelled substrate is the same as for the jojoba example (i.e. [1-$^{14}$C] palmitoyl-CoA), however, 16:0 rather than 18:1 is used as the alcohol acceptor, and Bis-Tris-Propane buffer at pH 7.0 is utilized.

The Euglena wax synthase activity is solubilized by incubation of the membranes with 2% CHAPS in the presence of 0.5M NaCl. Solubilization of the protein is demonstrated by the detection of enzyme activity in the supernatant fraction after centrifugation at 200,000×g for 1 hour. The activity of the solubilized enzyme is detected by dilution of the CHAPS concentration to ~0.3% (i.e. to below its CMC). It is not necessary to incorporate the enzyme into phospholipid vesicles as was the case for the solubilized jojoba wax synthase.

For partial purification, the solubilized Euglena wax synthase activity is subjected to chromatographic separation on Blue A agarose medium. The column is equilibrated with 0.1M NaCl in a column buffer containing; 25 mM Bis-Tris-Propane, pH 7.0, 20% (w/v) glycerol, 0.75% CHAPS and 1 mM EDTA. The sample containing solubilized wax synthase activity is diluted to 0.1M NaCl and loaded onto a 1×7 cm column (5.5 ml bed volume). The column is washed with equilibration buffer and subjected to a linear NaCl gradient (0.1M to 1.0M NaCl) in column buffer. Wax synthase activity is eluted as a broad peak in the last half of the salt gradient.

SDS-PAGE analysis of column fractions reveals that the polypeptide complexity of the activity eluted from the column is greatly reduced relative to the loaded material. A polypeptide with an apparent molecular mass of ~41 kD was observed to track with wax synthase activity in the column fractions. Further purification techniques, such as described for jojoba and Acinetobacter are conducted to verify the association of wax synthase activity with the ~41 kD peptide.

For further analysis of wax synthase activity in Euglena, size exclusion chromatography was conducted as follows. A microsomal membrane preparation was obtained from Euglena cells grown on liquid, heterotrophic, medium (Tani et al., supra) in the dark. Wax synthase activity was solubilized by treating the membranes with 2% (w/v) CHAPS and 500 mM NaCl in a buffered solution (25 mM Bis-Tris, pH 7.0, 1 mM EDTA and 10% (w/v) glycerol) for 1 hour on ice. After dilution of the CHAPS to 0.75% and the NaCl to 200 mM by addition of a dilution buffer, the sample was centrifuged at ~200,000×g for 1.5 hours. The supernatant fraction was loaded onto a Blue A dye column pre-equilibrated with Column Buffer (25 mM Bis-Tris pH 7.0, 1 mM EDTA, 10% glycerol, 0.75% CHAPS) which also contained 200 mM NaCl. The column was washed with Column Buffer containing 200 mM NaCl until the A280 of the effluent returned to the preload value. Wax synthase activity which had bound to the column was released by increasing the NaCl concentration in the Column Buffer to 1.5M. The fractions from the Blue A column containing wax synthase activity released by the 1.5M NaCl (~20 ml combined volume) were pooled and concentrated approximately 30-fold via ultrafiltration (Amicon pressure cell fitted with a YM 30 membrane). The concentrated material from the Blue A column was used as the sample for a separation via size exclusion chromatography on Superose 12 medium (Pharmacia).

Approximately 200 μl of the sample was loaded onto a Superose 12 column (HR 10/30), pre-equilibrated with Column Buffer containing 0.5M NaCl, and developed at a flow rate of 0.1 ml/min. The wax synthase activity eluted from the column as a smooth peak. Comparison of the elution volume of the wax synthase activity with the elution profiles of molecular mass standard proteins yielded an estimate of 166 kD for the apparent molecular mass of the enzyme. Fractions which contained wax synthase activity were analyzed via SDS-polyacrylamide gel electrophoresis followed by silver staining. A preliminary analysis of the polypeptide profiles of the various fractions did not reveal any proteins with molecular masses of 100 kD or greater whose staining intensity appeared to match the activity profile. The wax synthase polypeptide may be present as a minor component in the sample mixture that is not readily detectable on the silver-stained gel. Alternatively, the enzyme may be composed of subunits which are dissociated during SDS-PAGE.

B. In addition to jojoba reductase, such as that encoded by the sequence provided in FIG. 1, reductase proteins from other sources are also desirable for use in conjunction with the wax synthase proteins of this invention. Such proteins may be identified and obtained from organisms known to produce wax esters from alcohol and acyl substrates.

For example, an NADH-dependent fatty acyl-CoA reductase activity can be obtained from microsomal membranes isolated from *Euglena gracilis*. Methods which may be used to isolate microsomal membranes are described, for example in the published PCT patent application WO 92/14816 (application number PCT/US92/03164, filed Feb. 21, 1992). The reductase activity is solubilized from these membranes using the same approaches as used for jojoba reductase and wax synthase. Membranes are incubated on ice for one hour with various amounts of the detergent, CHAPS, in a buffering solution consisting of 25 mM BisTris, pH 6.9, 250 mM NaCl, 10% glycerol and 1 mM EDTA. The sample is then centrifuged at 200,000×g for one hour, and the supernatant and pellet fractions assayed for NADH-dependent reductase activity using radiolabeled palmitoyl-CoA and NADH as substrates. A convenient assay for reductase activity is described in PCT patent application WO 92/14816. Incubation of the membranes with 0.3, 0.5 or 0.7% (w/v) CHAPS results in retention of reductase activity in the supernatant fractions, indicative of solubilization of the enzyme. If CHAPS is omitted during the incubation and centrifugation, all of the reductase activity is found in the pellet fraction. All of the samples are diluted ten-fold in this same buffer solution prior to assaying in order to dilute the CHAPS present during the incubation. The presence of CHAPS in the assay at levels above the CMC (approximately 0.5% (w/v) results in inhibition of enzyme activity. Stability of the reductase activity in up to 2% CHAPS may be improved by increasing the glycerol concentration in the buffering solution to 20%. Reductase activity is recovered by dilution of the CHAPS to below the CMC.

Example 7—Isolation of Nucleic Acid Sequences

Isolation of nucleic acid sequences from cDNA libraries or from genomic DNA is described.

A. Construction of Joioba cDNA Libraries

RNA is isolated from jojoba embryos collected at 80–90 days post-anthesis using a polyribosome isolation method, initially described by Jackson and Larkins (*Plant Physiol.* (1976) 57:5–10), as modified by Goldberg et al. (*Developmental Biol.* (1981) 83:201–217). In this procedure all steps, unless specifically stated, are carried out at 4° C. 10 gm of tissue are ground in liquid nitrogen in a Waring blender until the tissue becomes a fine powder. After the liquid nitrogen has evaporated, 170 ml of extraction buffer (200 mM Tris pH 9.0, 160 mM KCl, 25 mM EGTA, 70 mM MgCl2, 1% Triton X-100, 0.05% sodium deoxycholate, 1 mM spermidine, 10 mM β-mercaptoethanol, and 500 mM sucrose) is added and the tissue is homogenized for about 2 minutes. The homogenate is filtered through sterile miracloth and centrifuged at 12,000×g for 20 minutes. The supernatant is decanted into a 500 ml sterile flask, and 1/19 volume of a 20% detergent solution (20% Brij 35, 20% Tween 40, 20% Noidet p-40 w/v) is added at room temperature. The solution is stirred at 4° C. for 30 minutes at a moderate speed and the supernatant is then centrifuged at 12,000×g for 30 minutes.

About 30 ml of supernatant is aliquoted into sterile Ti 60 centrifuge tubes and underlaid with 7 ml of a solution containing 40 mM Tris pH 9.0, 5 mM EGTA, 200 mM KCl, 30 mM MgCl2, 1.8M sucrose, 5 mM β-mercaptoethanol. The tubes are filled to the top with extraction buffer, and spun at 60,000 rpm for 4 hours at 4° C. in a Ti60 rotor. Following centrifugation, the supernatant is aspirated off and 0.5 ml of resuspension buffer (40 mM Tris pH 9.0, 5 mM EGTA, 200 mM KCl, 30 mM $MgCl_2$, 5 mM β-mercaptoethanol) is added to each tube. The tubes are placed on ice for 10 minutes, after which the pellets are thoroughly resuspended and pooled. The supernatant is then centrifuged at 120×g for 10 minutes to remove insoluble material. One volume of self-digested 1 mg/ml proteinase K in 20 mM Tris pH 7.6, 200 mM EDTA, 2% N-laurylsarcosinate is added to the supernatant and the mixture incubated at room temperature for 30 minutes.

RNA is precipitated by adding 1/10 volume of sodium acetate and 2 volumes of ethanol. After several hours at −20° C. RNA is pelleted by centrifugation at 12,000×g at 4° C for 30 minutes. The pellet is resuspended in 10 ml of TE buffer (10 mM Tris, 1 mM EDTA) and extracted with an equal volume of Tris pH 7.5 saturated phenol. The phases are separated by centrifuging at 10,000×g for 20 minutes at 4° C. The aqueous phase is removed and the organic phase is re-extracted with one volume of TE buffer. The aqueous phases are then pooled and extracted with one volume of chloroform. The phases are again separated by centrifugation and the aqueous phase ethanol precipitated as previously described, to yield the polyribosomal RNA.

Polysaccharide contaminants in the polyribosomal RNA preparation are removed by running the RNA over a cellulose column (Sigma-cell 50) in high salt buffer (0.5M NaCl, 20 mM Tris pH 7.5, 1 mM EDTA, 0.1% SDS). The contaminant binds to the column and the RNA is collected in the eluant. The eluant fractions are pooled and the RNA is ethanol precipitated. The precipitated total RNA is then resuspended in a smaller volume and applied to an oligo d(T) cellulose column to isolate the polyadenylated RNA.

Polyadenylated RNA is used to construct a cDNA library in the plasmid cloning vector pCGN1703, derived from the commercial cloning vector Bluescribe M13-(Stratagene Cloning Systems; San Diego, Calif.), and made as follows. The polylinker of Bluescribe M13- is alteredby digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with a synthetic linker having restriction sites for BamHI, PstI, XbaI, ApaI and SmaI, a 5' overhang of AATT, and a 3' overhang of TCGA. The insertion of the linker into pCGN1700 eliminates the EcoRI site, recreates the SstI (also, sometimes referred to as "SacI" herein) site found in Bluescribe, and adds the new restriction sites contained on the linker. The resulting plasmid pCGN1702, is digested with HindIII and blunt-ended with Klenow enzyme; the linear DNA is partially digested with PvuII and ligated with T4 DNA wax synthase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang stick-ends using terminal deoxynucleotidyl transferase. The tailed plasmid is separated from undigested or un-tailed plasmid by oligo(dA)-cellulose chromatography. The resultant vector serves as the primer for synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI stick-end at one end and a G-tail at the other. This complex is cyclized using an annealed synthetic cyclizing linker which has a 5' BamHI sticky-end, recognition sequences for restriction enzymes NotI, EcoRI and SstI, and a 3' C-tail end. Following ligation and repair the circular complexes are transformed into *E. coli* strain DH5α (BRL, Gaithersburg, Md.) to generate the cDNA library. The jojoba embryo cDNA bank contains between approximately $1.5 \times 10^6$ clones with an average cDNA insert size of approximately 500 base pairs.

Additionally, jojoba polyadenylated RNA is also used to construct a cDNA library in the cloning vector λZAPII/EcoRI (Stratagene, San Diego, Calif.). The library is constructed using protocols, DNA and bacterial strains as suppliedby the manufacturer. Clones are packaged using Gigapack Gold packaging extracts (Stratagene), also according to manufacturer's recommendations. The cDNA library constructed in this manner contains approximately $1 \times 10^6$ clones with an average cDNA insert size of approximately 400 base pairs.

B. Polymerase Chain Reaction

Using amino acid sequence information, nucleic acid sequences are obtained by polymerase chain reaction (PCR). Synthetic oligonucleotides are synthesized which correspond to the amino acid sequence of selected peptide fragments. If the order of the fragments in the protein is known, such as when one of the peptides is from the N-terminus or the selected peptides are contained on one long peptide fragment, only one oligonucleotide primer is needed for each selected peptide. The oligonucleotide primer for the more N-terminal peptide, forward primer, contains the encoding sequence for the peptide. The oligonucleotide primer for the more C-terminal peptide, reverse primer, is complementary to the encoding sequence for the selected peptide. Alternatively, when the order of the selected peptides is not known, two oligonucleotide primers are required for each peptide, one encoding the selected amino acid sequence and one complementary to the selected amino acid sequence. Any sequenced peptides may be selected for construction of oligonucleotides, although more desirable peptides are those which contain amino acids which are encoded by the least number of codons, such as methionine, tryptophan, cysteine, and other amino acids encoded by fewer than four codons. Thus, when the oligonucleotides are mixtures of all possible sequences for a selected peptide, the number of degenerate oligonucleotides may be low.

PCR is conducted with these oligonucleotide primers using techniques that are well known to those skilled in the art. Jojoba nucleic acid sequences, such as reverse transcribed cDNA, DNA isolated from the cDNA libraries described above or genomic DNA, are used as template in these reactions. In this manner, segments of DNA are produced. Similarly, segments of Acinetobacter w DNA are obtained from PCR reactions using oligonucleotide primers to the N-terminal and tryptic digest peptides described in Example 6A. The PCR products are analyzed by gel electrophoresis techniques to select those reactions yielding a desirable wax synthase fragment.

C. Screenina Libraries for Sequences

DNA fragments obtained by PCR are labeled and used as a probe to screen clones from the cDNA libraries described above. DNA library screening techniques are known to those in the art and described, for example in Maniatis et al. (*Molecular Cloning: A Laboratory Manual*, Second Edition (1989) Cold Spring Harbor Laboratory Press). In this manner, nucleic acid sequences are obtained which may be analyzed for nucleic acid sequence and used for expression of the plant cytoplasmic protein involved in fatty acyl-CoA metabolism in various hosts, both procaryotic and eucaryotic.

An approximately 1500 nucleotide jojoba cDNA clone is obtained in this manner. Comparison to the peptide fragments provided in Table 2 reveals the presence of each of these peptides in the translated sequence, with the exception of SQ1129. Northern analysis of jojoba embryo RNA indicates that the mRNA is approximately 2kb in length. Additional nucleic acid sequence is obtained using further PCR techniques, such as 5' RACE (Frohman et al., *Proc. Nat. Acad. Sci.* (1988) 85:8998-9002). Alternatively, additional sequences may be obtained by rescreening cDNA libraries or from genomic DNA. Preliminary DNA sequence of a jojoba gene is presented in FIG. 2. Further DNA sequence analysis of additional clones indicates that there are at least two classes of cDNA's encoding this jojoba protein. A plasmid containing the entire coding region in pCGN1703 is constructed to contain a SalI site approximately 8 nucleotides 5' to the ATG start codon, and is designated pCGN7614. The complete DNA sequence of pCGN7614 is presented in FIG. 3. The major difference between the two classes of cDNAs as represented in the sequences in FIGS. 2 and 3 is the presence (FIG. 2) or absence (FIG. 3) of the 6 nucleotide coding sequence for amino acids 23 and 24 of FIG. 2.

D. Expression of Wax Synthase Activity in *E. coli*

The gene from pCGN7614 is placed under the control of the Tac promoter of *E. coli* expression vector pDR540 (Pharmacia) as follows. pCGN7614 DNA is digested at the SalI sites and the ends are partially filled in using the Klenow fragment of DNA polymerase I and the nucleotides TTP and dCTP. The pDR540 vector is prepared by digesting with BamHI and partially filling in the ends with dGTP and dATP. The 1.8 kb fragment from pCGN7614 and the digested pDR540 vector are gel purified using low melting temperature agarose and ligated together using T4 DNA ligase. A colony containing the encoding sequence in the sense orientation relative to the *E. coli* promoter was designated pCGN7620, and a colony containing the gene in the antisense orientation was designated pCGN7621.

To assay for wax synthase activity, 50 ml cultures of pCGN7620 and pCGN7621 are grown to log phase in liquid culture, and induced for 2 hours by the addition of IPTG to a concentration of 1 mM. The cells are harvested by centrifugation and subjected to the assay for wax synthase activity as described for jojoba extracts. TLC analysis indicates that the cell extract from pCGN7620 directs synthesis of wax ester, while the control extract from pCGN7621 does not direct the synthesis of wax ester. The wax synthase assay in these harvested cells was verified by a second assay, however, further attempts to produce wax synthase activity in *E. coli* cells transformed with reductase constructs have been unsuccessful.

Example 8—Constructs for Plant Expression

Constructs which provide for expression of the plant cytoplasmic protein involved in fatty acyl-CoA metabolism and reductase sequences in plant cells may be prepared as follows.

A. Expression Cassettes

Expression cassettes which contain 5' and 3' regulatory regions from Genes expressed preferentially in seed tissues may be prepared from napin, Bce4 and ACP genes as described, for example in WO 92/03564.

For example, napin expression cassettes may be prepared as follows. A napin expression cassette, pCGN1808, which may be used for expression of wax synthase or reductase gene constructs is described in Kridl et al. (*Seed Science Research* (1991) 1:209-219), which is incorporated herein by reference.

Alternatively, pCGN1808 may be modified to contain flanking restriction sites to allow movement of only the expression sequences and not the antibiotic resistance marker to binary vectors such as pCGN1557 (McBride and Summerfelt, supra). Synthetic oligonucleotides containing KpnI, NotI and HindIII restriction sites are annealed and ligated at the unique HindIII site of pCGN1808, such that only one HindIII site is recovered. The resulting plasmid, pCGN3200 contains unique HindIII, NotI and KpnI restriction sites at the 3'-end of the napin 3'-regulatory sequences as confirmed by sequence analysis.

The majority of the napin expression cassette is subcloned from pCGN3200 by digestion with HindIII and SacI and ligation to HindIII and SacI digested pIC19R (Marsh, et al. (1984) *Gene* 32:481–485) to make pCGN3212. The extreme 5'-sequences of the napin promoter region are reconstructed by PCR using pCGN3200 as a template and two primers flanking the SacI site and the junction of the napin 5'-promoter and the pUC backbone of pCGN3200 from the pCGN1808 construct. The forward primer contains ClaI, HindIII, NotI, and KpnI restriction sites as well as nucleotides 408–423 of the napin 5'-sequence (from the EcoRV site) and the reverse primer contains the complement to napin sequences 718–739 which include the unique SacI site in the 5'-promoter. The PCR was performed using a Perkin Elmer/Cetus thermocycler according to manufacturer's specifications. The PCR fragment is subcloned as a blunt-ended fragment into pUC8 (Vieira and Messing (1982) *Gene* 9:259–268) and digested with HincII to give pCGN3217. Sequence of pCGN3217 across the napin insert verifies that no improper nucleotides were introduced by PCR. The napin 5-sequences in pCGN3217 are ligated to the remainder of the napin expression cassette by digestion with ClaI and SacI and ligation to pCGN3212 digested with ClaI and SacI. The resulting expression cassette pCGN3221, is digested with HindIII and the napin expression sequences are gel purified away and ligated to pIC20H (Marsh, supra) digested with HindIII. The final expression cassette is pCGN3223, which contains in an ampicillin resistant background, essentially identical 1,725 napin 5' and 1.265 3' regulatory sequences as found in pCGN1808. The regulatory regions are flanked with HindIII, NotI and KpnI restriction sites and unique SalI, BglII, PstI, and XhoI cloning sites are located between the 5' and 3 noncoding regions.

Similarly, a cassette for cloning of sequences for transcription regulation under the control of 5' and 3' regions from an oleosin gene may be prepared. Sequence of a *Brassica napus* oleosin gene was reported by Lee and Huang (Plant Phys. (1991) 96:1395–1397). Primers to the published sequence are used in PCR reactions to obtain the 5' and 3' regulatory regions of an oleosin gene from *Brassica napus* cv. Westar. Two PCR reactions were performed, one to amplify approximately 950 nucleotides upstream of the ATG start codon for the oleosin gene, and one to PCR amplify approximately 600 bp including and downstream of the TAA stop codon for the oleosin gene. The PCR products were cloned into plasmid vector pAMP1 (BRL) according to manufacturers protocols to yield plasmids pCGN7629 which contains the oleosin 5' flanking region and pCGN7630 which contains the 3' flanking region. The PCR primers included convenient restriction sites for cloning the 5' and 3' flanking regions together into an expression cassette. A PstI fragment containing the 5' flanking region from pCGN7629 was cloned into PstI digested pCGN7630 to yield plasmid pCGN7634. The BssHII (New England BioLabs) fragment from pCGN7634, which contains the entire oleosin expression cassette was cloned into BssHII digested pBCSK+ (Stratagene) to provide the oleosin cassette in a plasmid, pCGN7636. Sequence of the oleosin cassette in pCGN7636 is provided in FIG. 4. The oleosin cassette is flanked by BssHII, KpnI and XbaI restriction sites, and contains SalI, BamHI and PstI sites for insertion of wax synthase, reductase, or other DNA sequences of interest between the 5' and 3' oleosin regions.

The gene sequences are inserted into such cassettes to provide expression constructs for plant transformation methods. For example, such constructs may be inserted into binary vectors for Agrobacterium-mediated transformation as described below.

B. Constructs for Plant Transformation

The plasmid pCGN7614 is digested with AflIII, and ligated with adapters to add BclI sites to the AflIII sticky ends, followed by digestion with SalI and BclI. The fragment containing the plant cytoplasmic protein involved in fatty acyl-CoA metabolism gene is gel purified and cloned into SalI/BamHI digested pCGN3223, a napin expression cassette. The resulting plasmid which contains the plant cytoplasmic protein involved in fatty acyl-CoA metabolism gene in a sense orientation in the napin expression cassette is designated pCGN7624. DNA isolated from pCGN7624 is digested with Asp718 (a KpnI isoschizimer), and the napin/plant cytoplasmic protein involved in fatty acyl-CoA metabolism fusion gene is cloned into Asp718 digested binary vector pCGN1578 (McBride and Summerfelt, supra). The resultant binary vector, designated pCGN7626, is transformed into Agrobacterium strain EHA101 and used for transformation of Arabidopsis and rapeseed explants.

Additional binary vectors are prepared from pCGN1578, pCGN1559 and other vectors described by McBride et al. (supra) by substitution of the pCGN1578 and pCGN1559 linker regions with a linker region containing the following restriction digestion sites: Asp718/AscI/PacI/XbaI/BamHI/SwaI/Sse8387 (PstI)/HindIII. This results in pCGN1578PASS or pCGN1559PASS, and other modified vectors which are designated similarly. AscI, PacI, SwaI and Sse8387 have 8-base restriction recognition sites. These enzymes are available from New England BioLabs: AscI, PacI; Boehringer Manheim: SwaI and Takara (Japan): Sse8387.

C. Reductase Constructs for Plant Transformation

Constructs for expression of reductase in plant cells using 5' and 3' regulatory regions from a napin gene, are prepared.

A reductase cDNA (in the pCGN1703 vector described above) designated pCGN7571, is digested with SphI (site in 3' untranslated sequence at bases 1594–1599) and a SalI linker is inserted at this site. The resulting plasmid is digested with BamHI and SalI and the fragment containing the reductase cDNA gel purified and cloned into BglII/XhoI digested pCGN3223, the napin cassette described above, resulting in pCGN7585.

A HindIII fragment of pCGN7585 containing the napin 5'/reductase/napin 3' construct is cloned into HindIII digested pCGN1578 (McBride and Summerfelt, supra), resulting in pCGN7586, a binary vector for plant transformation.

Plant transformation construct pCGN7589, also containing the jojoba reductase gene under expression of a napin promoter, is prepared as follows. pCGN7571 is in vitro mutagenized to introduce an NdeI site at the first ATG of the reductase coding sequence and a BglII site immediately upstream of the NdeI site. BamHI linkers are introduced into the SphI site downstream of the reductase coding region. The 1.5 kb BglII-BamHI fragment is gel purified and cloned into BglII-BamHI digested pCGN3686 (see below), resulting in pCGN7582.

pCGN3686 is a cloning vector derived from Bluescript KS+ (Stratagene Cloning Systems; San Diego, Calif.), but having a chloramphenicol resistance gene and a modified linker region. The source of the chloramphenicol resistance gene, pCGN565 is a cloning vector based on pUC12-cm (K. Buckley Ph.D. Thesis, Regulation and expression of the phi X174 lysis gene, University of California, San Diego, 1985), but containing pUC18 linkers (Yanisch-Perron, et al., *Gene* (1985) 53:103–119). pCGN565 is digested with HhaI and the fragment containing the chloramphenicol resistance gene is excised, blunted by use of mung bean nuclease, and inserted into the EcoRV site of Bluescript KS-(Stratagene: La Jolla, Calif.) to create pCGN2008. The chloramphenicol resistance gene of pCGN2008 is removed by EcoRI/HindIII digestion. After treatment with Klenow enzyme to blunt the ends, the fragment is ligated to DraI digested Bluescript KS+. A clone that has the DraI fragment containing ampicillin resistance replaced with the chloramphenicol resistance is chosen and named pCGN2015. The linker region of pCGN2015 is modified to provide pCGN3686, which contains the following restriction digestion sites, 5' to 3' in the lacZ linker region: PstI, BglII, XhoI, HincII, SalI, HindIII, EcoRV, EcoRI, PstI, Sinai, BamHi, SpeI, XbaI and SacI.

An XhoI linker is inserted at the XbaI site of pCGN7582. The BglII-XhoI fragment containing the reductase gene is isolated and cloned into BglII-XhoI digested pCGN3223. The resulting plasmid, which lacks the 5' untranslated leader sequence from the jojoba gene, is designated pCGN7802. The napin/reductase fragment from pCGN7802 is excised with HindIII and cloned into HindIII digested pCGN1578 to yield pCGN7589.

An additional napin/reductase construct is prepared as follows. The reductase cDNA pCGN7571 (FIG. 1) is mutagenized to insert SalI sites 5' to the ATG start codon (site is 8 base pairs 5' to ATG) and immediately 3' to the TAA translation stop codon, resulting in pCGN7631. pCGN7631 is digested with SalI and the approximately 1.5 kb fragment containing the reductase encoding sequence is cloned into SalI/XhoI digested napin cassette pCGN3223. A resulting plasmid containing the reductase sequence in the sense orientation is designated pCGN7640. pCGN7640 is digested with HindIII, and the fragment containing the oleosin/reductase construct is cloned into HindIII digested binary vector pCGN1559PASS, resulting in binary construct pCGN7642.

A construct for expression of reductase under control of oleosin regulatory regions is prepared as follows. The reductase encoding sequence is obtained by digestion of pCGN7631 with SalI, and ligated into SalI digested pCGN7636, the oleosin cassette. A resulting plasmid containing the reductase sequence in the sense orientation is designated pCGN7641. pCGN7641 is digested with XbaI, and the fragment containing the oleosin/reductase construct is cloned into XbaI digested binary vector pCGN1559PASS, resulting in binary construct pCGN7643.

Binary vector constructs are transformed into Agrobacterium cells, such as of strain EHA101 (Hood et al., *J. Bacteriol* (1986) 168:1291–1301), by the method of Holsters et al. (*Mol. Gen. Genet.* (1978) 163:181–187) and used in plant transformation methods as described below.

Example 9—Plant Transformation Methods

A variety of methods have been developed to insert a DNA sequence of interest into the genome of a plant host to obtain the transcription or transcription and translation of the sequence to effect phenotypic changes.

Brassica Transformation

Seeds of high erucic acid, such as cultivar Reston, or Canola-type varieties of Brassica napus are soaked in 95% ethanol for 2 min. surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco; Grand Island, N.Y.) supplemented with pyriodoxine (50 µg/l), nicotinic acid (50 µg/l), glycine (200 µg/l), and 0.6% Phytagar (Gibco) pH 5.8. Seeds are germinated in a Percival chamber at 22° C. in a 16 h photoperiod with cool fluorescent and red light of intensity approximately 65µ Einsteins per square meter per second ($\mu Em^{-2}S^{-1}$).

Hypocotyls are excised from 5–7 day old seedlings, cut into pieces approximately 4 mm in length, and plated on feeder plates (Horsch et al., Science (1985) 227:1229–1231). Feeder plates are prepared one day before use by plating 1.0 ml of a tobacco suspension culture onto a petri plate (100×25 mm) containing about 30 ml MS salt base (Carolina Biological, Burlington, N.C.) 100 mg/l inositol, 1.3 mg/l thiamine-HCl, 200 mg $KH_2PO_4$ with 3% sucrose, 2,4-D (1.0 mg/l), 0.6% w/v Phytagar, and pH adjusted to 5.8 prior to autoclaving (MS 0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1 mg/l). In experiments where feeder cells are not used hypocotyl explants are cut and placed onto a filter paper disc on top of MS0/1/0 medium. All hypocotyl explants are preincubated on feeder plates for 24 h. at 22° C. in continuous light of intensity 30 $\mu Em^{-2}S^{-1}$ to 65 $\mu EM^{-2}S^{-1}$.

Single colonies of A. tumefaciens strain EHA101 containing a binary plasmid with the desired gene construct are transferred to 5 ml MG/L broth and grown overnight at 30° C. Hypocotyl explants are immersed in 7–12 ml MG/L broth with bacteria diluted to $1 \times 10^8$ bacteria/ml and after 10–25 min. are placed onto feeder plates. Per liter MG/L broth contains 5 g mannitol, 1 g L-Glutamic acid or 1.15 g sodium glutamate, 0.25 g $kH_2PO_4$, 0.10 g NaCl, 0.10 g $MGSO_4 \cdot 7H_2O$, 1 mg biotin, 5 g tryptone, and 2.5 g yeast extract, and the broth is adjusted to pH 7.0. After 48 hours of co-incubation with Agrobacterium, the hypocotyl explants are transferred to B5 0/1/0 callus induction medium which contains filter sterilized carbenicillin (500 mg/l, added after autoclaving) and kanamycin sulfate (Boehringer Mannheim; Indianapolis, Ind.) at concentrations of 25 mg/1.

After 3–7 days in culture at 65 $\mu EM^{-2}S^{-1}$ continuous light, callus tissue is visible on the cut surface and the hypocotyl explants are transferred to shoot induction medium, B5BZ (B5 salts and vitamins supplemented with 3 mg/1 benzylaminopurine, 1 mg/l zeatin, 1% sucrose, 0.6% Phytagar and pH adjusted to 5.8). This medium also contains carbenicillin (500 mg/l) and kanamycin sulfate (25 mg/l). Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% w/v Phytagar). After 2–4 weeks shoots which remain green are cut at the base and transferred to Magenta boxes containing root induction medium (B5 salts and vitamins, 1% sucrose, 2 mg/1 indolebutyric acid, 50 mg/1 kanamycin sulfate and 0.6% Phytagar). Green rooted shoots are tested for thioesterase activity.

Arabidposis Transformation

Transgenic Arabidopsis thaliana plants may be obtained by Agrobacterium-mediated transformation as described by Valverkens et al., (Proc. Nat. Acad. Sci. (1988) 85:5536–5540). Constructs are transformed into Agrobacterium cells, such as of strain EHA101 (Hood et al., J. Bacteriol (1986) 168:1291–1301), by the method of Holsters et al. (Mol. Gen. Genet. (1978) 163:181–187).

Peanut Transformation

DNA sequences of interest may be introduced as expression cassettes, comprising at least a promoter region, a gene of interest, and a termination region, into a plant genome via particle bombardment.

Briefly, tungsten or gold particles of a size ranging from 0.5 mM–3 mM are coated with DNA of an expression cassette. This DNA may be in the form of an aqueous mixture or a dry DNA/particle precipitate.

Tissue used as the target for bombardment may be from cotyledonary explants, shoot meristems, immature leaflets, or anthers. The bombardment of the tissue with the DNA-coated particles is carried out using a Biolistics™ particle gun (Dupont; Wilmington, Del.). The particles are placed in the barrel at variable distances ranging from 1 cm–14 cm from the barrel mouth. The tissue to be bombarded is placed beneath the stopping plate; testing is performed on the tissue at distances up to 20 cm. At the moment of discharge, the tissue is protected by a nylon net or a combination of nylon nets with mesh ranging from 10 mM to 300 mM.

Following bombardment, plants may be regenerated following the method of Atreya, et al., (Plant Science Letters (1984) 34:379–383). Briefly, embryo axis tissue or cotyledon segments are placed on MS medium (Murashige and Skoog, Physio. Plant. (1962) 15:473) (MS plus 2.0 mg/l 6-benzyladenine (BA) for the cotyledon segments) and incubated in the dark for 1 week at 25°±2° C. and are subsequently transferred to continuous cool white fluorescent light (6.8 W/m²). On the 10th day of culture, the plantlets are transferred to pots containing sterile soil, are kept in the shade for 3–5 days are and finally moved to greenhouse. The putative transgenic shoots are rooted. Integration of exogenous DNA into the plant genome may be confirmed by various methods know to those skilled in the art.

Example 10—Analysis of Transformed Plants for Wax Production

Seeds or other plant material from transformed plants may be analyzed for wax synthase activity using the wax synthase assay methods described in Example 1.

Plants which have beth the reductase and wax synthase constructs are also assayed to measure wax production. Such plants may be prepared by Agrobacterium transformation methods as described above. Plants having both of the desired gene constructs may be prepared by co-transformation with reductase and wax synthase constructs or by combining the wax synthase and reductase constructs on a single plant transformation binary vector. In addition, re-transformation of either wax synthase expressing plants or reductase expressing plants with constructs encoding the other desired gene sequence may also be used to provide such reductase and wax synthase expressing plants. Alternatively, transgenic plants expressing reductase produced by methods described herein may be crossed with plants expressing wax synthase which have been similarly produced. In this manner, known methods of plant breeding are used to provide reductase and wax synthase expressing transgenic plants.

Such plants may be assayed for the presence of wax esters, for example by separation of TAG from wax esters as described by Tani et al. (supra). GC analysis methods may be used to further analyze the resulting waxes, for example as described by Pina et al. (Lipids (1987) 22(5):358–361.

The above results demonstrate the ability to obtain partially purified wax synthase proteins which are active in the formation of wax esters from fatty alcohol and fatty acyl substrates. Methods to obtain the wax synthase proteins and amino acid sequences thereof are provided. In addition wax synthase nucleic acid sequences obtained from the amino acid sequences are also provided. These nucleic acid sequences may be manipulated to provide for transcription of the sequences and/or expression of wax synthase proteins in host cells, which proteins may be used for a variety of applications. Such applications include the production of wax ester compounds when the wax synthase is used in host cells having a source of fatty alcohol substrates, which substrates may be native to the host cells or supplied by use of recombinant constructs encoding a fatty acyl reductase protein which is active in the formation of alcohols from fatty acyl substrates.

Example 11—Analysis of Transformed Plants for VLCFA Production

Seeds from transformed plants are analyzed by gas chromatography (GC) for fatty acid content. The following tables provide breakdowns of fatty acids on a percentage basis, demonstrating altered VLCFA production in plants transformed with binary vector pCGN7626 (Example 8).

Table 3

Seeds from canoa plants, some transformed by pCGN7626, showing percentage of fatty acids of a given carbon chain length:saturation. Twenty seeds were pooled for each plant and fatty acids determined by gas chromatography.

Control canola plants (plants 1 and 2 of Table 3 contain less than 2% VLCFA in their seed oil. Plants 3 through 20 in Table 3 are transgenic. The majority (14/18) of the plants transformed with pCGN7626 have significantly higher levels of VLCFA. The VLCFA for the highly expresssing transgenics range from about 5% to about 22% of the total fatty acids.

TABLE 3

| NO | % 18:0 | % 18:1 | % 18:2 | % 18:3 | % 20:0 | % 20:1 | % 20:2 | % 22:0 | % 22:1 | % 22:2 |
|---|---|---|---|---|---|---|---|---|---|---|
| 1 | 1.30 | 58.42 | 21.14 | 12.48 | 0.45 | 1.20 | 0.08 | 0.24 | 0.01 | 0.00 |
| 2 | 1.12 | 58.89 | 22.09 | 11.25 | 0.41 | 1.31 | 0.09 | 0.25 | 0.01 | 0.00 |
| 3 | 1.11 | 52.01 | 19.24 | 15.95 | 0.46 | 4.97 | 0.33 | 0.24 | 0.47 | 0.01 |
| 4 | 0.76 | 38.12 | 19.60 | 14.57 | 0.49 | 14.27 | 1.11 | 0.39 | 4.84 | 0.66 |
| 5 | 0.90 | 46.74 | 18.76 | 14.89 | 0.49 | 9.75 | 0.67 | 0.31 | 1.73 | 0.21 |
| 6 | 0.95 | 51.00 | 20.34 | 13.74 | 0.46 | 6.93 | 0.47 | 0.27 | 0.88 | 0.02 |
| 7 | 0.99 | 52.36 | 19.40 | 14.90 | 0.44 | 5.41 | 0.35 | 0.34 | 0.49 | 0.01 |
| 8 | 1.10 | 60.63 | 19.52 | 11.20 | 0.45 | 1.27 | 0.09 | 0.31 | 0.01 | 0.00 |
| 9 | 0.91 | 47.57 | 20.51 | 16.15 | 0.45 | 7.24 | 0.53 | 0.24 | 1.39 | 0.02 |
| 10 | 0.93 | 48.91 | 20.48 | 15.52 | 0.44 | 6.72 | 0.48 | 0.24 | 0.88 | 0.08 |
| 11 | 1.16 | 53.17 | 21.44 | 16.83 | 0.41 | 1.25 | 0.10 | 0.25 | 0.00 | 0.01 |
| 12 | 0.94 | 48.04 | 22.28 | 17.50 | 0.39 | 4.88 | 0.41 | 0.28 | 0.46 | 0.02 |
| 13 | 1.07 | 56.23 | 21.08 | 14.35 | 0.43 | 1.35 | 0.11 | 0.26 | 0.01 | 0.00 |
| 14 | 0.88 | 53.08 | 20.93 | 15.39 | 0.39 | 1.17 | 0.04 | 0.34 | 0.00 | 0.01 |
| 15 | 0.89 | 47.06 | 20.65 | 19.78 | 0.39 | 4.19 | 0.34 | 0.26 | 0.46 | 0.02 |
| 16 | 0.93 | 46.98 | 23.86 | 15.51 | 0.47 | 5.03 | 0.47 | 0.33 | 0.69 | 0.08 |
| 17 | 1.26 | 53.62 | 20.04 | 14.89 | 0.47 | 3.86 | 0.24 | 0.26 | 0.25 | 0.00 |
| 18 | 1.02 | 52.20 | 19.57 | 15.20 | 0.43 | 5.13 | 0.31 | 0.26 | 0.44 | 0.01 |
| 19 | 1.14 | 53.74 | 19.77 | 15.09 | 0.43 | 3.77 | 0.25 | 0.22 | 0.26 | 0.02 |
| 20 | 0.92 | 44.57 | 20.15 | 22.87 | 0.36 | 4.48 | 0.41 | 0.15 | 0.58 | 0.02 |

Table 4

Canola plants, some transformed by pCGN7626, showing percentage of fatty acids of a given carbon chain length-:saturation.

Plants 1 and 2 in Table 4 are controls. Plant 3 is a repeat of plant 4 of Table 3. Plants 4 through 13 are seed of plants grown out from the seed of a single canola plant transformed by pCGN7626, showing inheritance of the altered VLCFA phenotype. One plant, plant 11, did not inherit the altered phenotype. This plant also did not show inheritance of the transgens by a Kan germination assay.

TABLE 4

| NO | % 18:0 | % 18:1 | % 18:2 | % 18:3 | % 20:0 | % 20:1 | % 20:2 | % 22:0 | % 22:1 | % 22:2 | % 24:0 | % 24:1 |
|---|---|---|---|---|---|---|---|---|---|---|---|---|
| 1 | 1.25 | 58.14 | 21.16 | 11.87 | 0.43 | 1.19 | 0.08 | 0.25 | 0.00 | 0.00 | 0.01 | 0.01 |
| 2 | 1.02 | 58.73 | 22.38 | 10.71 | 0.42 | 1.30 | 0.09 | 0.26 | 0.01 | 0.00 | 0.01 | 0.10 |
| 3 | 0.80 | 36.80 | 20.37 | 15.92 | 0.51 | 12.31 | 1.05 | 0.39 | 3.93 | 0.58 | 0.24 | 0.67 |
| 4 | 0.98 | 43.21 | 20.97 | 16.61 | 0.50 | 7.70 | 0.63 | 0.34 | 1.78 | 0.22 | 0.18 | 0.41 |
| 5 | 0.87 | 42.48 | 23.36 | 13.39 | 0.46 | 8.83 | 0.76 | 0.31 | 1.76 | 0.25 | 0.21 | 0.36 |
| 6 | 0.87 | 44.00 | 22.75 | 13.91 | 0.45 | 8.67 | 0.66 | 0.29 | 1.56 | 0.20 | 0.04 | 0.43 |
| 7 | 0.96 | 43.13 | 22.15 | 16.31 | 0.46 | 7.80 | 0.64 | 0.29 | 1.27 | 0.17 | 0.01 | 0.32 |
| 8 | 1.17 | 48.73 | 20.34 | 14.36 | 0.53 | 6.83 | 0.47 | 0.31 | 0.84 | 0.09 | 0.21 | 0.24 |
| 9 | 0.97 | 52.27 | 23.14 | 13.22 | 0.39 | 3.48 | 0.24 | 0.24 | 0.27 | 0.01 | 0.01 | 0.03 |
| 10 | 1.12 | 46.79 | 21.21 | 13.53 | 0.55 | 7.68 | 0.54 | 0.33 | 1.08 | 0.12 | 0.19 | 0.36 |
| 11 | 0.98 | 51.73 | 24.05 | 14.91 | 0.41 | 1.18 | 0.11 | 0.28 | 0.01 | 0.00 | 0.02 | 0.00 |
| 12 | 1.10 | 44.56 | 23.03 | 14.04 | 0.50 | 7.58 | 0.62 | 0.29 | 1.76 | 0.23 | 0.26 | 0.59 |
| 13 | 0.88 | 41.32 | 24.20 | 14.92 | 0.47 | 7.62 | 0.79 | 0.34 | 1.83 | 0.32 | 0.04 | 0.37 |

Table 5

The results of measurements of seeds of HEAR plants, controls and pCGN7626 transgenic, evaluated for VLCFA content. Pools of twenty seeds were analyzed by GC.

Plants 1 and 2 are control HEAR plants. The remaining plants are transgenic. Control HEAR (variety Reston) has 22:1 levels between 33 and 41 percent of its fatty acids with 24:1 comprising about 0.1 to 0.5%. The results show significant alteration of the VLCFA patterns. Plants 3, 4, 7, 12–14 and 16–19 particularly showed an increase in 24:1 content, with one transgenic plant showing a 24:1 level of 2.7% of the seed oil.

Table 6

Arabidopsis thaliana plants transformed with pCGN7626. Arabidopsis thaliana typically has seed oil with 21% 20:1 fatty acid, 2% 22:1 fatty acid, 0.02% 24:1 fatty acid (control plants 1–3). The oil composition of plants transformed with pCGN7626 (plants 4–12) is shifted towards the longer chain fatty acids at the expense of 20:1. The 20:1 in transgenic plants decreased to as low as 15.5% while the 22:1 percentage increased to as high as 7.5%. In one transgenic plant the 24:1 content increased to 1.6% of the total fatty acids in the seed oil.

TABLE 5

| NO | % 18:0 | % 18:1 | % 18:2 | % 18:3 | % 20:0 | % 20:1 | % 20:2 | % 22:0 | % 22:1 | % 22:2 | % 24:0 | % 24:1 |
|---|---|---|---|---|---|---|---|---|---|---|---|---|
| 1 | 0.90 | 13.69 | 18.07 | 12.32 | 0.46 | 6.00 | 0.75 | 0.48 | 40.57 | 0.78 | 0.03 | 0.12 |
| 2 | 1.03 | 19.90 | 18.49 | 9.74 | 0.46 | 8.36 | 0.68 | 0.28 | 33.57 | 0.45 | 0.01 | 0.66 |
| 3 | 1.06 | 12.94 | 17.45 | 12.68 | 0.45 | 5.22 | 0.80 | 0.81 | 38.32 | 1.72 | 0.06 | 2.69 |
| 4 | 0.96 | 13.39 | 19.74 | 11.29 | 0.48 | 6.60 | 0.90 | 0.54 | 37.84 | 1.16 | 0.05 | 1.21 |
| 5 | 1.05 | 13.85 | 19.55 | 12.77 | 0.42 | 6.32 | 0.95 | 0.53 | 37.16 | 1.22 | 0.06 | 0.13 |
| 6 | 1.04 | 14.56 | 19.29 | 11.26 | 0.44 | 6.49 | 0.93 | 0.47 | 38.29 | 1.27 | 0.05 | 0.14 |
| 7 | 1.03 | 15.03 | 18.35 | 11.73 | 0.48 | 6.68 | 0.80 | 0.44 | 37.38 | 0.95 | 0.02 | 1.41 |
| 8 | 1.02 | 16.14 | 18.67 | 10.60 | 0.44 | 7.51 | 0.86 | 0.41 | 37.02 | 0.62 | 0.00 | 0.09 |
| 9 | 1.17 | 17.00 | 18.99 | 11.03 | 0.56 | 6.05 | 0.70 | 0.61 | 36.48 | 0.96 | 0.04 | 0.13 |
| 10 | 1.01 | 18.78 | 18.22 | 10.25 | 0.51 | 8.48 | 0.72 | 0.06 | 34.55 | 0.59 | 0.02 | 0.10 |
| 11 | 0.92 | 14.36 | 20.64 | 12.52 | 0.35 | 5.85 | 0.84 | 0.37 | 35.82 | 0.73 | 0.03 | 0.75 |
| 12 | 0.99 | 17.10 | 18.19 | 10.10 | 0.46 | 7.23 | 0.68 | 0.47 | 36.34 | 0.92 | 0.03 | 1.43 |
| 13 | 0.95 | 17.99 | 19.65 | 10.01 | 0.47 | 6.97 | 0.78 | 0.49 | 33.93 | 0.72 | 0.02 | 1.39 |
| 14 | 0.87 | 16.02 | 18.67 | 10.92 | 0.41 | 7.39 | 0.87 | 0.43 | 35.69 | 1.16 | 0.05 | 1.58 |
| 15 | 1.01 | 45.08 | 22.48 | 16.95 | 0.35 | 5.88 | 0.54 | 0.17 | 0.78 | 0.02 | 0.01 | 0.03 |
| 16 | 0.94 | 14.92 | 16.48 | 10.86 | 0.45 | 6.30 | 0.78 | 0.77 | 39.10 | 1.56 | 0.03 | 2.53 |
| 17 | 0.93 | 15.40 | 19.23 | 10.79 | 0.51 | 6.10 | 0.79 | 0.60 | 36.76 | 1.12 | 0.02 | 1.46 |
| 18 | 1.04 | 16.35 | 18.31 | 9.42 | 0.52 | 7.17 | 0.87 | 0.60 | 37.05 | 1.10 | 0.04 | 1.30 |
| 19 | 0.99 | 14.82 | 16.50 | 11.43 | 0.53 | 7.16 | 0.83 | 0.68 | 38.53 | 1.24 | 0.03 | 1.85 |

TABLE 6

| NO | % 18:0 | % 18:1 | % 18:2 | % 18:3 | % 20:0 | % 20:1 | % 20:2 | % 22:0 | % 22:1 | % 22:2 | % 24:0 | % 24:1 |
|---|---|---|---|---|---|---|---|---|---|---|---|---|
| 1 | 2.88 | 17.24 | 26.82 | 18.08 | 2.17 | 20.84 | 2.03 | 0.33 | 2.07 | 0.04 | 0.01 | 0.03 |
| 2 | 3.55 | 18.27 | 25.24 | 18.61 | 2.22 | 20.95 | 1.83 | 0.26 | 1.80 | 0.02 | 0.01 | 0.01 |
| 3 | 2.91 | 17.61 | 26.18 | 18.30 | 2.07 | 21.02 | 2.02 | 0.10 | 2.00 | 0.02 | 0.05 | 0.05 |
| 4 | 3.65 | 17.97 | 26.46 | 18.67 | 1.99 | 20.70 | 1.77 | 0.06 | 1.58 | 0.02 | 0.05 | 0.03 |
| 5 | 2.88 | 15.79 | 25.51 | 20.80 | 1.85 | 18.58 | 1.97 | 0.85 | 4.03 | 0.32 | 0.07 | 0.74 |

TABLE 6-continued

| NO | % 18:0 | % 18:1 | % 18:2 | % 18:3 | % 20:0 | % 20:1 | % 20:2 | % 22:0 | % 22:1 | % 22:2 | % 24:0 | % 24:1 |
|---|---|---|---|---|---|---|---|---|---|---|---|---|
| 6 | 2.78 | 15.41 | 24.64 | 20.19 | 1.97 | 17.55 | 1.97 | 0.74 | 3.36 | 0.04 | 0.51 | 0.42 |
| 7 | 2.83 | 19.55 | 26.43 | 18.80 | 1.84 | 20.30 | 1.64 | 0.04 | 1.92 | 0.01 | 0.02 | 0.04 |
| 8 | 2.17 | 15.33 | 25.62 | 20.56 | 1.56 | 15.66 | 1.80 | 1.29 | 5.72 | 0.69 | 1.11 | 1.55 |
| 9 | 3.34 | 15.11 | 25.89 | 19.48 | 2.05 | 19.58 | 2.03 | 0.44 | 2.60 | 0.12 | 0.03 | 0.04 |
| 10 | 2.69 | 14.90 | 26.10 | 20.51 | 1.83 | 18.17 | 2.01 | 0.90 | 3.98 | 0.40 | 0.84 | 0.67 |
| 11 | 1.86 | 16.65 | 25.91 | 18.45 | 1.55 | 15.69 | 1.84 | 1.49 | 7.47 | 0.73 | 0.09 | 1.40 |
| 12 | 1.94 | 17.82 | 24.95 | 19.91 | 1.42 | 15.52 | 1.44 | 1.34 | 6.40 | 0.43 | 1.06 | 1.60 |

These data clearly show that the plant cytoplasmic protein involved in fatty acyl-CoA metabolism encoded by pCGN7626 can markedly alter the fatty acid composition of seed oil from several plant species. In plants that do not accumulate VLCFA, pCGN7626 causes the accumulation of significant quantities of VLCFA. In plants that do accumulate VLCFA, pCGN7626 shifts the fatty acid composition towards longer VLCFA.

When searching protein data bases for the jojoba protein sequence disclosed herein, a large region of homology was found between the jojoba encoded protein and stilbene, reservatrol, and chalcone synthase. Stilbene, reservatrol and chalcone synthases are very similar to each other, catalyzing multiple condensing reactions between two CoA thioesters, with malonyl CoA as one subtrate. The condensing reactions are similar to the proposed condensing reaction for the cytoplasmic membrane bound elongase enzymes, in that in both cases an enzyme condenses two CoA thioester molecules to form two products: a β-ketoacyl-CoA thioester and a carbon dioxide. The region of homology between the jojoba gene and chalcone synthase includes the chalcone synthase active site (Lanz et al. "Site-directed mutagenesis of reservatrol and chalcone synthase, two key enzymes in different plant specific pathways" (1991) *J. Biol. Chem.*, 266:9971–6). This active site is postulated to be involved in forming an enzyme-fatty acid intermediate.

Homology was also detected between the jojoba protein and KASIII. KASIII is a soluble enzyme which catalyzes the condensation of a CoA thioester to an ACP thioester, resulting in a β-ketoacyl-ACP thioester. A carbon dioxide molecule is released in this reaction.

While not concusive, these noted homologies suggest that the jojoba enzyme may have β-ketoacyl-CoA synthase activity.

Example 12—Analysis of Plants By a β-Keto-acyl-CoA Synthase Assay

A. The activity of β-Keto-acyl-CoA synthase may be directly assayed in plants according to the following procedure.

Developing seeds are harvested after pollination and frozen at −70°C. For *Brassica napus*, the seeds are harvested 29 days after pollination. An appropriate number of seeds are thawed and homogenized in 1 ml 50 mM Hepes-NaOH, pH 7.5, 2 mM EDTA, 250 mM NaCl, 5 mM b-mercaptoethanol (twenty seeds per assay for *Brassica napus*). The homogenate is centrifuged at 15,000×g for 10 min, and the oil layer is discarded. The supernatant fraction is collected and centifuged again at 200,000×g for 1 hour.

The pellet is then resuspended in 1 ml of homogenization buffer and centrifuged a second time at 200,000×g for 1 hour. The pellet is resuspended in 50 μl of 100 mM Hepes-NaOH, pH 7.5, 4 mM EDTA, 10% (w/v) glycerol, 2 mM b-mercaptoethanol. 10 μl of the sample is added to 10 μl of a reaction mixture cocktail and incubated at 30° C. for 15 min. The final concentrations of components in the reaction mixture are: 100 mM Hepes-NaOH, pH 7.5, 1 mM b-mercaptoethanol, 100 mM oleyl CoA, 44 μM [2-$^{14}$C] malonyl CoA, 4 mM EDTA and 5% (w/v) glycerol.

The reaction is stopped and the β-ketoacyl product reduced to a diol by adding 400 μl of reducing agent solution comprised of 0.1M K$_2$HPO4, 0.4M KCl, 30% (v/v) tetrahydrofuran, and 5 mg/ml NaBH$_4$ (added to the solution just prior to use). The mixture is incubated at 37° C. for 30 min. Neutral lipids are extracted from the sample by addition of 400 μl of toluene. Radioactivity present in 100 μl of the organic phase is determined by liquid scintillation counting. The remaining toluene extract is collected and spotted onto a silica G TLC plate. The TLC plate is developed in diethyl ether:concentrated NH$_4$OH (100:1, v/v). The migration of the diol product of the reduction reaction is located by use of a cold diol standard.

B. Using this procedure plants can be assayed to determine the level of, or lack of, detectable β-ketoacyl synthase activity. For example, HEAR plants have high levels of β-ketoacyl synthase activity, while canola plants do not show appreciable enzyme activity. By this assay, plant species or varieties can be screened for β-ketoacyl synthase activity to determine candidates for transformation with the sequences of this invention to achieve altered VLCFA production, or to determine canditates for screening with probes for related enzymes.

The β-ketoacyl-CoA synthase enzyme assays demonstrate that developing embryos from high erucic acid rapeseed contain β-ketoacyl-CoA synthase activity, while LEAR embryos do not. Embryos from transgenic plants transformed with the jojoba cDNA exhibit restored β-ketoacyl-CoA synthase activity.

The jojoba cDNA encoding sequence thus appears to complement the mutation that differenitiates high and low erucic acid rapeseed cultivars. The phenotype of the transgenic plants transformed with the jojoba gene show that a single enzyme can catalyze the formation of 20, 22 and 24 carbon fatty acids. The seed oil from the primary LEAR transformants also contains higher levels of 22:1 than 20:1 fatty acids. This was also true for the majority of the individual T2 seed analyzed from the 7626–212/86–2 plant. Five T2 seeds that exhibited the highest VLCFA content also contain higher levels of 22:1 than 20:1. This suggests that the β-ketoacyl-CoA synthase is a rate limiting step in the formation of VLCFA's, and that as the enzyme activity increases in developing embryos, the fatty acid profile can be switched to the longer chain lengths. The increase in the amount of 24:1 fatty acid in the oil of transgenic HEAR plants and the increase in the amount of 22:1 in transgenic arabidopsis plants without a concomitant increase in the quantity of VLCFAs may be a result of a difference in substrate specificities of the jojoba, Arabidopsis, and Brassica enzymes rather than an increase in enzyme activity which is already abundant in HEAR and Arabidopsis.

Example 13—Other β-Keto-acyl-CoA Synthases

The active β-ketoacyl CoA synthase chromatographs on superose with a size consistant with the enzyme being composed of two 138 kDa subunits. This suggests that the enzyme is active as a multimer, although the enzyme may be a homodimer, a heterodimer, or a higher order multimer. The mass of one of the subunits is estimated to be 57 kDa by SDS gel electrophoresis and 59 kDA by calculation of the theoretical mass from translation of the cDNA sequence. The analogous soluble enzymes in plant and bacterial FAS, β-ketoacyl-ACP synthases, are active as dimers with ~50 kDa subunits. Chalcone and Stilbene synthases are also active as dimers.

The jojoba β-ketoacyl-CoA synthase subunit is a discrete 59 kDa protein. Thus, seed lipid FAE in jojobas is comprised of individual polypeptides with discrete enzyme activities similar to a type II FAS, rather than being catalyzed by the large multifunctional proteins found in type I FAS. Since the jojoba enzyme complements a Brassica mutation in FAE, it is possible that Brassica FAE is a type I system.

The dBEST data bank was searched with the jojoba β-ketoacyl-CoA synthase DNA sequence at the NCBI using BLAST software (Altschul et al., 1990). Two Arabidopsis clones (Genbank accession Z26005, Locus 39823; and genbank accession TO4090, Locus315250) homologous to the jojoba CE cDNA were detected. The 39823 clone exhibited a high degree of homology with the jojoba β-ketoacyl-CoA synthase clone. PCR primers were designed to PCR amplify and clone this sequence from Arabidopsis genomic DNA. No mRNA was detected in either developing Arabidopsis or developing Brassica seeds that cross hybridized with this clone. The probe was also hybridized to RFLP blots designed to determine if homologous sequences segregate with the difference between HEAR and LEAR lines. At low hybridization stringency there too many cross hybridizing bands are present to detect polymorphism between the HEAR and LEAR lines. At higher hybridization stringency, the bands did not cosegregate with the HEAR phenotype.

In order to isolate clones that encode related enzymes, the protein sequences of the jojoba β-ketoacyl-CoA synthase and the Arabidopsis locus 398293 were compared to find conserved domains. Several peptide sequences were identical in the jojoba β-ketoacyl-CoA synthase and the translation of the Arabidopsis homologue 398293. Two peptides: 1) NITTLG (amino acids 389 to 394 of the jojoba β-ketoacyl-CoA synthase) and 2) SNCKFG (amino acids 525 to 532 of the jojoba β-ketoacyl-CoA synthase) were also present in the translation of 398293. Degenerate oligonucleote primers AAYATHACNACNYTNGG (SEQ ID NO:15) and SWRT-TRCAYTTRAANCC (SEQ ID NO:16) encode the sense and antisense strands of the respective peptides.

The above primers PCR amplify an approximately 430 bp DNA fragment from both the jojoba β-ketoacyl-CoA synthase cDNA and the Arabidopsis 398293 sequence. These primers can be used to PCR amplify DNA sequences that encode related proteins from other tissues and other species that share nearly idendical amino acids at these conserved peptides. Using the degenerate oligonucleotides Arabidopsis green silique, HEAR, and LEAR RNA were subjected to RTPCR. Prominant bands of the expected size were amplified from all 3 RNAs. One clone was obtained from the reston PCR reaction, and 2 clones from the 212/86 reaction, which appear to form two classes of cDNA clones, designated CE15 and CE20. The protein sequences translated from these clones are >98% identical to one another. The clones are approximately 50% homologous to the jojoba β-ketoacyl-CoA synthase. The C-terminal portions of the proteins are more conserved, with the cDNAs sharing about 70% identity.

The proteins deduced from Brassica clones CE15 and CE20 can be aligned with the protein sequence of the jojoba β-ketoacyl-CoA synthase and Arabidopsis loci 398293 and 315250, with several regions of conserved protein sequence detectable. Different pairs of sense and antisense primers can thus be used to PCR amplify and isolate DNA encoding related β-ketoacyl-CoA synthases from many different tissues, of both plant and animal species.

The use of β-ketoacyl-CoA synthases obtained in this manner from other tissues or other species that have different substrate specificities can be used to create modified seed oils with different chain length fatty acids. This could include enzymes isolated from plant taxa such as lunaria, which synthesizes significant quantities of 24:1 fatty acid in its seed tissue. This could also include enzymes involved in cuticular wax synthesis of any plant species which may be capable of synthesizing fatty acids of chain lengths greater than 24 carbons.

These oligonucleotides may be especially useful for isolating the corresponding fatty acid synthase animal genes, which have not been previously cloned. Since the β-ketoacyl-CoA synthase expression is repressed in several demyelinating nervous system disorders of humans, for instance adrenoleukodystrophy, adrenomyeloneuropathy, and multiple svlrtodid(reviewed in Sargent and Coupland, 1994), the human genes may be useful in human gene therapy. Similarly, vegetable oils high in 22:1 or 24:1 may be useful dietary therapeutic agents for these diseases.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. A jojoba β-ketoacy 1-CoA synthase protein characterized as:

(a) free from intact jojoba cells;

(b) having a molecular weight of approximately 57 kDa;

(c) having preferrential activity toward long chain fatty acyl CoA substrates (d) capable of catalyzing the production of very long chain fatty acids from a long chain fart avcvl-CoA substrate and malonyl-Coa; and (e) being free of wax synthase activity.

2. A method for the production of very long chain fatty acids in a plant cell, said plant cell being otherwise incapable of producing said very long chain fatty acids, comprising the steps of:

growing a plant under conditions wherein said plant produces long chain fatty acyl-CoA molecules, in the presence of an expression product of a β-ketoacyl-CoA synthase DNA sequence operably linked to regulatory elements for directing the expression of said DNA sequence such as to effect the contact between such long chain fatty acyl-CoA molecules and said β-ketoacyl-CoA synthase, wherein (i) said β-ketoacyl-CoA synthase is capable of catalyzing the production of very long chain fatty acids from a long chain fatty acyl-CoA substrate and malonyl-CoA, (ii) said DNA sequence is heterologous to said plant, and (iii) very long chain fatty acids are produced in said plant.

3. The method of claim 2 wherein said regulatory elements direct preferential expression of said DNA sequence in plant seed embryo cells and wherein said very long chain fatty acids are produced in plant seed.

4. A whole plant, plant part or plant seed containing very long chain fatty acids produced in accordance with claim 2.

5. A plant seed produced in accordance with claim 3.

6. A method for decreasing the proportion of very long chain fatty acids in a plant from a given proportion of very long chain fatty acids comprising the steps of:

growing a plant under conditions wherein said plant produces very long chain fatty acids and a β-ketoacyl-CoA synthase capable of catalizing the production of very long chain fatty acids from a long chain fatty acyl-Coa substrate and malonyl-CoA, in the presence of a β-ketoacyl-CoA-decreasing DNA sequence operably linked to regulatory elements for directing the expression of said DNA sequence in said cell, wherein said DNA sequence encodes a β-ketoacyl-CoA DNA sequence of said plant and the expression of said DNA sequence results in a decrease in the production of β-ketoacyl-CoA synthase by said plant cell and a decrease in the proportion of very long chain fatty acids produced by said plant cell.

7. The method of claim 6 wherein said regulatory elements direct the antisense transcription of said DNA sequence.

8. The method of claim 6 wherein said regulatory elements direct preferrential expression of said DNA sequence in plant seed embryo cells and wherein said very long chain fatty acids and said β-keto acyl-CoA are produced in plant seed.

9. A plant seed cell produced in accordance with claim 6.

* * * * *